(12) United States Patent
Dullen

(10) Patent No.: US 11,653,877 B2
(45) Date of Patent: May 23, 2023

(54) METHOD AND APPARATUS FOR THE MEASUREMENT OF AUTONOMIC FUNCTION FOR THE DIAGNOSIS AND VALIDATION OF PATIENT TREATMENTS AND OUTCOMES

(71) Applicant: Deborah Dullen, Philadelphia, PA (US)

(72) Inventor: Deborah Dullen, Philadelphia, PA (US)

(*) Notice: Subject to any disclaimer, the term of this patent is extended or adjusted under 35 U.S.C. 154(b) by 114 days.

(21) Appl. No.: 16/458,130

(22) Filed: Jun. 30, 2019

(65) Prior Publication Data

US 2019/0336069 A1  Nov. 7, 2019

Related U.S. Application Data

(62) Division of application No. 14/992,016, filed on Jan. 10, 2016, now Pat. No. 10,376,203.

(60) Provisional application No. 62/101,992, filed on Jan. 10, 2015.

(51) Int. Cl.
*A61B 5/00* (2006.01)
*A61B 5/0205* (2006.01)

(52) U.S. Cl.
CPC .......... *A61B 5/4824* (2013.01); *A61B 5/0024* (2013.01); *A61B 5/02055* (2013.01); *A61B 5/4848* (2013.01); *A61B 5/6831* (2013.01);

*A61B 5/6832* (2013.01); *A61B 2562/063* (2013.01); *A61B 2562/066* (2013.01)

(58) Field of Classification Search
CPC .................................................. A61B 5/4824
See application file for complete search history.

(56) References Cited

U.S. PATENT DOCUMENTS

| | | | |
|---|---|---|---|
| 2008/0249430 A1* | 10/2008 | John | A61B 5/369 600/544 |
| 2013/0310660 A1* | 11/2013 | Zuckerman-Stark | A61B 5/7267 600/301 |

* cited by examiner

*Primary Examiner* — Michael W Kahelin
(74) *Attorney, Agent, or Firm* — Z IP Law PLLC

(57) ABSTRACT

A pain measurement and diagnostic system (PMD) for bioanalytical analysis of pain matrix activity and the autonomic nervous system to diagnose and validate patient treatments, health status and outcomes to diagnose and validate patient treatments and outcomes. The PMD is implemented using medical devices for measuring and reporting objective measurements of pain through patient monitoring and analyzing related biological, psychological, social, environmental, and demographic factors that may contribute to and effect physiological outcomes for patients and through the analysis, improve diagnosis of pain, the evaluation of related disease states, and treatment options.

11 Claims, 27 Drawing Sheets

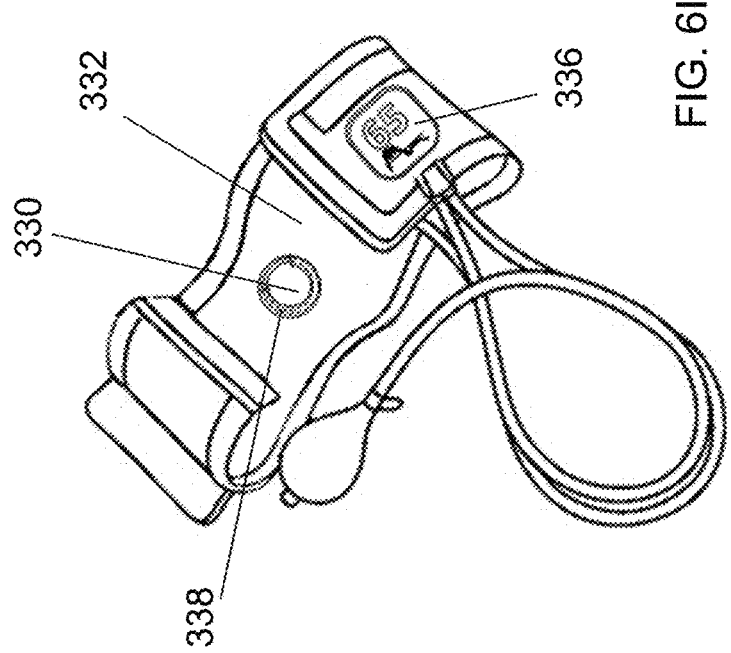
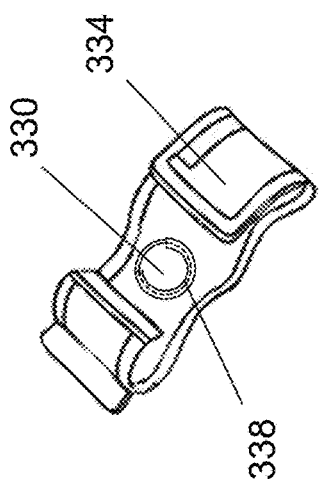
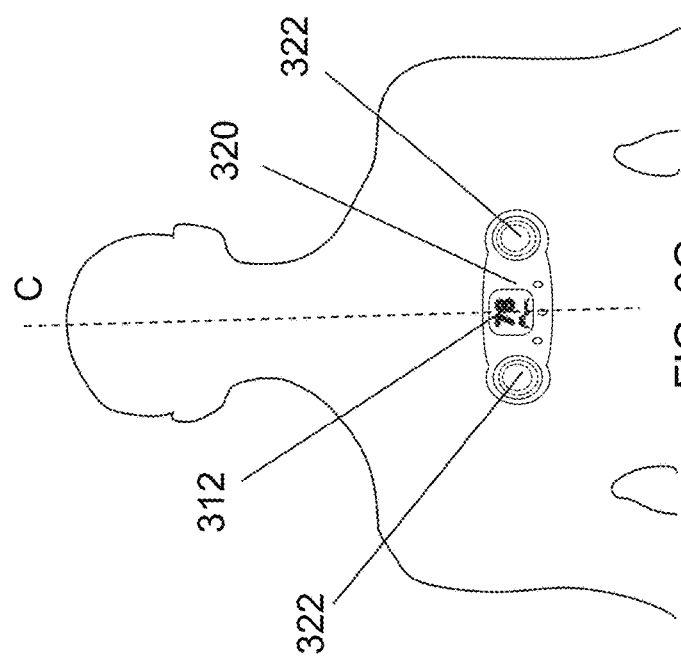
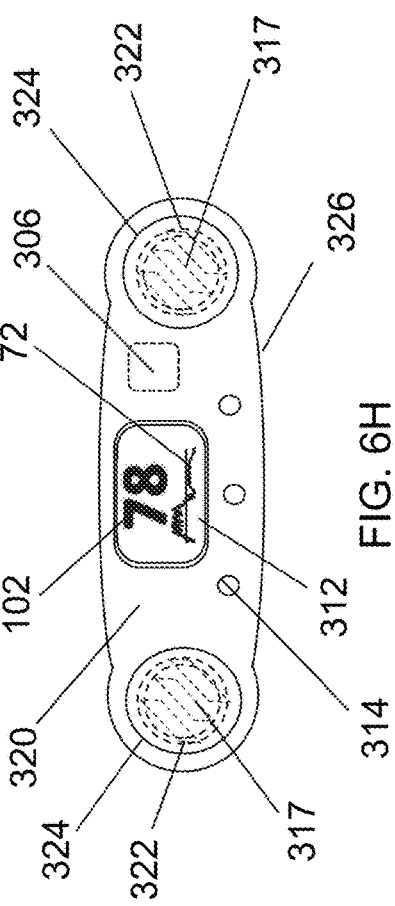

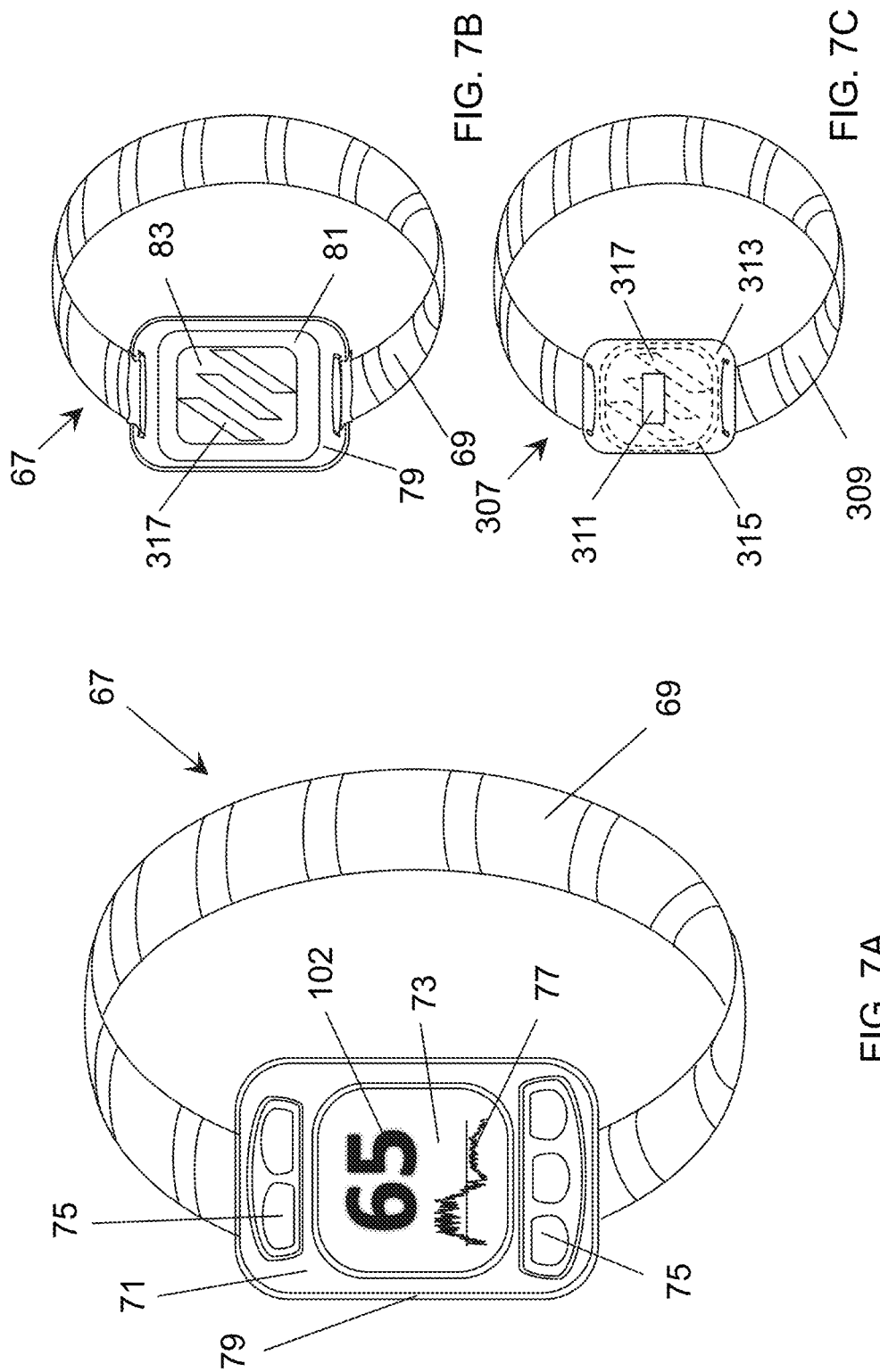

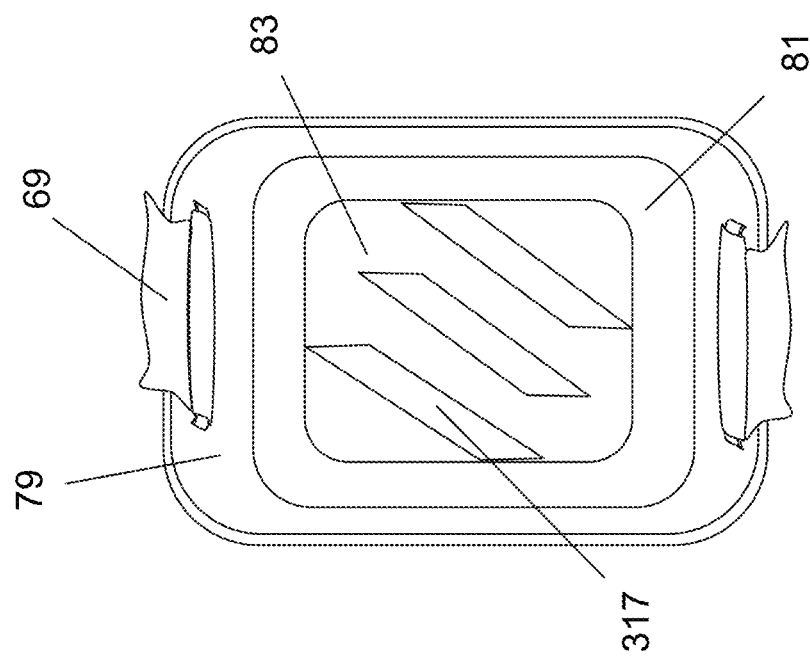
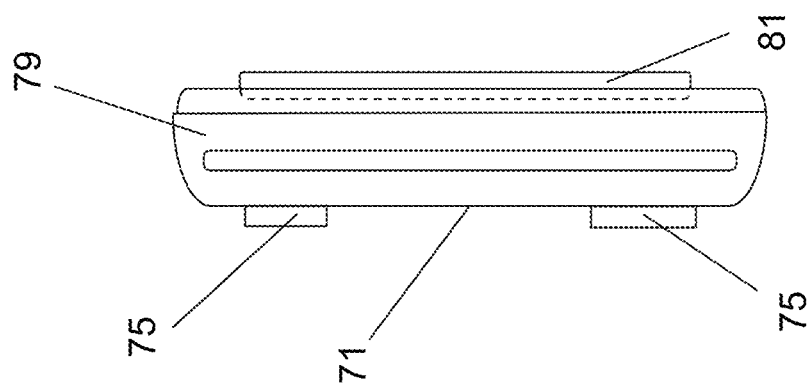
FIG. 8B
FIG. 8A

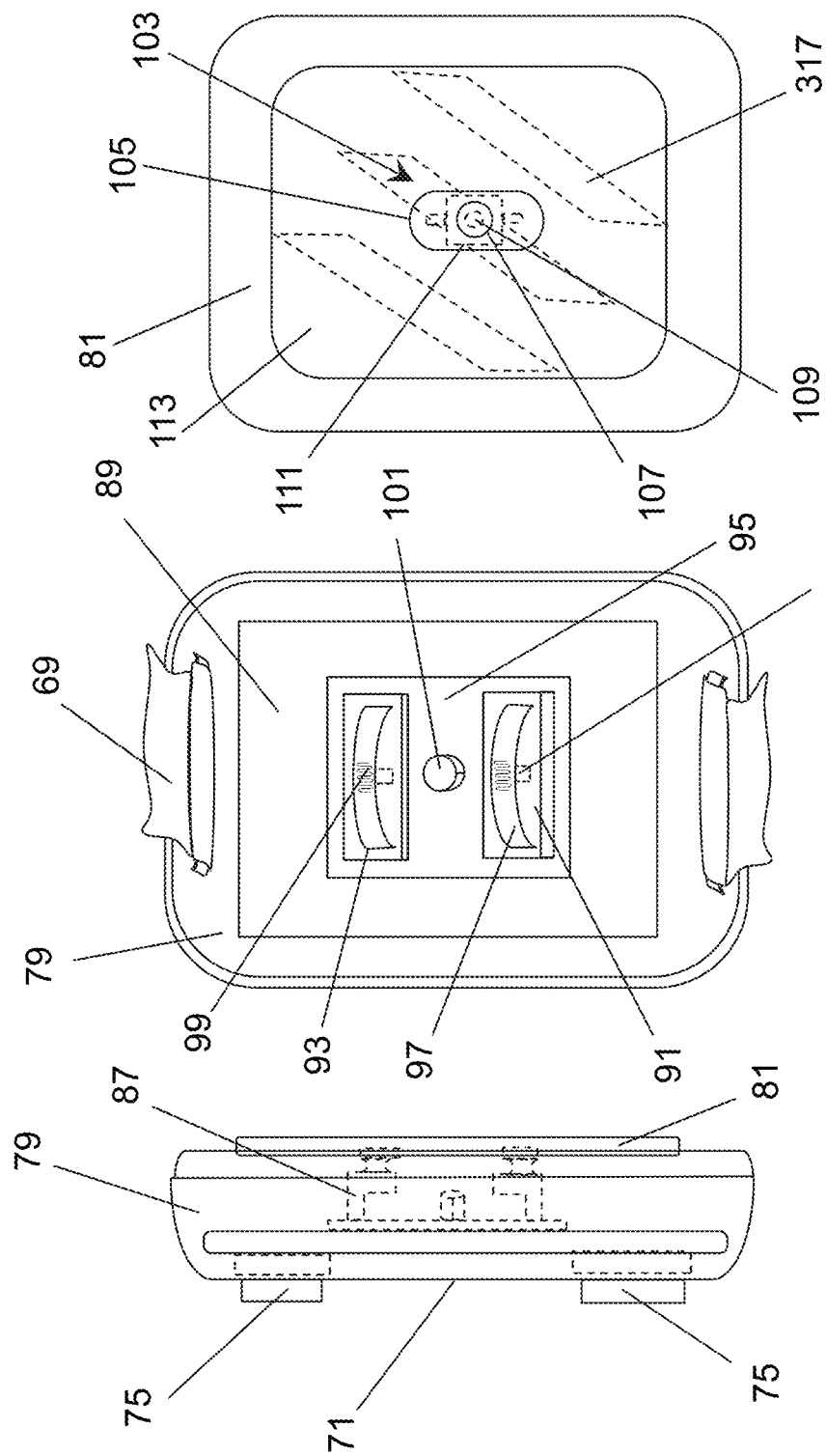

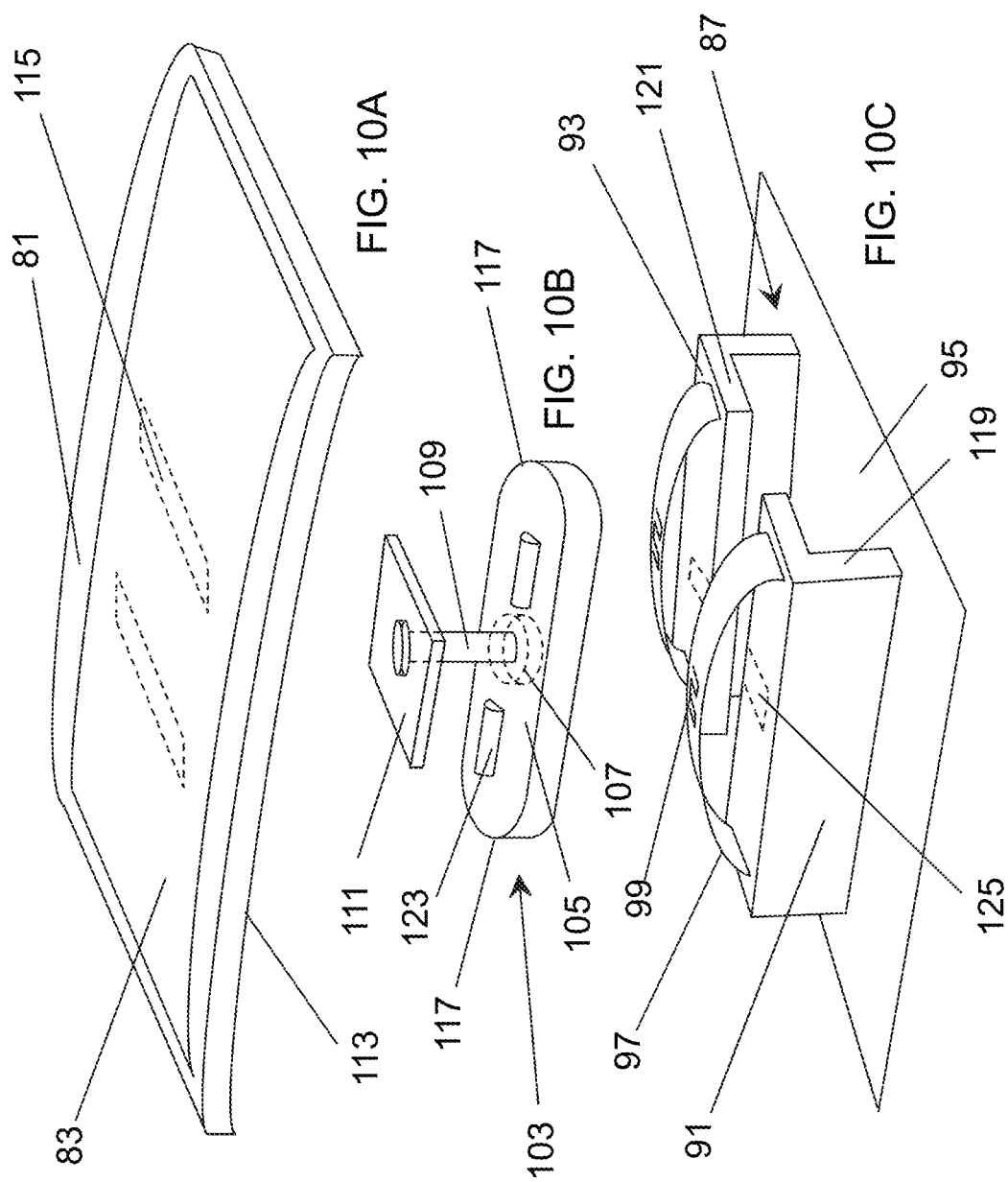

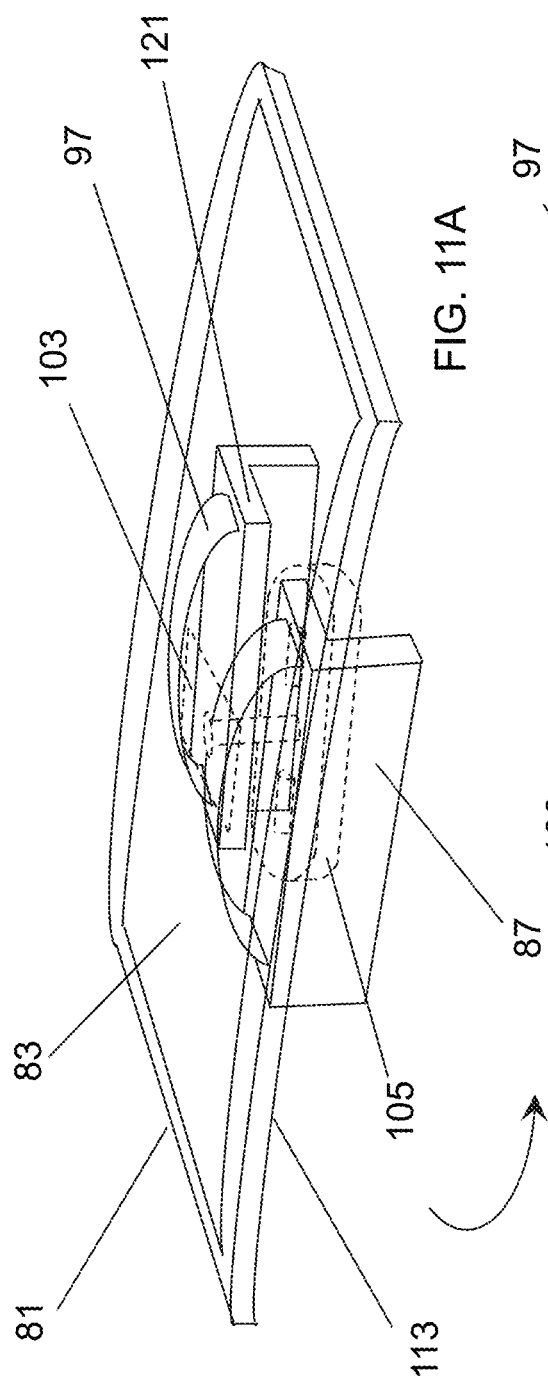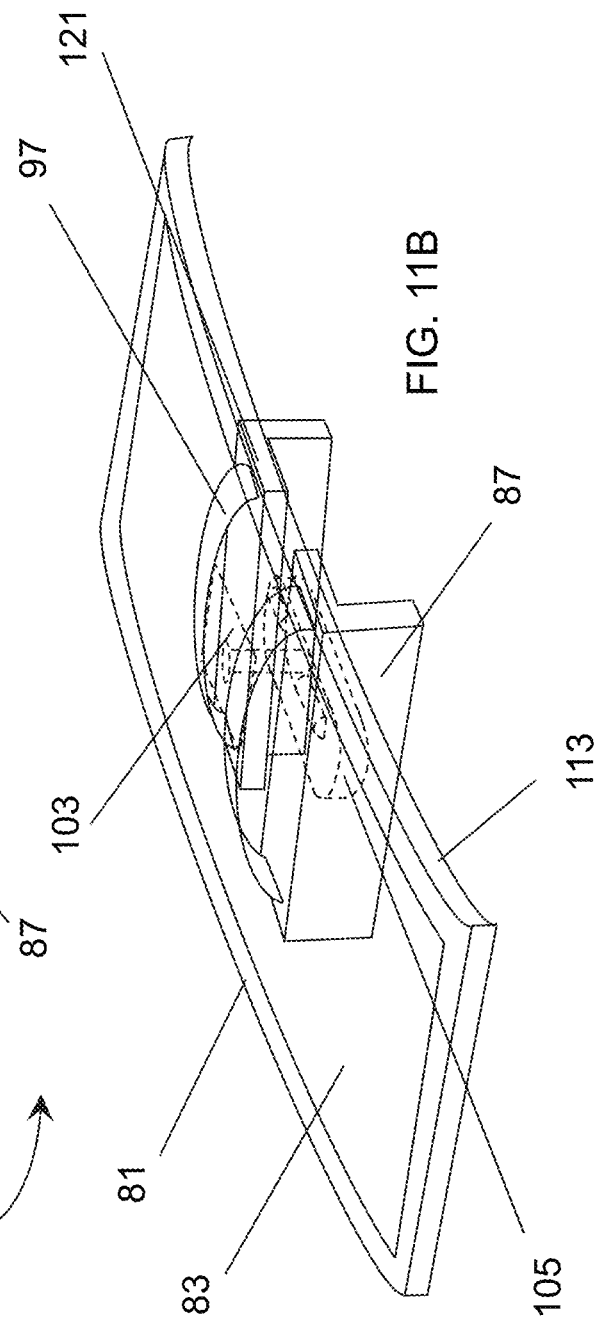

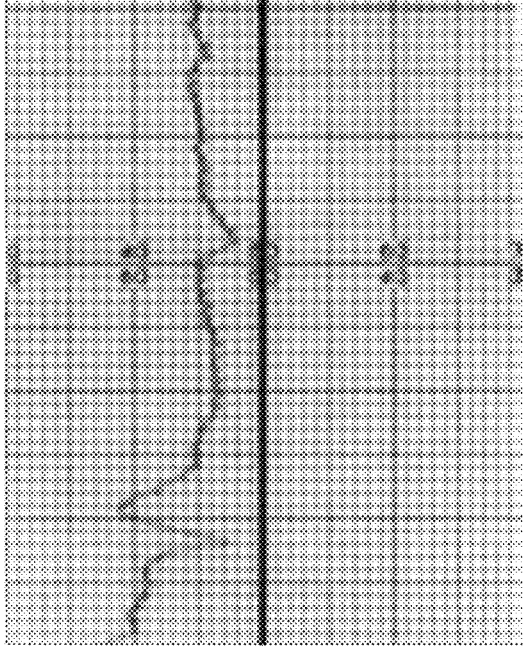
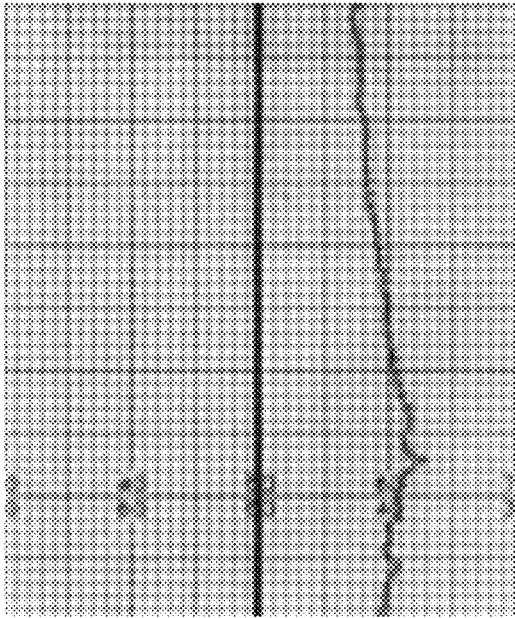
FIG. 23

METHOD AND APPARATUS FOR THE MEASUREMENT OF AUTONOMIC FUNCTION FOR THE DIAGNOSIS AND VALIDATION OF PATIENT TREATMENTS AND OUTCOMES

RELATED PATENT APPLICATION

This application is a divisional patent application of U.S. patent application Ser. No. 14/992,016 (now U.S. Pat. No. 10,376,203) filed on Jan. 10, 2016 entitled METHOD AND APPARATUS FOR THE MEASUREMENT OF AUTONOMIC FUNCTION FOR THE DIAGNOSIS AND VALIDATION OF PATIENT TREATMENTS AND OUTCOMES that claims the benefit of U.S. Provisional Patent Application No. 62/101,992 filed Jan. 10, 2015 entitled METHOD AND APPARATUS FOR THE MEASUREMENT OF AUTONOMIC FUNCTION which is hereby incorporated herein by reference in its entireties.

FIELD OF THE INVENTION

The present invention relates to a pain measurement and diagnostic system (PMD) for bioanalytical analysis of pain matrix activity and the autonomic nervous system to diagnose and validate patient treatments, health status and outcomes. The PMD is implemented using medical devices for measuring and reporting objective measurements of pain through patient monitoring and analyzing related biological, psychological, social, environmental, and demographic factors that may contribute to and effect physiological outcomes for patients and through the analysis improve diagnosis of pain, evaluation of related disease states, and treatment options.

BACKGROUND OF THE INVENTION

Currently there exists no valid and reliable method of objectively quantifying an individual's experience of pain (Younger J et al, Pain Outcomes: A Brief Review of Instruments and Techniques. Curr Pain Headache Rep., 2009 February; 13(1):39-43). In the United States, approximately 100 million adults—more than the number affected by heart disease, diabetes, and cancer combined—suffer from common chronic pain conditions (Tsang, A et al, Common chronic pain conditions in developed and developing countries: Gender and age differences and comorbidity with depression-anxiety disorders. Journal of Pain. 2008; 9(10): 883-891.) with an annual national economic cost associated with chronic pain estimated to be $560-635 billion in 2011. The aging of the United States population means that a growing number of Americans will experience the diseases with which chronic pain is associated—diabetes, cardiovascular disorders, arthritis, and cancer, among others (Cherry et al, Population aging and the use of office-based physician services. NCHS Data Brief, No. 41. Hyattsville, Md.: National Center for Health Statistics). Increases in obesity will result in more orthopedic problems related to the degradation of cartilage (Richettel et al., 2011). As a result, there will be a greater number of joint replacement surgeries, occurring in younger adult populations (Harms, S., R. Larson, A. E. Sahmoun, and J. R. Beal. 2007. Obesity increases the likelihood of total joint replacement surgery among younger adults. International Orthopaedics 31(1):23-26; Changulani et al., 2008); resulting in associated acute and also potentially chronic pain. Increases in disease states associated with pain will not only be experienced in the US.

A UK Report from 2009, stated that, "chronic pain is two to three times more common now than it was 40 years ago" (U.K. Department of Health. 2009. 150 years of the chief medical officer: On the state of public health. Annual Report. London: U.K. Department of Health; PAGE 34). There is no question that pain, and other complex chronic disease states, are a major public health challenge. According to the Institute of Medicine's 2011 study—Relieving Pain in America: A Blueprint for Transforming Prevention, Care, Education, and Research, pain is a uniquely individual and subjective experience that depends on a variety of biological, psychological, and social factors, and different population groups experience pain differentially (IOM (Institute of Medicine). 2011. Relieving Pain in America: A Blueprint for Transforming Prevention, Care, Education, and Research. Washington, D.C.: The National Academies Press.). Why one person suffers an injury and reports modest pain and another with a similar injury reports serious pain depends on many factors: genetic characteristics, general health status and comorbidities, pain experiences from childhood on, the brain's processing system, the emotional and cognitive context in which pain occurs, and cultural and social factors. Costly procedures often are performed when other actions should be considered, such as prevention, counseling, and facilitation of self-care, which are common features of successful treatment. In addition, adequate pain treatment and follow-up may be thwarted by a mix of uncertain diagnosis and societal stigma consciously or unconsciously applied to people reporting pain, particularly when they do not respond readily to treatment (IOM (Institute of Medicine). 2011. Relieving Pain in America: A Blueprint for Transforming Prevention, Care, Education, and Research. Washington, D.C.: The National Academies Press). For these reasons, it is important to develop an objective manner to measure pain, and general physical symptoms, but then to further combine and analyze sensor acquired data with additional factors that influence the individual experience of pain, and other related healthcare issues and disease states. Currently, physicians and caregivers rely upon a patient's own description of symptoms such as pain, which is an example of a physical outcome that has defied objective measurement. Today, uni-dimensional scales are used to evaluate pain. A commonly used scale is the numerical rating scale (NRS), which typically consists of scores 0-10, with the far left denoting "no pain" and the far right end of the scale as "worst pain imaginable". In general, it is difficult for a subject to accurately describe their pain, but especially while under duress, or for example patient populations that may struggle with communication, such as children, elderly patients suffering from dementia, and those who do not speak the same language as the treating medical professional. Clinical findings that can be seen—a broken bone on an x-ray, for example—do not necessarily correlate well with the severity of pain the patient perceives. Elderly patients experience pain twice as often as those under the age of 60 which is thought to relate to their inability to accurately communicate pain and intensity or source of pain (Herr K et al, Assessment and measurement of pain in older adults. Clin Geriatric Med, 2001 August; 17(3):457-vi) (Weiner D et al, 1999. Pain in nursing home residents: An exploration of prevalence, staff perceptions, and practical aspects of measurement. Clin of J Pain. 1999; 15:92 [PubMed: 10382922]). People afflicted by pain may find the rough tools of language inadequate to convey the character and intensity of their experience and its significance to them. This can be a substantial barrier to obtaining adequate treatment (Werner, A., and K. Malterud. 2003. It is hard work behaving as a credible patient: Encounters between women with chronic pain and their doctors. Social Science & Medicine 57(8):1409-1419). According to the Institute of Medicine, (IOM, 2011), pain and its severity, how it evolves, and the effectiveness of treatment depend on a constellation of biological, psychological, and social factors, such as the following:

Biological—the extent of an illness or injury and whether the person has other illnesses, is under stress, or has specific genes or predisposing factors that affect pain tolerance or thresholds;

Psychological—anxiety, fear, guilt, anger, depression, and thinking the pain represents something worse than it does and that the person is helpless to manage it (Ochsner, K., J. Zaki, J. Hanelin, D. Ludlow, K. Knierim, T. Ramachandran, G. Glover, and S. Mackey. 2008. Your pain or mine? Common and distinct neural systems supporting the perception of pain in self and other. Social Cognitive and Affective Neuroscience 3(2):144-160);

Social—the response of significant others to the pain—whether support, criticism, enabling behavior, or withdrawal—the demands of the work environment, access to medical care, culture, and family attitudes and beliefs.

Beyond the lack of a currently available objective measures for pain and more recent agreement that pain, and other complex chronic diseases, are a constellation of biological, psychological, and social factors there is still further need to address existing issues with under-treatment of patients suffering from chronic pain resulting from shortened hospital stays and lack of at-home monitoring and telemedicine. As outlined in IOM's Relieving Pain in America report: In 2007, almost half of Emergency Department patients presented with pain that was severe 22% or moderate 23%. (Niska et al, National Hospital Ambulatory Medical Care Survey: 2007 emergency department summary. National Health Statistics Reports 26. Hyattsville, Md.: National Center for Health Statistics) Chest or abdominal pain was the leading reason for the visit among those aged 15-64, while chest or abdominal pain plus shortness of breath was the leading reason for the visit among those 65 and older. There were 10 million inpatient surgeries and 17.4 million hospital outpatient surgeries in 2009 (AHA (American Hospital Association). 2011. Trendwatch chartbook 2011. Tables 3.1 and 3.4. http://www.aha.org/aha/research-and-trends/chartbook/index.html (accessed Mar. 3, 2011)). Between 10 and 50 percent of people having regularly performed surgical operations—groin hernia repair, breast and thoracic surgery, leg amputation, and coronary artery bypass surgery—go on to experience chronic pain, often due to damage to nerves in the surgical area during the procedure (Kehlet, et al, Persistent postsurgical pain: Risk factors and prevention. Persistent postsurgical pain: Risk factors and prevention. Lancet. 2006; 367(9522):1618-1625.). Today's shorter hospital stays—down, on average, from 7.2 days in 1989 to 5.4 days in 2009 (AHA, 2011)—and the trend toward outpatient surgery may not permit sufficient opportunity to assess patients' postsurgical pain or establish an appropriate course of postoperative analgesia (perhaps one that can be administered at home), shown to be effective in hip and knee replacement, for example (Schug et al. Chronic pain after surgery or injury. 2011 Pain Clinical Updates 19. Seattle, Wash.: International Association for the Study of Pain). There is currently no way to monitor an out-patient's response to pharmaceutical treatment and the effectiveness of treatment related to pain and other related chronic disease states.

Recent improvements in sensor technology, powerful and miniaturized micro-controllers, systems on a chip (SOCs), low energy wireless communication, and power management add up to the opportunity for new wearable devices that allow for long-term, at-home, patient monitoring of physiologic measurements via patient worn sensors, cloud computing for data storage and analysis, and integration with networks and mobile devices provide communication with healthcare providers and healthcare systems. What is not measured in these devices of the prior art is a measurement of the severity of pain that a patient is experiencing either due to an immediate injury or as a chronic result of disease or other infirmary. Using the pain measurement and diagnostic system (PMD) of the present invention, pain is objectively measured to provide currently unavailable biophysical information that will assist in diagnosis, the selection and validation of treatments, and may provide patient incentives to continue in performing effective treatments. By tracking and evaluating biophysical measurements, "pain matrix" activity in the form of a pain modulatory circuit with inputs that arise in multiple areas including cortical sites, the rostral anterior cingulate cortex (rACC), pregenual cingulate cortex, (pCC), somatosensory cortex 1 and 2, the thalamus and hypothalamus, insula, the amygdala, periaqueductal gray region (PAG), and additional descending pathway structures, and vagal tone may be correlated to determine stress, cognition, emotion, disease states, and evaluation of threat to determine pain state, modulation of pain, level of health and healing, and the vulnerability toward illness of a patient (Ossipov et al. Central Modulation of Pain. The Journal of Clinical Investigations: November 2010; 120(11): 3779-3787.)

Pain measurements may also assist physicians in prescribing proper dosage based on the patient's reaction to medication. Patients are receiving inadequate access to pain medications due to the well-publicized abuse of opioids and the subsequent reluctance of the many in the medical community to write prescriptions for non-institutionalized patients. According to researchers at the CDC, to reverse the epidemic of opioid drug overdose deaths and prevent opioid-related morbidity, efforts to improve safer prescribing of prescription opioids must be intensified (Paulozzi L J, Jones C, Mack K, Rudd R. Vital signs: overdoses of prescription opioid pain relievers—United States, 1999-2008. MMWR Morb Mortal Wkly Rep 2011; 60:1487-92). Between 2013 and 2014, the age-adjusted rate of death involving synthetic opioids, other than methadone (e.g., fentanyl) increased 80% (Rudd et al. Increases in Drug and Opioid Overdose Deaths—United States, 2000-2014. CDC: Morbidity and Mortality Weekly Report (MMWR). Jan. 1, 2016/64(50); 1378-82). In 2014, there were approximately one and a half times more drug overdose deaths in the United States than deaths from motor vehicle crashes (CDC. Wide-ranging online data for epidemiologic research (WONDER). Atlanta, Ga.: CDC, National Center for Health Statistics; 2015. Available at http://wonder.cdc.gov). Adequate pain treatment and follow-up may be thwarted by a mix of uncertain diagnosis and societal stigma consciously or unconsciously applied to people reporting pain, particularly when they do not respond readily to treatment (TOM, 2011).

There is currently no objective measure for pain and as a result physicians struggle to both diagnose and treat pain. A pain monitor would address this major health crisis by facilitating healthcare providers' prescribing of opioid pain relievers; in particular, prescribing the appropriate dose. American Geriatrics Society cites delays in access to prescribed opioids for nursing home patients, including those who are terminally ill, and the American Cancer Society has recognized the frequent inaccessibility of opioids necessary for treating some pain (TOM, 2011). According to the White House action plan, between 2000 and 2009, the number of opioid prescriptions dispensed by retail pharmacies grew by 48 percent—to 257 million. However, based on increased regulations to limit opioid abuse, twenty-nine percent of primary care physicians and 16 percent of pain specialists report they prescribe opioids less often than they think appropriate because of concerns about regulatory repercussions (Breuer et al, Pain management by primary care physicians, pain physicians, chiropractors, and acupuncturists: A national survey. Southern Medical Journal 2010 103(8):738-747).

Accurate medication dosage, early intervention, and physician education are necessary. The following is a list of potential savings from improvements in pain prevention, care, education, and research per IOM 2011 Relieving Pain in America report:

- better treatment of acute pain, through education about self-management and better clinical treatment, in order to avoid the progression to chronic pain, which is more difficult and more expensive to treat and generates high health care utilization;
- reductions in health problems and complications of other physical and mental diseases and conditions associated with chronic pain that also are expensive to treat;
- more cost-effective care of people with chronic pain when self-management and multimodal approaches are used more often, primary care physicians are educated and empowered to treat most people with pain appropriately, and unnecessary diagnostic tests and procedures and referrals to specialists are avoided;
- better tailoring of treatment to individuals based on new research findings and integration of those findings into patterns of care. Patient Controlled Analgesia (PCA) devices which enable the patient to self-administer pain medicine are used to administer medications in institutional settings. While there is currently no commercially available way to objectively measure pain, and rising concern over abuse of opioids and other prescriptions, PCA's are utilized and do have advantages. Research shows PCA is superior to intermittent injection of pain medication, even by the IV route (D'Arcy, Y. (2007). Pain pointers: Safe pain relief at the push of a button. Nursing Made Incredibly Easy, 5(5), 9-12). Patients use less narcotic, do not have to wait for the nurse to bring the medication, and have greater overall satisfaction with better analgesia and lower pain scores than patients who request analgesia from the nursing staff (Smeltzer, S., et al. (2008). Textbook of medical surgical nursing (11th ed.). Philadelphia: Lippincott). By controlling pain, patients can move more readily, take deep breaths and ambulate earlier, reducing the risk of post-operative complications (D'Arcy, Y. (2008). Keep your patient safe during PCA. Nursing, 38(1), 50-55).

Despite these advantages there are negatives. For example, they cannot be readily used, if at all, for infants, toddlers, and other who cannot operate the device due to either a physical disability such as a spinal cord injury or individuals unable or unwilling to understand instructions for use. Patients who are obese or asthmatic, or those taking drugs that potentiate opiates, such as sedatives or hypnotics, muscle relaxants and antiemetics, should not use PCA. Patients with sleep apnea should not use PCA (D'Arcy, Y. (2011). New thinking about postoperative pain management. OR Nurse, 51(11): 28-36). Also, current PCA devices continue to operate based upon the subjective measure of self-assessment. Without a means to normalize patient self-assessment inconsistent treatment remains an issue for patients. PCA combined with an objective measure for pain using the PainTrace medical devices and components and features of the pain measurement and diagnostic system (PMD) of the present invention may alleviate many existing issues.

SUMMARY OF THE INVENTION

The pain measurement and diagnostic system (PMD) of the present invention uses medical devices to acquire data, and physiological measurements, related to pain and demographics, medical information, activities, and patient and healthcare provider information further acquired through PMD specific components and features to establish baselines for both healthy patients and for patients that may be suffering from various disease states. Using the PMD, collected data related to pain and associated physiological measurements, are transformed to diagnostic indicators, or healthcare provider tools, based on factors related to patient demographics, comorbidities, interventions, and other known contributors that affect the overall experience of pain, and additionally are indicators of health, including genetics, biomarkers, past experiences, pain matrix neurological modulation of pain, activities, and emotional and cultural influences. The PMD will acquire and store pain measurements, physiological measurement, and relevant data, correlating with surveys and the current "gold standard", Visual Analog Scale (VAS) and similar scales for the self-report of pain to translate collected data to establish a more accurate and reliable scale of pain measurement, and related disease diagnosis and monitoring, based on physiological measurements and the biopsychosocial factors related to the experience of pain.

Recent findings through neurological research have determined the existence of a brain-based "pain matrix" responsible for the processing and modulation of pain. The central nucleus of the amygdala (CeA) is central to this pain matrix with neurological connections linked to the periaqueductal gray region (PAG), responsible for descending pain pathways from the brain, and cortical sites that together with the amygdala provide emotional-affective modulation of cognitive functions in pain (Ossipov). et al. Central Modulation of Pain. The Journal of Clinical Investigations: November 2010; 120(11): 3779-3787, Neugebauer et al. Forebrain pain mechanisms. Brain Res Rev. 2009; 60 (1): 226-242). In particular, the amygdala produces the largest asymmetry, and research has shown that the amygdala is a critical component of the pain matrix. (Veinante P et al. The Amygdala between sensation and affect: a role in Pain. J Molec Psych 2013, 1:9 http://www.jmolecularpsychiatry.com/content/1/1/9). Studies have evidenced that only the right central nucleus of the amygdala (CeA) has been related to both acute and chronic pain. (Ossimov, 33-40), (Ji, G. et al. Hemispheric lateralization of pain processing by amygdal neurons. J Neurophysiol. 2009; 102 (4): 253-2264, Carrsquillo, Y. et al. Hemispheric lateralization of a molecular signal for pain modulation in the amygdala. Mol Pain. 2008; 4:24). By measuring EDA using the contralateral placement of sensors, or electrodes, direct measurements of brain pain processing from the "pain matrix" demonstrate the "collection of brain regions that are involved in neurological functions, including cognition, emotion, motivation, and sensation as well as pain" (Ossipov), et al. Central Modulation of Pain. The Journal of Clinical Investigations: November 2010; 120(11): 3779-3787). Large asymmetric differences in EDA between the left and right side have been demonstrated upon direct stimulation of particular brain regions, some of which form the aforementioned "pain matrix." Boucesin in, Electrodermal Activity page 41, summarizes three main pathways connecting the central nervous system (CNS) to EDA. In particular, the pathway termed "EDA1" arises from the limbic region which includes the amygdala as a brain region that elicits ipsilateral EDA (Mangina C A, et al. Direct Electrical Stimulation of Specific Human Brain Structures and Bilateral Electrodermal Activity. Int J Psychophysiol, 1996 22(1-2), 1-8; Mangina C A, et al. Even-related Brain Potentials, Bilateral Electrodermal Activity and Mangina-Test Performance in Learning Disabled/ADHD Pre-adolescents with Severe Behavioral Disorders as Compared to Age-matched Normal Controls. Int J Psychophysiol, 2000 37(1), 71-85; Boucesin W. Electrodermal Activity. (2nd Ed.); Page 41. Springer-Verlag (New York 2012).).

The use of contralateral sensors for the measurement of EDA and a correlation of these measurements to pain is described in U.S. Pat. No. 6,347,238 to Levengood and Gedye, and others. However, these findings were presented somewhat in isolated experiments and the devices used presented challenges in sensitivity and repeatability. In Burke, U.S. Pat. No. 8,560,046, a device that reliably measured pain was disclosed, however the integration of collected data with other biophysical measurements and particularly with ipsilateral measurements was not described.

This patent outlines an integrated pain measurement and diagnostic that builds and improves on previously granted claims for contralateral sensor placement in the measurement of autonomic nervous system function and pain matrix activity. The PMD combines a series of data management systems to acquire biosignals, integrate patient information, perform diagnosis, and treatment interventions and deliver pain measurement and diagnostic outcomes that provide useful and useable information for the HCP. In addition to the diagnosis of pain, the pain measurement devices of the PMD also provide early diagnosis of intestinal distress, allergies and respiratory infection, sports injury related to tendon and ligament damage, as well as diagnosis of chronic pain related to back injury, dental and migraine cases among others. Using the PMD it has demonstrated statistically significant correlation to patient self-report of pain and the evaluation of pre- and post-treatment pain states as well as the aforementioned disease states.

The PMD as described herein evaluates physiologic measurements, tracks patient activity, interacts with patient via questions pertinent to their diagnosis, and aids decisions around on-going treatment regimens and alterations to improve outcomes. The physiologic measurements evaluated by the PMD may include, but are not limited to, pain-related asymmetric biosignals specific to the present invention, heart rate, heart rate variability, photoplethysmogram (PPG), blood pressure, skin temperature, movement, GSR, and other vital signs. Through the analysis and continual integration of data, the PMD has an evolutionary nature, in that it will constantly be evaluating data input from a number of different sources, for example health care providers who are gathering biometrics data on patients that may be suffering from various disease states, new research and journal references related to specific disease states, and biophysical data through multiple biosensors used in monitoring the patient with the initial scope of analysis directed to include evaluations of acute and chronic pain as it relates to interventions. Through the gathering of data points that comprise biological, psychological, social measures, and other relevant data fields combined with the disease state diagnostic data points, the PMD will store, data mine, integrate, and transform the gathered data in a HIPAA compliant manner, or in an appropriate fashion to protect patient privacy rights, in order to parallel and integrate data on patients using a biopsychosocial platform, or one that comprises other appropriate factors for data points, to further increase the understanding of a disease state or evaluate an intervention. The PMD may further correlate device generated measurements of pain and the central nervous system activity as related to respiratory sinus arrhythmia, heart rate and heart variability, respiration, photoplethysmogram (PPG), movement, and skin temperature measurements from other sensors in order to determine pain matrix activity and vagal tone that may provide information on the vulnerability of the patient to stress and illness. (Loggia et al, Autonomic responses to heat pain: Heart rate, skin conductance, and their relation to verbal ratings and stimulus intensity. Pain. 2011; 152 (3): 592-598). By measuring the manifestation of pain in the nervous system combined with data regarding biological, behavioral, environmental, psychological, and social factors, the PMD may further derive statistical computations of patient and population factors and isolate factors to be used for diagnosis to increase the understanding of various disease states via the multi-dimensional transformation of data through the analysis using the pain and physiological measurements generated by the device, and components and features integrated within the PMD platform.

The individual nature of a patient's interpretation of pain and the current biospsychosocial approaches to treatment of complex disease states presents barriers to fully understand a patient's experience and how pain relates to treatment and successful outcomes. The PMD, as an integrated device, network, and software system, removes subjective analysis and resolves issues of patient inconsistencies and limitations by integrating objective sensor measurements of pain and "pain matrix" central nervous system activity with health information, demographics, and physiological measurements through a unique graphical user interface (GUI) that makes data accessible and useful for health care providers (HCP) and patients. The PMD uses pain measurement acquisition software to normalize and correlate measurements from for example the pain matrix and associated signals, and integrates aspects of this measured pain data to other collected sensor data to more effectively present the biophysical state of a patient at specific time points. The PMD further integrates information from specific fields through specific questions related to patient activities and disease states. For example, a migraine patient may receive a series of questions as designated time points related to pain inflections that represent a change in pain state. The collected responses are correlated and may show an increase in pain that is related to activities such as eating, exercise, stress, and other daily interactions that may identify the source of pain or exasperation, or improvement, of the diseased or healthy state. The PMD further integrates patient health status, physical biosignal device measurements, diagnosis, research, and healthcare provider (HCP) intervention and management in order to reinforce positive patient emotions, to educate, to promote healthy activities, and to encourage compliance to improve outcomes through remote patient engagement. The PMD further provides a personal health record storage platform that will additionally function as universal health record allowing individual health and activity data and electronic health record data to be combined for analysis. The analysis of health information, demographics, and physiological measurements with pain matrix and nervous system measurements presented through the PMD System of the present invention will result in integration of data and ongoing monitoring that benefits the healthcare community and individuals with custom and global analysis of health factors, specific disease and health related data, and effective treatment options to ultimately improve understanding of a disease state, or general health, related influencing factors, and best practices for safe and effective treatment interventions and regimens. The integration and optimization of this data within contextual timeframes and associated patient knowledgebase presented by the BioTraceIT analysis application software of the PMD can dramatically aid an HCP in diagnosis, patient monitoring, patient engagement, treatment options, and acceptable dose limits.

It is an objective and advantage of the present invention to integrate device generated pain measurements and other biometric sensors and biopsychosocial data collected within a graphical user interface for tracking and evaluation of a patient's health status and response to treatment as the subjective nature of pain has many components that can be potentially objectified when combined with a physiological measurement of pain as acquired by the PainTrace device 14 and integrated within the PMD 10; pain measurement and diagnostic system (Chapman et al, Pain and Stress in a Systems Perspective: Reciprocal Neural, Endocrine, and Immune Interactions. J Pain. 2008 February; 9(2):122-145).

It is a further object and advantage of the present invention that the PMD utilizes a computer processing system having memory and data storage to process the electrical activity of a pain matrix and central nervous system measurement device.

It is a further object and advantage of the present invention that the PMD utilizes a computer processing system having memory and data storage to process the electrical activity of a pain matrix and central nervous system measurement device by measuring the differential of voltage or current between at least two matching electrodes and normalizing an electric signal to determine a value level representative of objective quantitative measure of pain matrix activity and displaying and storing data from the pain measurement device and using the collected data in the evaluation of health and wellness.

It is a further object and advantage of the present invention that the PMD utilizes a computer processing system having memory and data storage to process the electrical activity of a pain matrix and central nervous system measurement device by measuring the differential of voltage or current between at least two matching electrodes contralaterally placed and by measuring the voltage or current differential between and normalizing an electric signal to determine a value level representative of an objective measure of pain matrix activity and displaying and storing data from the pain measurement device and using the collected data in the evaluation of health and wellness.

It is a further object and advantage of the present invention that the PMD utilizes a computer processing system having memory and data storage to process the electrical activity of a pain matrix and central nervous system measurement device by measuring the differential of voltage or current between at least two matching electrodes ipsilaterally placed and by measuring the voltage or current differential between and normalizing an electric signal to determine a value level representative of an objective measure of pain measuring and displaying and storing data from the pain measurement device and using the collected data in the evaluation of health and wellness.

It is a further object and advantage of the present invention that the PMD utilizes a computer processing system having memory and data storage to process the electrical activity of a pain matrix and central nervous system measurement device by measuring the differential of voltage or current between at least two matching electrodes contralaterally placed with the voltage or current differential between at least two matching electrodes ipsilaterally placed to calibrate measurements of the pain matrix and central nervous system activity and displaying and storing data from the pain measurement device and using the collected data for the evaluation of health and wellness.

It is a further object and advantage of the present invention that the PMD utilizes a computer processing system having memory and data storage to process the electrical activity of a pain matrix and central nervous system measurement device by measuring the differential of voltage or current between at least two matching electrodes contralaterally placed with the voltage or current differential between at least two matching electrodes ipsilaterally placed to determine and validate a value level representative of an objective measure of pain matrix and central nervous system activity and displaying and storing data from the pain measurement device and using the collected data for the evaluation of health and wellness.

It is a further object and advantage of the present invention that the pain matrix and central nervous system measurement device of the PMD will be worn over longer periods of time as a "wearable" at-home monitor for pain and health monitoring with data collected using components and features of the PMD.

It is a further object and advantage of the present invention that the PMD provide alerts based on data collected from the pain matrix and central nervous system measurement device that deviates from set levels be transmitted to associated healthcare providers.

It is a further object and advantage of the present invention that the PMD provides for the administration of medication through an automated pump dispenser based on data collected from the pain matrix and central nervous system measurement device.

It is a further object and advantage of the present invention that the PMD provides for the activation through a security code of a dispenser for medication based on data collected from the pain matrix and central nervous system measurement device.

It is a further object and advantage of the present invention that data collected from one or more physiological monitors of the PMD for measuring multiple physiological signs of a subject such as pain, heart rate, heart rate variability, skin temperature, electrodermal activity (EDA), photoplethysmogram (PPG) readings, skin conductivity, motion, tension and compression is used for the evaluation of health and wellness of a patient.

It is a further object and advantage that the PMD of the present invention collect data from one or more physiological monitors for measuring multiple physiological signs.

It is a further objective and advantage that the PMD includes components and features to interact with the patient based on their diagnosis and monitored changes in pain levels.

The present invention is related to a bioanalytical analysis system using pain measurements to diagnosis and measure the effectiveness of treatment outcomes, the system comprising a device for measuring pain matrix activity; a plurality of BioTrace Factors related to biophysical, biological, psychological, social, environmental, and demographic information; and wherein deflections in measurements of pain matrix activity are combined with BioTrace Factors to determine the effectiveness of a patient's treatment. The combination of pain matrix activity and BioTrace Factors provides a quantitative measure of pain. The quantitative measure of pain matrix activity correlates with self-reporting of pain using a numerical rating scale. The bioanalytical analysis system comprises 10-60 messaging triggered by a combination of pain matrix activity, BioTrace Factors, and integrated journaling. The plurality of BioTrace Factors of the bioanalytical analysis system comprising contribution factors and factor impact levels. The combination of pain matrix activity measurements and BioTrace Factors provide a PainTrace Factor reflective of an individual patient's experience to pain. The combination of BioTrace Factors and a PainTrace Factor provide BioTrace Progress Score reflective of the effectiveness of a patient's treatment and measurement of a patient's compliance to that treatment.

In some embodiments measurements of pain matrix activity of the bioanalytical analysis system are made without applying a voltage, by applying a range of voltages or currents. The device for measuring pain matrix activity of the bioanalytical analysis system has sensors and in some embodiments a float current is applied to the sensors intermittently. The sensors of the device for measuring pain matrix activity may be placed contralaterally, ipsilaterally, in pairs placed contralaterally and in pairs placed ipsilaterally, and in some embodiments two pairs of ipsilateral sensors are placed contralaterally. The device for measuring pain matrix activity of the bioanalytical analysis system has a load resistor having resistance of between 0.5 k ohms and 900 k ohms. The load resistor may be a variable resistor and a calibration method may incrementally increase resistance by applying voltage to generate a linear resistance curve. The variable resistor may be adjusted using the linear resistance curve to produce maximum current flow.

The bioanalytical analysis system using pain measurements to diagnosis and measure the effectiveness of treatment outcomes may comprise a noxious stimulus caliper that applies a consistent and repeatable amount of pressure for a consistent period of time. By acquiring pain matrix activity measurements from the applied stimulus using the noxious stimulus caliper a baseline of pain tolerance may be generated. The bioanalytical analysis system may comprise one or all of the following components a motion detector, a heart rate monitor, a heart rate variability monitor, a blood pressure monitor, a galvanic skin response measurement device, and a skin temperature measurement device. In some embodiments, the device for measuring pain matrix activity of the bioanalytical analysis system comprising a pain matrix monitoring device, heart rate monitor, heart rate variability monitor, blood pressure monitor, galvanic skin response measurement device, temperature measurement device, and motion detector. The bioanalytical analysis system may comprise SaaS, PaaS and on demand computing services and a shared resource database through a web browser or other interface. The bioanalytical analysis system may comprise an electronic circuit for the initialization, identification, location, acquisition, control and communication to the device for measuring pain matrix activity.

The present invention is related to an autonomic function monitoring device, comprising: a pain matrix activity measurement device having sensors, a data acquisition system; and wherein deflections in measurements of pain matrix activity are used to determine the levels of a patient's pain and health. The pain matrix activity measurement of the autonomic function monitoring device provides a quantitative measure of pain. The quantitative measure of pain matrix activity correlates with self-reporting of pain using a numerical rating scale. The measurements of pain matrix activity may be made without applying a voltage or by applying a range of voltages and currents. In some embodiments, a float current is applied to the sensors intermittently. The sensors of the autonomic function monitoring device may be placed contralaterally, ipsilaterally, in pairs placed contralaterally and in pairs placed ipsilaterally, and in some embodiments two pairs of ipsilateral sensors may be placed contralaterally.

The autonomic function monitoring device wherein the device for measuring pain matrix activity having a load resistor having resistance of between 0.5 k ohms and 900 k ohms. In some embodiments, the load resistor is a variable resistor and resistance is incrementally increased and voltage is applied to generate a linear resistance curve. In applying calibration methods, the variable resistor may be adjusted using the linear resistance curve to produce maximum current flow. The autonomic function monitoring device may comprise a noxious stimulus caliper that applies a consistent and repeatable amount of pressure for a consistent period of time. The pain matrix activity measurements from the applied stimulus using the noxious stimulus caliper may be used to generate a baseline of pain tolerance. In some embodiments, the autonomic function monitoring device may comprise one or all of a motion detector, a heart rate monitor, a heart rate variability monitor, a blood pressure monitor, a galvanic skin response measurement device, and a skin temperature measurement device. The autonomic function monitoring device comprising SaaS, PaaS and on demand computing services and a shared resource database through a web browser or other interface. The autonomic function monitoring device comprising an electronic circuit for the initialization, identification, location, acquisition, control and communication to a plurality of sensors.

The present invention is related to an activity monitor to measure pain, that in some embodiments may comprise contralateral sensors measuring pain matrix activity without applying voltage. In other embodiments, activity monitor to measure pain may comprise ipsilateral sensors by applying voltage. The activity monitor to measure pain comprising one or all of a heart rate monitor, a heart rate variability monitor, a motion detector, a blood pressure monitor, a galvanic skin response measurement device, and a skin temperature measurement device. The activity monitor to measure pain may comprise a sensor track. The activity monitor to measure pain may comprise a sensor cluster. The activity monitor to measure pain may comprise an electronic circuit for the initialization, identification, location, acquisition, control and communication to a plurality of sensors.

The present invention is further related to a sensor track, comprising a flexible sensor attachment device having a track and conductive strip; and wherein the flexible sensor attachment device provides for the attachment and electrical connection to a plurality of electrodes and sensors. The sensor track may comprise a Velcro strip for the attachment of the sensor track to clothing. The sensor track may comprise an adhesive strip for the attachment of the sensor track to skin, clothing or other surfaces. The sensor track may comprise an electronic circuit for the initialization, identification, location, acquisition, control and communication to a plurality of sensors. The sensor track may comprise wireless communication circuitry. The sensor track may comprise communication connectors to add separate sensor tracks and additional electrodes and sensors to the sensor track.

The present invention is related to a method of quantitatively measuring pain, comprising establishing a baseline by measuring the pain matrix activity during noxious stimulus; monitoring pain matrix activity and deflections from the established baseline; establishing BioTrace Factors based on patient biophysical data, patient and population demographics and self-reported measurements of pain; establishing a PainTrace Factor based on the integration of data from pain matrix activity measurements and BioTrace Factors; monitoring patient pain matrix activity through treatment; and identifying pre-treatment and post-treatment deltas indicative of the change in pain state; and correlating the measured deltas with associated pain scales.

The present invention is a method of measuring the effectiveness of treatment outcomes using measurements of pain matrix activity, comprising monitoring pain matrix activity and deflections to establish a quantitative measure of pain; monitoring and collecting LifeTraceIT data based on patient activity, engagement, compliance and integrated journaling; applying an iterative analysis to BioTrace Factors, PainTrace Factors, LifeTraceIT data, related to a patient and integrating this analysis to generate an individualized BioTrace Progress Score which will be determined on an ongoing basis that continues monitoring of patient actions, physiological data, treatment interventions, and pain matrix activity; which will further be combined with associated trends, population clusters, current research and historical medical records in assessing the effectiveness of treatment outcomes.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

BRIEF DESCRIPTION OF THE DRAWINGS

Several embodiments of the present invention will now be described by way of example only, with reference to the accompanying drawings in which:

FIG. 6G is a diagrammatic representation of a still further embodiment of a PainTrace measurement device with sensors that provides data to an embodiment of the PainTrace application component in an embodiment of the PMD of the present invention;

FIG. 6H is a diagrammatic representation of the still further embodiment of a PainTrace measurement device with sensors of FIG. 6G that provides data to an embodiment of the PainTrace application component in an embodiment of the PMD of the present invention;

FIG. 6I is a diagrammatic representation of a still further embodiment of a PainTrace measurement device with sensor integrated with a blood pressure monitor to provide data to an embodiment of the PainTrace application component in an embodiment of the PMD of the present invention;

FIG. 6J is a diagrammatic representation of a still further embodiment of a PainTrace sensor device that may be used with the PainTrace measurement device and blood pressure monitor of FIG. 6I to provide data to an embodiment of the PainTrace application component in an embodiment of the PMD of the present invention;

FIG. 7A is a front view of a diagrammatic representation of an embodiment of the PainTrace device with sensor installed on a wristband to provide data to an embodiment of the PainTrace application component in an embodiment of the PMD of the present invention;

FIG. 7B is a rear view of a diagrammatic representation of an embodiment of the PainTrace device with sensor installed on a wristband to provide data to an embodiment of the PainTrace application component in an embodiment of the PMD of the present invention;

FIG. 7C is a front view of a diagrammatic representation of another embodiment of only the PainTrace sensor installed on a wristband to provide data to an embodiment of the PainTrace application component in an embodiment of the PMD of the present invention;

FIG. 8A is a side view of a diagrammatic representation of an embodiment of the PainTrace device with sensors to provide data to an embodiment of the PainTrace application component in an embodiment of the PMD of the present invention;

FIG. 8B is a rear view of a diagrammatic representation of an embodiment of the PainTrace device with sensor installed on a wristband to provide data to an embodiment of the PainTrace application component in an embodiment of the PMD of the present invention;

FIG. 9A is an internal side view of a diagrammatic representation of an embodiment of the PainTrace device with sensor to provide data to an embodiment of the PainTrace application component in an embodiment of the PMD of the present invention;

FIG. 9B is a rear view of a diagrammatic representation of an embodiment of the PainTrace device of FIG. 9A to provide data to an embodiment of the PainTrace application component in an embodiment of the PMD of the present invention;

FIG. 9C is a rear view of a diagrammatic representation of an embodiment of the PainTrace sensor of FIG. 9A to provide data to an embodiment of the PainTrace application component in an embodiment of the PMD of the present invention;

FIG. 10A is a perspective view of a diagrammatic representation of an embodiment of the PainTrace sensor to provide data to an embodiment of the PainTrace application component in an embodiment of the PMD of the present invention;

FIG. 10B is a perspective view of a diagrammatic representation of an embodiment of the PainTrace sensor connector;

FIG. 10C is a perspective view of a diagrammatic representation of an embodiment of the PainTrace device connector;

FIG. 11A is a perspective view of a diagrammatic representation of an embodiment of the PainTrace sensor, sensor connector, and device connector in an unlocked position;

FIG. 11B is a perspective view of a diagrammatic representation of an embodiment of the PainTrace sensor, sensor connector, and device connector in a locked position;

FIG. 23 is example PainTrace data showing pain measurements before and after treatment in an embodiment of the PMD of the present invention;

DETAILED DESCRIPTION OF THE INVENTION

Figure 1:
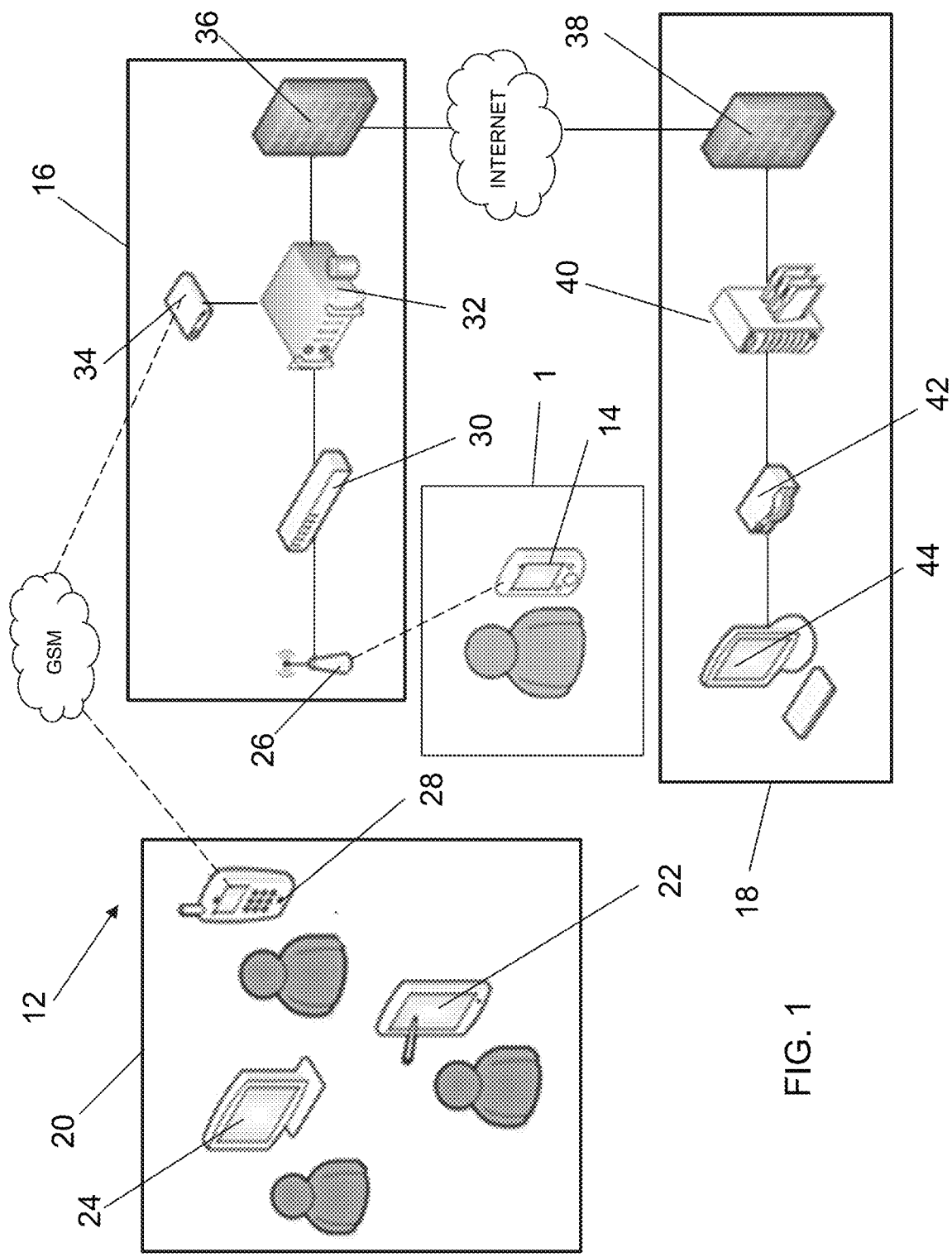
FIG. 1 is a diagrammatic representation of an embodiment of a pain measurement and diagnostic system (PMD) network that may be in a clinical or hospital setting in an implementation of the present invention.

The present invention is a pain matrix and central nervous system measurement and diagnostic system (PMD) 10 that includes one or more medical devices for the objective measurement of pain matrix activity and a method of data collection and analysis of pain measurements to diagnose disease states and health status and validate patient treatments and outcomes. The PMD 10 may be implemented on local network and other devices having compatible electronics. The computer systems and electronic devices are integrated within networks and servers to communicate with one or more pain matrix and central nervous system measurement devices, biosensors, computer systems, devices and communication systems. In a first embodiment as shown in FIG. 1, the PMD 10 may be implemented within a local area network 12 for example may be within a clinical or hospital environment or utilizing electronic devices capable of communicating with cloud computing services for personal or remote monitoring. The PMD 10 may be implemented through one or more devices such as a smartphone to collect and transmit patient data to a cloud network, hospital network, medical offices, assisted living, or other point of care or place for acquiring, viewing, and analyzing biophysical data, or for telemedicine each referred to herein as an "acquisition environment" 1 and to an external BioTraceIT PMD server system 18 to be accessible to compile, review and store patient data and biometric information. The PMD 10 may provide various levels of access to medical devices and specific components and features that may be implemented through one or more software applications. Administrative levels may be set and managed within administrative tools of the software application. Software application variants and access levels provide for medical devices, features and components to be specific to particular facets of treatment and to the patient and medical professionals treating the patient. For example, within the acquisition environment 1, the PMD 10 may provide features and components accessible by the patient for personal patient monitoring of biophysical factors and activities. Additional, features and components may be provided for health care providers (HCPs) for point of care monitoring and additional features for physicians and others for remote telemedicine monitoring with levels or security and patient anonymity provided as required within the different levels of access. Within the "acquisition environment" 1, the devices and sensors collecting patient data may have internal communication systems to display and transmit data within the PMD 10 that may be accessible through an intranet and/or internet connection for viewing and monitoring collected patient data on a mobile device such as a smartphone, smartwatch iPhone, iPad, iPod, smartwatch, wearable, augmented reality glasses, or tablet computer 22 for the patient to access the data themselves and/or for an HCP, physician, physical therapist or other attendants of the patient, or payers, administration, or independent researchers to access the data.

The PMD 10 may be implemented through a secure server and be accessible through a web browser user interface for hospital HCP staff to register and collect data from the sensors and data collection devices within a hospital network 16. Within a hospital network firewalls 36, redundancy and other security protocols to protect patient data are available with networking hubs 30, servers 32, and communication devices 34 to establish communications to the acquisition environment 1 and to distribute data through a communication network 20 to the HCPs and others requiring the patient data. The communication network 20 may include the access to the patient data through the PMD 10 on tablet computers 22, nursing station dashboards 24, smartphones 28, and through other devices within the communications network 20.

Access to the patient data through the PMD 10 may further be provided through devices directly wired and connected to the pain matrix and central nervous system measurement or other biosensors for data collection such as through a USB port for acquisition environments 1 that may be remote for internet access. For example, in a battlefield medical unit that requires patient data and analysis without having access to external resources. The patient data may further be stored on the device such as on memory and data storage devices on a PainTrace device 14 to be transmitted when wired or wireless access becomes available. The PMD 10 may further be pre-loaded to be the only accessible application and monitoring system on a digital device for patient, HCP, or physician use in environments without internet access, such as for an elderly patient within their home in a remote location. Data from the PMD 10 using the digital devices may be linked through analog phone lines or cellular communications 26 to provide communication to HCPs and others in the form of alerts, voicemail, text, and/or email. Abbreviated data and information may also be accessible through the PMD 10 via software applications or specific components and features of one or more software applications accessible on a smartphone through cellular communications 26. Therefore, accessibility to the patient data through the PMD 10 is provided in a number of forms to accommodate various acquisition environments 1 where the patient may be infirmed within a hospital, be within a care or rehabilitation facility, be within their own home, and/or be in remote locations with minimal or no access to the internet. In this way, the PMD 10 may provide the collected data that may be from the one or more pain matrix and central nervous system measurement devices 14 and biosensors 11 in an accessible and comprehensive manner to provide useable and interpretable information to the patient, HCPs and physician at each of the different accessible levels of PMD's software application and hardware data acquisition components and features.

The sensors and devices integrated with the components and features of the PMD 10 may importantly be in the form of the pain matrix and central nervous system measurement sensors and devices referred to herein as PainTrace devices 14. The PainTrace devices 14 may collect and display data within the device 14 and transmit data within the acquisition environment 1 and within the hospital network 16 and other networks preferably using Bluetooth, Wi-Fi, Near Field Communication (NFC) and/or other communication protocols such as through wireless modems where sensor data is collected and recorded from patients within the acquisition environment 1.

The collected data may further be transmitted through a secure internet connection to the BioTraceIT PMD server system 18 that also has firewalls 38, redundancy and security protocols to protect data. The data may preferably be transmitted either directly from a pain matrix and central nervous system measurement device or other sensors or from a clinical or hospital network without identifying information such as the name or address of the patient. However, information about the patient that may include biological, psychological, social, and environmental factors may be included and all data including patient identifying information may be immediately accessible to assist with treatment within the acquisition environment 1 at the point of care. In this manner all data may be accessible within the hospital network 16 and de-identified information can be correlated and stored within a database and may be accessible through the BioTraceIT PMD server system 18 as raw or processed data from sensors including the PainTrace device 14 with collection times and dates to be used with the biological, psychological, social, and environmental factors where data of all types may be available for data mining, correlation and pattern analysis to identify and develop BioTrace factors as described herein. The BioTraceIT PMD server system 18 also has a server 40, network hubs 42 and computer systems 44. The BioTraceIT PMD server 18 may also host firmware images for updates to the software components and features of the PMD 10. Through some applications of the PMD system 10 as described herein, data may only be accessible through a direct wire connection such as using a USB connection to the pain matrix and central nervous system measurement device or through a near field communication (NFC) in order to provide limited access and secure an autonomous device such as a drug dispenser or devices within remote acquisition environment without internet access.

Figure 2:
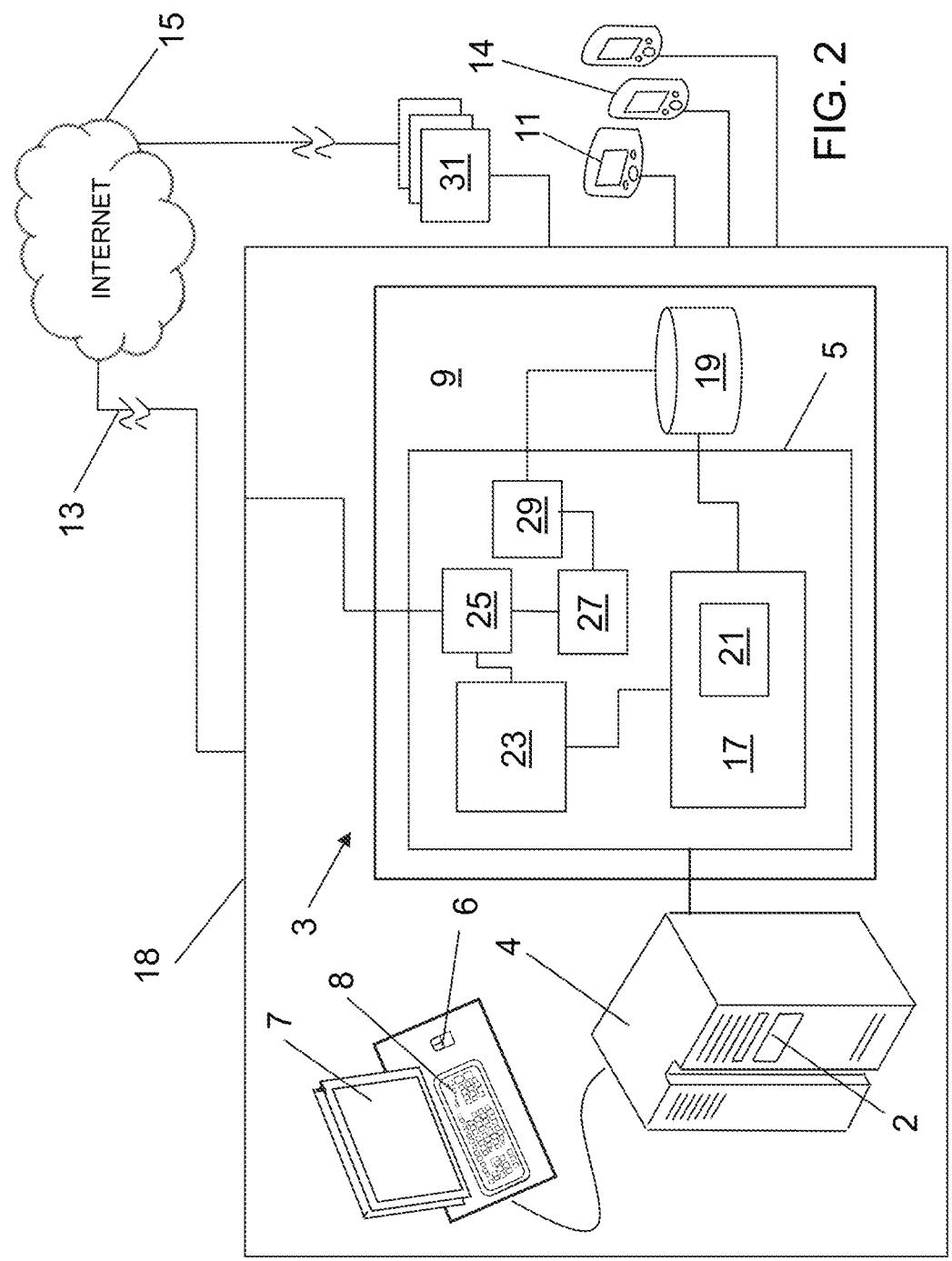
FIG. 2 is a diagrammatic representation of an embodiment of a server system and integration of one or more server systems, computers, mobile devices, biophysical devices and sensors and pain measurement devices within the PMD network in an implementation of the present invention.

As shown in FIG. 2, the PMD system 10 may be implemented in computer hardware and computerized equipment.

For example, components and features of the PMD system 10 can be performed using one or more pain matrix and central nervous system measurement devices 14 and/or other biosensor medical device systems 11 to measure biophysical readings such as heart rate, heart rate variability, photoplethysmogram (PPG), blood pressure, skin temperature, movement, GSR, and other vital signs. The PMD 10 may further be implemented through other digital communications devices and/or one or more personal computers and data servers. For example, components and features of the PMD 10 and BioTraceIT server system 18 may be implemented on a computer system 3 which is shown for the purpose of illustrating an embodiment of hardware components that may be used for implementation of the PMD 10. The present invention is not limited to the computer system 3, software or hardware components shown, but may be used with any electronic data processing system such as found in personal or other digital communications devices, cellular phones and other mobile or wearable devices, tablet computers, or any other systems for the acquisition, processing, transformation, display and distribution of analog and digital data. The computer system 3 includes a server computer 4 having a microprocessor-based unit 5 (also referred to herein as a processor) for receiving and processing software programs and for performing other processing functions. An output device 7 such as a visual display is electrically connected to the processor unit 5 for displaying user-related information associated with the software, e.g., by means of a graphical user interface. A keyboard 8 may also be connected to the processor unit 5 for permitting a user to input information to a software program. In addition to using the keyboard 8 for input, a mouse 6 may be used for moving a selector on the display 7 and graphical user interface, or alternatively a touch screen of a smartphone, smartwatch iPhone, iPad, iPod, wearable, augmented reality glasses, or tablet computer, or any other input device may be provided for choosing an item and providing input to the processor 5. The pain measurement devices which in some embodiments may be referred to herein as the PainTrace devices 14 and other biophysical devices and sensors 11 are integrated with components and features of the PMD 10 which may be in the form of software and/or hardware. These feature and components of the PMD 10 as described herein may initialize communication to electrodes and sensors and setup communication protocols to one or more PainTrace devices 14 and other biophysical devices and sensors 11 to provide instructions in the form of starting, stopping, setting and adjusting the time, sampling rates, and other parameters of data acquisition. The PMD 10 may also associate the PainTrace devices 14 and other biophysical devices and sensors 11 with a patient, treatment protocol, one or more HCPs and/or physicians, a clinical or hospital network, and other associative information related to the patient, treatment, and acquired data as described herein. Within the PMD 10, PainTrace devices 14 and other biophysical devices and sensors 11 may be automatically located and identified through these associations to assist an HCP and clearly present acquired data as being from a specific patient in accordance with appropriate healthcare guidelines. The components and features of the PMD 10 may also set alerts and alarms with specific contact information to directly contact the HCP or physician in the case of an emergency, access a PainTrace device 14 and other biophysical devices and sensors 11 to replace or reset values, and provide tracking of the frequency of pain matrix and central nervous system measurements or other sensor readings. Various components and features of the PMD 10 are accessible from the pain measurement device 14, from other biophysical sensors 11, from a tablet computer or smartphone used by the HCP or physician, and/or through the network or server system as described herein. For example, a HCP who is on call may receive an alert and could adjust the frequency of readings to acquire more data from the pain measurement device via their smartphone under acceptable conditions and security within the acquisition environment 1 and network 16. It is to be appreciated that the input is not limited to the known input apparatus and methods but includes input methods and devices which may yet be developed.

Memory and data storage, in any form, can be included and is illustrated as a hard-disk device such as computer readable storage medium 2, which can include software programs, and is connected to the microprocessor based unit 5 for providing a means of inputting the software programs and other information to the microprocessor based unit 5. Multiple types of memory can also be provided and data can be written to any suitable type of memory. Memory can be external and accessible using a wired or wireless connection, either directly or via a local or large area network, such as the Internet. Still further, the processor unit 5 may be programmed, as is well known in the art, for storing the software program internally. The output device 7 provides visually to the user transactional, interactive or variable data that has been subject to transformations. The output device 7 can be a monitor, touch screen or other visual computer or digital device screen or graphical user interface (GUI), a chart recorder, a printer or other output device that provides a visual or other representation of a final output from the processor unit 5. The output device 7 can also be an output device in the form of a data collection device such as a pain matrix and central nervous system measurement device or other biosensor medical device system that provides the transactional data as an analog or digital output and/or as a digital file. The processor unit 5 provides means for processing and transforming the transactional, interactive or variable data to produce readily discernible, informational and organized images and data on the intended output device or media. Those skilled in the art will recognize that the present invention is not limited to just these mentioned data processing and data transformation functions.

The server computer 4 can store a computer program product having a program stored in the computer readable storage medium 2, which may include, for example: magnetic storage media such as a magnetic disk or magnetic tape; optical storage media such as an optical disc, optical tape, or machine readable bar code; solid state electronic storage devices such as random access memory (RAM), read only memory (ROM) or flash memory data storage devices. The associated computer program and data server may be implemented through application software 17 on a SaaS (Software as a Service), PaaS (Platform as a Service) or on demand computing service such as a Cloud or shared resource database through a web browser or other interface. Secure logins with passwords may be provided to remotely access the different levels of software 17 through an intranet or internet connection 13. One or more of the devices to access the PMD system 10 may be connected wirelessly, such as by a cellular link, Wi-Fi wireless, Bluetooth technology or other technology where the device is either directly connected or via a network. It is to be appreciated that such devices can be mobile devices using voice commands to enter and access data using digital devices that may be in the form of a camera, PDA, iPod, iPhone, iPad, tablet computer, augmented reality glasses, digital display, smartphone, or cell phone, smartwatch, wearable, and other digital devices that can be used as a processing unit, data transformation unit, a display unit, or a unit to give processing instructions, and as a service offered via the internet.

The PMD 10 implemented within the BioTraceIT PMD server system 18 may in an embodiment have security protocols 9, one or more databases 19, an administrative tool module 21, data acquisition module 23 to accept and transform data from a pain matrix and central nervous system measurement device or other sensor data, a communications module 25 to collect and transmit data which may be in the form of emails, text messaging, voice messaging and other communication protocols, a data analysis module 27, and data compilation module 29. The BioTraceIT PMD server system 18 may acquire, compile and store data from multiple pain matrix and central nervous system measurement devices and other sensors within various acquisition environments 1 such as one or more networks that may include a hospital network 16 and in-home monitoring of patients. The BioTraceIT PMD server system 18 further provides for the transmission, collection and storage of reference data 31 through an intranet or internet connection as shown in FIG. 2. The PMD 10 through the communication module 25 may further provide software and firmware updates and reference updates to maintain the most currently available information for HCPs and other users of the PMD 10.

The PMD 10 may be implemented as a mobile application for an iPhone, iPad, iPod, smartphone, smartwatch, wearable, augmented reality glasses, tablet computer, and/or other mobile digital device. The PMD 10 may further be developed on a computer operating system to be implemented within the system servers 32 of the hospital network 16 for example as a nursing station dashboard application 24, running on a Windows-based computer system. In any format, the PMD 10 provides for the Health Care Providers (HCP) to select a pain matrix and central nervous system measurement device such as the PainTrace device 14 or other sensor or medical device 11, and correlate the sensor data with patient information, as well as monitor the collected data, and receive threshold-based alerts. In one embodiment, the PMD 10 may communicate solely within the hospital server system 16 in order to optimize refresh times for data storage and for receiving updates from the centralized server source 16. The collected data may then be compressed and transmitted to the external BioTraceIT PMD server system 18 at repeated intervals, to reduce required bandwidth and transmission time. In further embodiments, the PMD 10 including one or more pain matrix and central nervous system measurement devices 14 or other biosensors 11 may be implemented on a mobile device for patients to monitor individual health readings.

Figure 3:
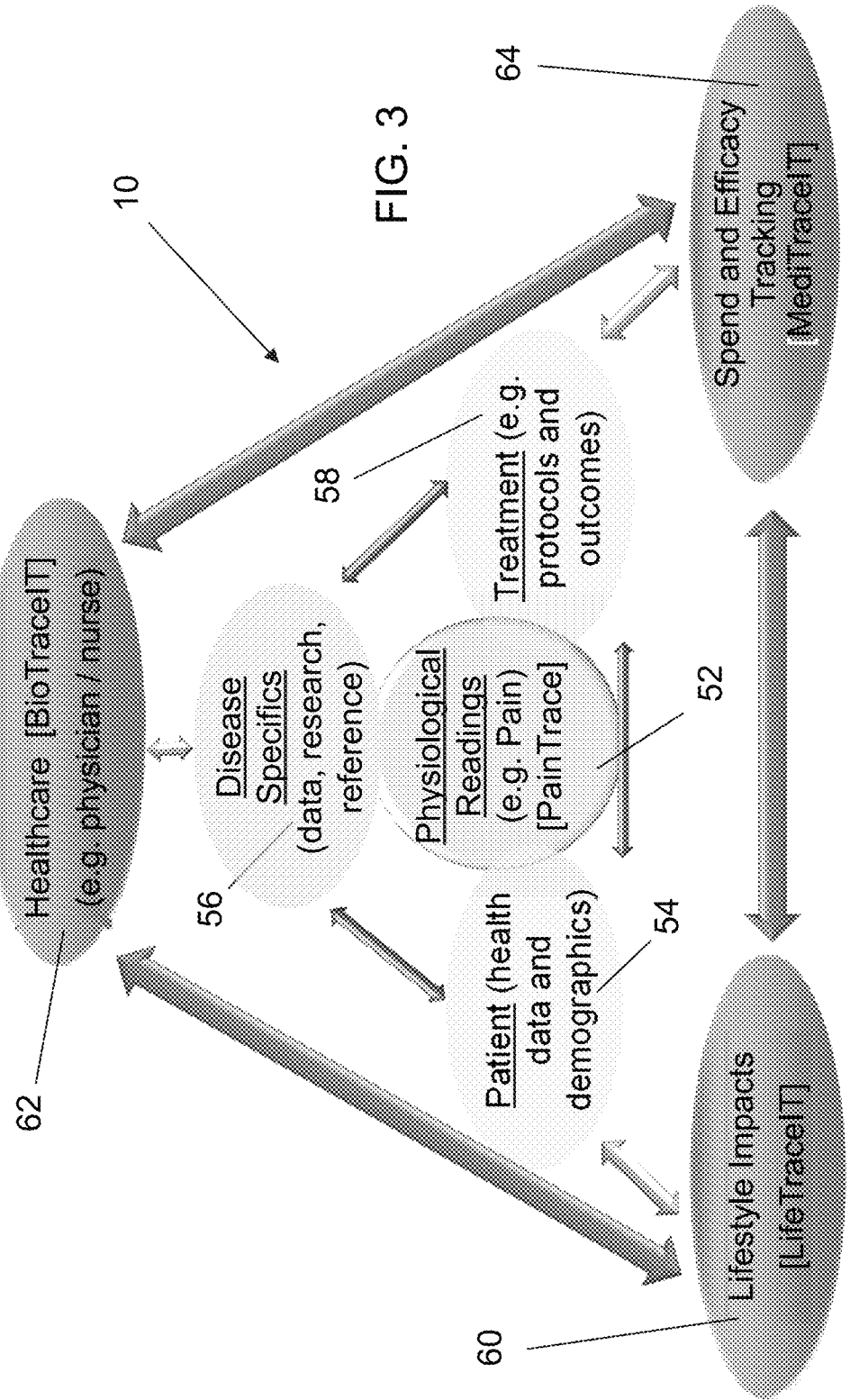
FIG. 3 is a diagrammatic representation of an embodiment of application components in an embodiment of the PMD of the present invention.

As shown in FIG. 3, the diagram represents the different components and features of software applications and hardware in the form of data acquisition devices of the PMD some or all of which may be included in various forms of the PMD 10 that may be used by patients, healthcare providers, insurance providers, hospital administration, and others. The components and type of data contained within each component as described herein is provided with a general context and application of the data. The data acquisition module 23 of the PMD 10 is essentially a core Physiological Readings component 52 to collect data from pain matrix and central nervous system measurement devices such as the PainTrace device 14 and to collect other sensor data used for analysis within the PMD 10. This data is collected and combined with a "Patient" health data component 54 and demographics of patient populations referred to as a "Disease Specifics" component 56 including research, factors affecting pain perception, acute and chronic disease states and references. Components and features within the PMD 10 may further provide a "Treatment" component 58 presenting protocols and outcomes of prescribed treatments. In an embodiment, the PMD 10 combines the physiological readings, in this instance related to measurement of the pain matrix and central nervous system, with pertinent data related to but not limited to the research and data analysis components, to produce "objective pain readings" and evaluate pain matrix and central nervous system measurement readings with respect to patient biophysical factors, diagnoses, specific data field input, and treatments.

The Physiological Readings component 52 acquires data that includes the measured pain matrix and central nervous system data acquired by PainTrace device 14 and other sensor oriented readings related to the body's reaction to stress, disease, and health-related experience. The Patient data component 54 provides data in the form of biologic data related to specifics about patient age, health, and medical history that may include but not be limited to biological, psychological, social, and environmental factors. This data may be provided or supplemented by the patient as part of their integration to treatment and additionally be pulled from electronic health records, notes, and other data acquired regarding a patient. Patient data when transferred to the BioTraceIT PMD server system 18 may be de-identified per appropriate healthcare guidelines. Using the data analysis module 27, collected data, such as data collected from the PainTrace device 14 and other biosensors 11, may be normalized, averaged, and correlated to specific activities, foods, exercise and other biophysical actions of the patient. Components and features of the PMD 10 utilize and combine the transformed collected data with physiological measures, and biological, psychological, social, and environmental factors to develop bioclustering matrices, and bipartite graphs that using weighting algorithms are correlated and ranked to develop what are referred to herein as BioTrace Factors 150. By transforming and correlating raw data, which is innately subjective, objective physiological measures are generated and data from the PainTrace device 14 and pain matrix and central nervous system measurement and diagnostic technique becomes increasingly meaningful and may be used to evaluate a patient's perception and tolerance of pain to improve proper diagnosis and treatment.

To further standardize physiological response to pain and subsequent pain matrix and central nervous system measurement using the PainTrace device 14 within the PMD 10, an adjunct device that delivers a standardized noxious stimulus is integrated into the PMD 10 and the diagnostic technique. The introduction of painful, or noxious, stimulus based on current central stimuli tests such as the supraorbital pressure or sternal rub, or peripheral tests such as squeezing the lunula area of the finger or toe nail, or squeezing the side of the finger will be repeatable and measurable through the use of calibers and compression and tension gauges to apply stimulus with consistent and repeatable amount of pressure to standardize the applied stimulus. Stimulus will be applied over a standardized time while measuring patient pain levels, or pain matrix activity, pre-, intra-, and post-stimulus. "Standard stimuli response" may be measured during periods of health, such as an annual visit, or during injury or illness to establish baseline "pain matrix response levels". Patient pain matrix activity will then be applied to standardized scales to be used with other factors to create a PainTrace Factor which references this baseline pain matrix activity. The pain matrix response levels are further cross-referenced to other known factors that influence a patient's tolerance to pain which include but are not limited to age, sex, race, blood pressure, previous injury, pain surveys, and with additional physiological and psychosocial that individualize measurements which may be some of the components that are referred to herein as BioTrace Factors 150. The contribution of these factors with the patient's baseline pain matrix activity measured using noxious stimuli are used to derive the patient's personal PainTrace Factor.

The pain matrix and central nervous system measurement data and BioTrace Factors 150 may further be implemented within the Treatment component 58 of the PMD 10 to track and measure the objective physiological measures as related to treatment protocols and outcomes. Connecting treatments and comparing physiological readings related to treatments may result in better understanding of how effective each treatment is and additionally since it is also related to patient data provided within the Patient component 54 there is the opportunity to specialize and individualize treatment options for the individual patient. Furthermore, analyzing and connecting treatment, patient demographics, and acute and chronic disease states may not only produce improvements in individualized care but also provide a broader knowledge of disease states resulting in more effective care for all patients and associated costs savings.

A broader knowledge of the efficacy of treatments from the collection of physiological readings during treatment and the integration and analysis of this data as it relates to reference materials 31 is provided using the Disease Specifics component 56. This component of the PMD 10 may integrate knowledge on specific acute and chronic ailments and diseases with information related to the BioTrace Factors 150 of a specific patient to provide for more meaningful understanding of physiological readings in multi-factorial disease states, such as the perception of pain. In addition, this data curated from biomedical, healthcare, clinical, and physiological research can be referenced by appropriate end-users, such as healthcare practitioners, to both educate and make resources available to medical personnel. The derived Biotrace Factor demographics may be grouped in major categories (bio, psycho, social, environmental, behavioral, etc.) deemed relevant based on patient data. The development and ranking of the BioTrace Factors 150 may continually and iteratively be updated through the integration of information on disease states and treatments in reference materials 31 and can be cross-referenced using the data compilation module 29 of the PMD 10 generating trends and potential improvements in care. Clinical trial data can additionally be linked using the components and features of the PMD 10 to create a greater connection between research, outcomes, and potential new treatments.

Using the Physiological Readings component 52 with the Patient component 54, the Disease Specific component 56, and Treatment component 58 information will not only generate normalized, correlative, objective measures of primarily subjective symptoms but furthermore may be connected with patient self-reported, and sensor monitored, lifestyle impacts software applications referred to herein as the LifeTraceIT component 60 of the PMD 10; healthcare practitioner software and applications referred to as the BioTraceIT component 62 of the PMD 10 to assist in decision making for testing, diagnosis and treatment; and the financial impact of treatment through spend and efficacy tracking referred to herein as the MediTraceIT 64 of the PMD 10 to create a comprehensive system for integrating the many factors that impact a subjective physiological experience of patients. Transformed data may be utilized to create patient specific electronic communications such as through text messaging, via dedicated or other mobile devices, to engage the patient to potentially evaluate sources of pain matrix inflections, and generate patient engagement to educate, encourage healthy habits and behaviors, and track activity as it relates to device generated physical data. Changes in pain levels may trigger a series of questions. This feature of the LifeTraceIT software 60 would represent "integrated journaling" which uses physiological questions based on biosignal date to request specific information from the affected individual to aid in source detection of pain or unhealthy stimulus. The LifeTraceIT 60 software application as a component of the PMD 10 uses transformed data combined with defined patient interaction platforms to engage patients.

The healthcare BioTraceIT component 62 of the PMD 10 generates normative and BioTrace Factors data for the healthcare practitioner and will promote improved understanding of a patient's experience, and an increased ability to evaluate treatment efficacy. The BioTraceIT component 62 within the PMD 10 may benefit a patient during emergent care where the measure of pain matrix and central nervous system data or PainTrace data may indicate the degree and the location of pain through an analysis of data using components and features of the PMD 10 during examination protocols. The BioTraceIT component 62 may further benefit physicians, nurses, physical therapists and others by providing patient metrics to give insight into the patient profile, contributing factors, comorbidities, and then associate relevance of these factors as it relates to the patient's experience and provide associated treatment algorithms and clinical data for consideration by the HCP.

The LifeTraceIT component 60 of the PMD 10 may optionally also be provided and accessible on the PainTrace device 14 and/or other medical devices at a patient level of access and/or through a mobile digital device software app. A patient may first provide health information through certain surveys and data forms for healthcare and health institutions utilizing the PMD 10 and/or PainTrace sensor 14 and other medical sensors and devices. During the process of completing and entering healthcare survey data or specific fields a patient may also be offered the opportunity to utilize the LifeTraceIT component as personal health record software. The LifeTraceIT component 60 of the PMD 10 may be provided in several interface modes to the subscriber such as the following:

Personal Lifestyle Tracking Component—The LifeTraceIT component 60 may be used to log activities, physiologic measures, treatment, prescription drug use, and other patient related data. The LifeTraceIT component 60 may collect data acquired using the PainTrace device 14 and other physiological measurement sensors, and collect data related to time spent in exercise, sleep, nutrition, and other activities and to collect emotional data to help a patient track and use their own LifeTraceIT data to develop and improve treatments.

Healthcare Network Component—the personal data collected from the patient noted above may additionally be connected with preferred healthcare providers, hospital systems, and networks including the BioTraceIT PMD server system 18. Ultimately, the patient is improving their opportunity to regain health and understand their physiological symptoms by sharing their personal data with healthcare providers. By utilizing this data within the BioTraceIT software component 62 data analysis may lead to the ability for an HCP to better evaluate the efficacy of treatment options, lifestyle options, and personal choices to improve both personal, and global health and disease related outcomes. This data may further be used by the healthcare community to improve understanding of treatment, lifestyle, and demographic factors to create optimized healthcare interventions with specialized focus.

Guidance and Messaging Component—Additionally, the LifeTraceIT component 60 may also provide suggestions and information to help the patient during treatment. The LifeTraceIT component 60 of the PMD 10 may gather data from other health tracking software applications a user may choose to use and with the appropriate licensing, that data will be incorporated into LifeTraceIT and BioTraceIT. The data may be integrated with other information and collected data within the PMD 10 to help the patient adapt and change routine and behavior patterns within and as required by the prescribed treatment. The LifeTraceIT component 60 may also provide for customized messaging to be created and used as messaging patterns by a doctor, HCP or other provider to provide to a patient to motivate, answer questions and relieve anxiety as behavioral patterns of the patient change. For example, to improve outcomes of chronic pain patients an "interaction algorithm based on device acquired physiological data may generate a messaging pattern to help the patient improve decision making around the use of pain prescriptions and triggers to influence coping mechanisms to address pain non-pharmacologically. Physicians may choose to initiate treatment oriented messaging patterns to make accessible to the patient over a prescribed period of time, such as through a daily message or at specific times such as when administering medication. A pain inflection may trigger the "10-60 pattern" which utilizes 10 questions about the last 60 minutes to determine source, motivation, or intervention related data. The messaging may also include changes in BioTrace Factors 150 as described herein that have resulted as an example in decreased pain in order to motivate and show the value of the collected data and of maintaining the requirements of the prescribed treatment. Alternatively, pain or other biophysical measurements by the PMD 10 may trigger alerts that prompt messaging or questions for the patient such as when pain thresholds are elevated due to for example a migraine. The LifeTraceIT software, or a device associated with the PMD 10, would initiate "10-60 Messaging" to engage the patient to determine the source of the pain at the time of pain inflection. Because migraines may be triggered by food, clothing dyes, perfumes and other chemicals, a text message is sent from the PMD 10 asking questions about the environment, activity or what food was recently consumed, for example 10 questions to receive information about the last 60 minutes. The response would be collected and evaluated to assist in determining what may be causing the elevation in pain. For example, the patient answers that they had a meal recently and they select from a list of foods that they ate or enter an alternative food entry if not included on the list. They are asked: the location; what kind of seating—i.e. a chair with a back or a stool without a back are options; were they indoors or outdoors; if outdoor were they near vegetation and what type; was there a beverage—if so was it alcohol, soda etc. The list is defined by disease state or injury to determine a source of the pain inflection detected by the Pain Measurement device 14 within the specific period of time when an elevated pain measurement is measured. The responses from the 10-60 questions are integrated into the PMD 10 and then combined with the LifeTraceIT software application to transform a physiological symptom into a diagnostic and tracking tool. Other "10-60 Messaging" scenarios may include patient engagement, education, and compliance among others.

Any prescribed medical test and/or treatment is associated with costs, to patient, the hospital, and to insurance providers with current methodologies within the healthcare system resulting in disconnects through complicated coding and coding subsets that must be entered for each step of treatment. Integration of the PMD 10 with electronic health records can eliminate duplicated work and augment the use of codes. For large hospitals, a completely different set of personnel from the HCP may enter the treatment codes that generate bills to patients and insurance companies. While financial considerations should not limit or restrict treatments offered to patients, additional knowledge on duration and efficacy of treatments and the related costs can more quickly lead to the modification of ineffective treatments. The MediTraceIT component 64 of the PMD 10 integrates health records and tracks the treatment and medications prescribed for each patient. This information is clearly presented to physicians, HCPs and others with a timescale minimizing workload and reducing duplication and errors. Within the MediTraceIT component features to adding coding and annotation to treatment are provided so that billing specific to the treatment received may be tabulated. The PMD 10 further provides within the effective and clear summary of the combination of treatments prescribed to a patient their relative effectiveness and cost to assist an HCP with identifying best treatment options, optimize costs, and furthermore help to identify abuse of medication by a patient. The PMD 10 provides the MediTraceIT component 64 as a spend and efficacy tracking system that combines healthcare analysis from the BioTraceIT component 62 with physiological measurements from collected data from sensors and related lifestyle information from the LifeTraceIT component 60. By tracking healthcare outcomes, treatment options, effectiveness, and costs the MediTraceIT component 64 of the PMD 10 allows health networks, hospitals, providers, and payors to analyze best treatment options. Additionally, with the LifeTraceIT component 60 insurance premium refunds could be realized by rewarding compliant patients for following evidence-based protocols with documented outcomes. Using the "MediTraceIT Treatment Protocols", meaning those with statistical correlation between treatment and outcome, a patient's compliance via self-report compared to treatment regimen and outcomes can be calculated for significance (meaning the patient actually did what they are instructed to do resulting in an effective outcome) and subsequently the patient would receive a refund of a stipulated portion of their insurance premium. The MediTraceIT component 64 of the PMD 10 may therefore provide a method to motivate patient compliance and subsequently drive down healthcare costs by improving outcomes.

Figure 4:
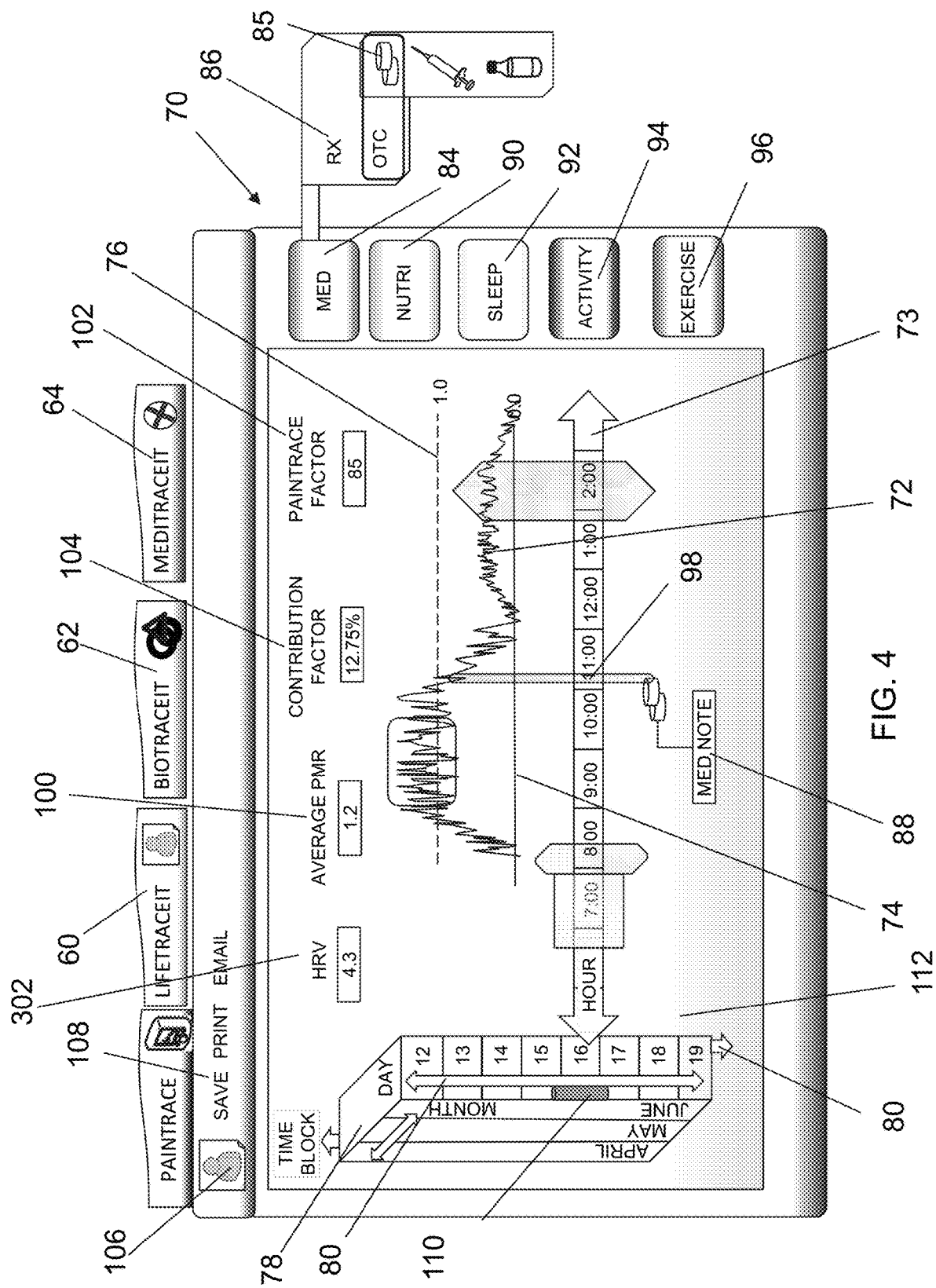
FIG. 4 is a diagrammatic representation of an embodiment of the PainTrace application component in an embodiment of the PMD of the present invention.

In an embodiment of the present invention as shown in FIG. 4, a data acquisition module 23 of the PMD 10 is the PainTrace application 70 interface for the presentation and analysis of data acquired from the PainTrace device 14 and biophysical devices and sensors 11. The PainTrace device 14 as a component of the PMD system 10 provides the measurement and integration of sensor data which may be in the form of biosignals, to analyze pain matrix activity. The PainTrace application 70 includes remote and embedded PMD circuitry that provides the control of the acquisition, communication and management of one or more PainTrace devices and/or biophysical devices and sensors 11. The PainTrace application 70 further includes location and proximity features to automatically locate, initialize, track and associated electrodes, the PainTrace device 14, and other medical devices 11 with a specific patient, HCP, physician, clinical or hospital network. The PainTrace application allows an HCP to view the PainTrace readings of the pain matrix and central nervous system and parasympathetic nervous system's activity as it relates to pain, health, and treatment with as desired other collected biophysical data. Data from the PainTrace sensor 14 and/or biophysical devices and sensors 11 may be collected continually, using the data acquisition module 23 of the PainTrace application 70 within the PMD 10 for display on the device and/or on other digital devices through a network 12 within a clinical or hospital environment and/or the BioTraceIT PMD server system 18. The data acquisition module 23 may improve data quality by reducing noise and anomalies, and the data may be sampled and compressed for display within the PainTrace application 70. The PainTrace data signal 72 may be presented in relationship to an axis 74 denoting a zero baseline where the PainTrace device may measure the difference in either voltage or current from EDA measurements taken from sensors placed contralateral, and at times ipsilateral, on the patient with multiple biosignal sources potentially contributing to the overall measurement based on timed monitoring and integration. Data signals 72 that are equal to or very close to the zero baseline indicate a balance in EDA from each side of the body and correlate to balanced pain matrix activity which does not represent a pain state. Data signals 72 either above or below the zero baseline indicate a difference in contralateral EDA and an increase in pain matrix activity. Therefore, for the patient with signal peaks extended further, in the direction denoting pain whether that is positive or negative as determined by the scaling system, from the axis 74 an increase in pain is indicated. As shown in FIG. 4 a patient with a negative reading, below the baseline, represents a degree of pain. A patient with an initial negative reading will represent an increase in pain via an increasingly more negative number, or a negative deflection away with respect to the zero baseline 74. The delta between the initial pain measurement and subsequent pain measurement represents the increase or decrease in pain. Therefore, in this example a deflection in the positive direction denotes a relative decrease in pain or less pain. The PMD 10 transforms this deviation acquired as a raw biosignal into a pain score more analogous to the currently used standard scales for self-report that equate no pain as equivalent to zero and equate the worst pain as equivalent to 100. Using the PMD 10, scales of pain can be standardized based on a patient's BioTrace Factors 150 and derived PainTrace Factor 102. For example, young patients may consistently have more positive numbers and therefore a negative reading would be more significant in this patient population. Conversely, elderly patients may have generally more negative, or less positive, readings and therefore a negative number is associated with a different level of pain. The PMD 10 uses information about the patient and other patients of similar demographics in normalizing the pain matrix activity data collected to generate BioTrace Factors 150 and derive a PainTrace Factor 102 specific for the patient but normalized to a scale based on similarly situated populations. Additional readings from ipsilateral sensors may also be taken and used to calibrate and validate pain readings where this data is also used by the PMD 10 to normalize collected pain matrix activity data, as described herein.

A tolerance level 76 may be calculated specifically for the patient based on BioTrace Factors 150 and acquired PainTrace data as described herein. The tolerance level 76 may denote levels of intolerable pain for the patient and may be determined from maximum values of pain previously recorded for the patient, with the threshold increasing if the current maximum value is exceeded. The collected data may therefore be normalized based on patient factors, individual response to pain, and demographics that have a known influence on pain and the tolerance level 76 may be presented above or below the zero baseline 74 as dictated by the BioTrace Factors of the patient. The PainTrace data signal 72 may be presented with a time block 78 to associate the onset and duration of pain to physiological activities during the acquisition of data from the PainTrace device 14. The HCP may customize a time scale 73 to view data as longer or shorter periods of time from minutes, to hours, to days and other time periods as desired. The PainTrace data may further be combined and presented with information on patient activity, the administration of medication and other information within the time scale 73. The time block 78 may include scroll features 80 to adjust the time scale 73 for review of data.

The PainTrace application 70 further provides icons for data entry and drop-down fields where applicable with a first icon providing for the administration of medication to be entered by a patient or HCP. The Med icon 84 may expand and present a list of medications currently prescribed for the patient, and/or provide a data entry window for a patient or HCP to enter information about for example an over the counter pain reliever. The Med icon 84 may also be integrated with electronic medical records (EMR) to decrease duplication or to augment EMR when desired. The type of administration icons 85 for the medication may provide a quick reference and verification for the HCP of when and what type of medication the patient was administered over a period of time. The Med Administration icon 85 allows a patient or HCP to drag and drop a Medication Note 88 along the timeline or integrate related data from electronic medical records. If the administration of medication is over a period of time such as through intravenous administration (IV) the HCP may drag and expand the indicator 98 over the time period of administration or for any desired period of time. A Nutrition icon 90 may provide for the patient or HCP to enter information on food intake, a Sleep icon 92 may provide time of sleep, an Activity icon 94 may provide other activities, such as work, alcohol consumption, or other social activities, and an Exercise icon 96 may provide time exercising with any icon selected providing an indicator 98 that may be expanded along the timeline to show the actual time spent. In an embodiment, the PainTrace application 70 may provide for data entry, however in preferred embodiments that data may be captured from the LifeTraceIT component 60 of the PMD 10 that provides patient physiological and activity data, from the MediTraceIT component 64 of the PMD 10 that would integrate, as an adjunct to electronic health records, all of the patients prescribed medication, treatment protocols, interventions, other information from patients health records, and costs into the PainTrace application 70, and/or the BioTraceIT component 62 of the PMD 10 that may add a prescribed treatment protocol within the timeline for a patient to follow and adhere to. The patient may then confirm completion of steps within the treatment protocol. The PainTrace application 70 within the PMD 10 provides a basic, focused pain reading of the patient and groups and displays this information within specific timeframes, treatments and activities of the patient to make the pain measurement data and biophysical information useful for a patient or HCP. A BioTrace Progress Score 280 evaluating all these factors can be generated for each patient as a quick reference to cumulatively track patient progress and improvement or decline in outcome. Physicians can further evaluate cumulative progress by viewing individual data sets including BioTrace Factors 150 that influence the cumulative BioTrace Progress Score 280.

The PainTrace application 70 may further provide Average Pain Measurement Readings (PMR) 100 over any selected period of time and the PainTrace Factor 102 based on a scale derived from the measured physiological data and the BioTrace Factors of the patient. The individual pain matrix response can be measured in relation to a controlled and standardized noxious stimulus. As described above, central nervous system test such as the supraorbital pressure or sternal rub, or peripheral tests such as squeezing the lunula area of the finger or toe nail are repeatable and measurable through the use of calibers and compression and tension gauges to standardize the applied stimulus in comparison to current test procedures which deliver pressure or stimulus in a non-standard fashion based on a physician's or healthcare provider's manual touch. The individual pain matrix response levels are recorded in response to the stimulus as a baseline during general physical exams to establish baseline scores at time of injury or illness. The standard noxious stimulus combined with BioTrace Factors 150 form a portion of the data that is transformed into a patient's PainTrace Factor 102. A Contribution Factor 104 as described herein presents the level that an individual biological, behavioral, environmental, psychological, and social factors, the BioTrace Factors 150 relate to the PainTrace Factor 102. The PainTrace application 70 of the PMD 10 may also provide additional physiological measurements such as heart rate variability 302 which may be used to determine a patient's vagal tone to provide indicators for HCP on the patient's reaction to stress, disease states, and the vulnerability toward illness. (Gunther et al. Critical Care 2013, 17:R51 http://ccforum.com/content/17/2/R51). In instances where the PainTrace Factor 102 is reflecting hyperactive pain matrix activity but the heart rate variability 302 is demonstrating misaligned, or hypoactivity, in relation to the PainTrace Factor 102 this may serve as a tool for a physician to identify a source of unexplained chronic pain. Vagal tone and vagus nerve activity has been linked to pain relief via endogenous release of endorphins. A flag highlighting a disparity in these two diagnostic indicators may serve as a tool for further testing and attention to a potential medical issue. Napadow, V et al. Evoked Pain Analgesia in Chronic Pelvic Pain Patients using Respiratory-gated Auricular Vagal Afferent Nerve Stimulation. Pain Med. 2012 June; 13(6): 777-789. Published online 2012 May 8. doi: 10.1111/j.1526-4637.2012.01385.x). Within any PMD 10 component a patient icon 106 provides access to patient data that may be displayed through the LifeTraceIT component 60 or other patient data applications. Other functional features 108 of the PMD may be provided to save, print or email data, and create reports, from within the PMD display.

Figure 5:
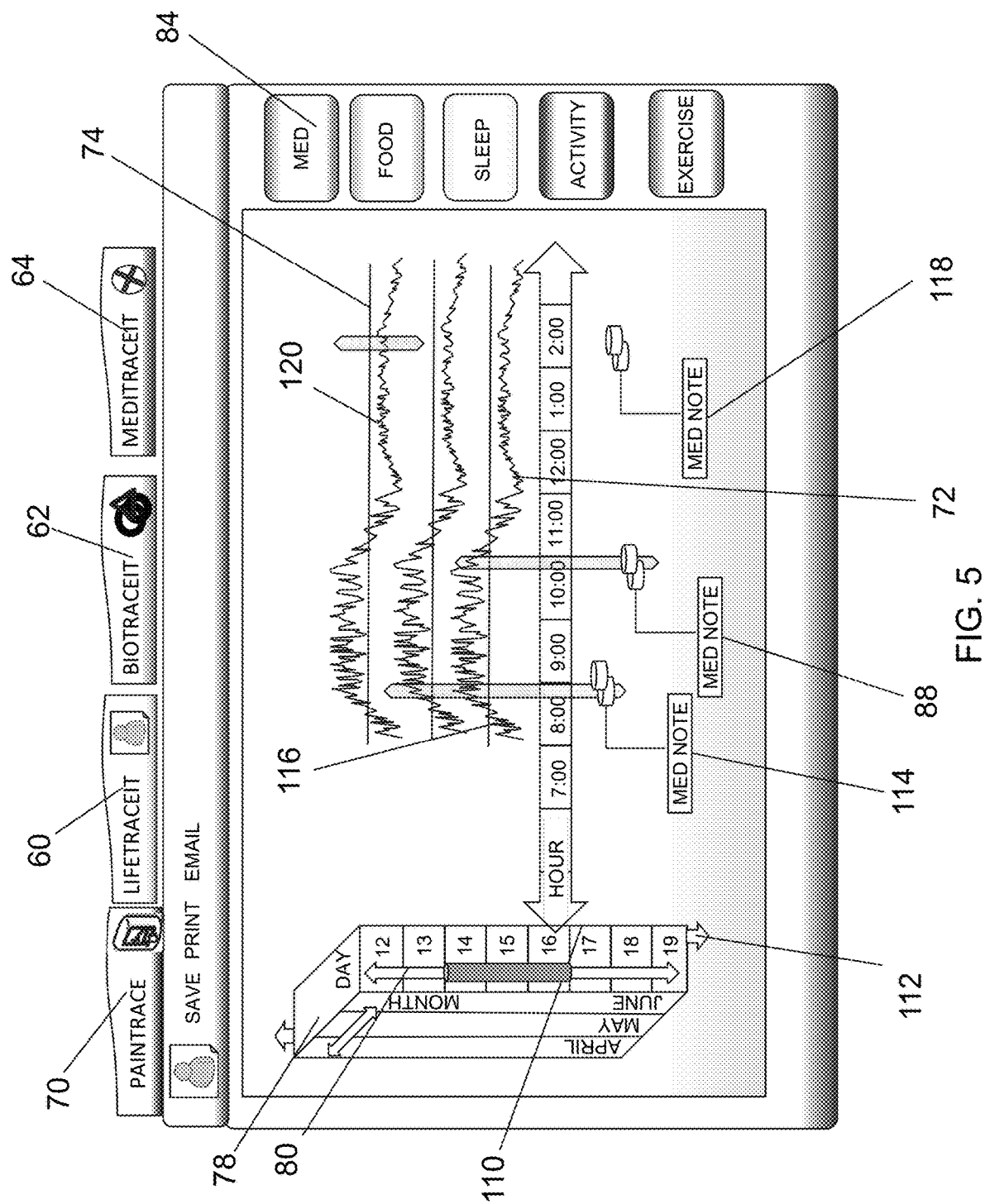
FIG. 5 is a diagrammatic representation of an embodiment of the PainTrace application component in an embodiment of the PMD of the present invention.

The PMD 10 may provide a slider 110 to view and compare data over a range of days or even weeks to find outliers and anomalies. The data signal 72 from similar time periods may be selected by expanding the slider 110 over the days of interest. Any number of indicators 98 may be selected for viewing to provide a comparison of these indicators. In this example, an administration of medication shows a decrease in the PainTrace data signal 72 shortly after the patient is administered the medication as shown by Medication Note 88 in FIG. 4. However, in FIG. 5, as indicated by Medication Note 88 the medication is administered but the PainTrace data signal 116 demonstrates an increase in pain delineated by a decline to a more negative number as opposed to the expected increase to a positive number which would reflect less pain after the administration of pain medications. As indicated by Medication Note 118, the patient appears to have administered pain medication when pain levels were well below the axis 74 with little change in the PainTrace data signal 120 which therefore may indicate a tolerance to medication requiring a change in dosage and/or a possibility of abuse of the medication by the patient. The PMD 10 highlighted these disparities which triggered further investigation. Upon review of patient tracked activity, the increase in pain after Medication Note 88 was attributed to a physical therapy session just prior to the medication administered in Medication Note 88. Activity information also disclosed that the patient ate lunch just prior to Medication Note 118. Food would not explain why medication was taken when the patient was not experiencing pain so the patient was interviewed. Upon questioning it was determined that the patient thought that taking medication with a full stomach would mitigate potential nausea. Understanding the combination of all of these variables would not have been possible, or noticed so simply, without the PMD 10. The data, tracking, and physiological signals combined from PainTrace data signals 72 and the LifeTraceIT application 60 are transformed via the PMD 10 to create healthcare tools that support educated decision making and improved healthcare outcomes. The patient was further educated about the usage and timing of medication to decrease the incidence of mismanaged acute pain becoming chronic pain, which is much more difficult and costly to treat.

The PainTrace device 14 is capable of measuring the moment-to-moment relative dominance of the pain matrix and central nervous system through the detection of voltage or current differences between a first PainTrace sensor placed at a location on the left side of the body and a second PainTrace sensor placed at a similar location on the right side of the body. Changes in the pain matrix and central nervous system activity and vagal tone generate voltages or current that as measured using the low offset potential of the PainTrace sensors provide a consistent quantifiable measurement of pain. The PainTrace sensors are passive and therefore do not require administering voltage to the patient. The PainTrace sensors may be of AgCl coated silver substrate, graphene, or other materials as a coating to sufficiently conduct the voltage changes of the pain matrix and central nervous system activity of a patient as measured across the body mid-line. The PainTrace sensors may be wet or dry sensors based on the amount of time the sensors are worn while data is collected. For wet sensors an adhesive may be used to adhere the sensor to the skin and a conductive gel may be pre-applied to the skin location or to the sensors so that the conductivity is consistent from the surface of the PainTrace sensor to the skin. Dry sensors however may be used for longer periods of wear to monitor changes in pain over time.

To determine differences in conductivity between the PainTrace sensors on each of the left and right side of the body particularly using dry sensors where gel is not pre-applied, measurement of impedance, conductance, and/or other measurements may be made by applying a voltage to the sensors and measuring the impedance for example. These measurements may also be taken from one of either the left or right sensors by connecting the sensor to an ipsilateral sensor to take measurements from one side of the body. Additional measurements may be taken from ipsilateral sensor pairs or sets on contralateral sides of the body and the readings may be used to calibrate the readings for each of the PainTrace sensors based on differences in skin contact, skin quality, movement, and the other effects of the sensor to skin interface and physiologic measurement. Large differences in these measured values may indicate a faulty sensor or limited contact of the sensor surface to the skin. For example, for smaller differences in impedance within specified tolerance levels, the PainTrace application 70 of the PMD 10 may apply calibration algorithms to adjust the offset of voltage or current measurements between the left and right PainTrace sensors. Other calibration methods accessible using the PMD circuitry of the PainTrace application 70 may include an iterative linear resistance calibration to determine a calibration curve as resistance is systematically increased and/or decreased and voltage or current measurements are taken at each impedance adjustment. From the calibration curve a variable load resistor across the connection of the contralateral and/or ipsilateral sensors is adjusted to optimize voltage and current flow and improve the signal to noise and quality of the measured signal from the PainTrace or other biophysical sensors. For example, the variable load resistor may be adjusted to produce maximum current flow. Some embodiments of the PMD circuitry of the PainTrace application 70 include components to apply a float current to the electrochemical capacitor of the PainTrace sensor to improve the energy and power characteristics. Losses in efficiency due to self-discharge during storing or in mishandling of sensors during application may occur, diminishing the overall sensitivity of the sensors. Using the linear resistance calibration or other calibration methods a suitable current value may be determined and applied to each PainTrace sensor during initialization or periodically during and between data acquisition to keep the electrochemical capacitor of the PainTrace sensor fully charged.

Additionally, because patient movement may affect the overall quality of readings possibly by creating noise spikes or other anomalies, the PainTrace application 70 may use one or more accelerometers on the PainTrace device or on other digital devices or from other sensors to correlate noise spikes or anomalies with movement and use this information to smooth, reduce or remove these features from the collected PainTrace data signal 72. These adjustments provide for the PainTrace application 70 component of the PMD 10 to display and transmit accurate comparisons of the voltage measurements from the left and right PainTrace sensors to provide consistent quantifiable measurements of pain matrix and central nervous system activity via measurement of the circuit connecting contralateral PainTrace sensors.

Figure 6A:
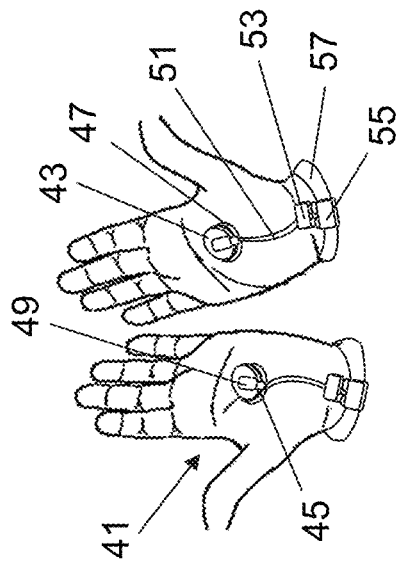
FIG. 6A is a diagrammatic representation of an embodiment of the pain measurement sensors (referred to herein as the PainTrace sensors or PainTrace device sensors) that provide data to an embodiment of the PainTrace application component in an embodiment of the PMD of the present invention.
Figure 6B:
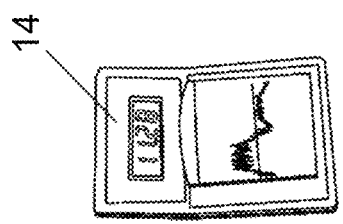
FIG. 6B is a diagrammatic representation of an embodiment of a PainTrace device that provides data to an embodiment of the PainTrace application component in an embodiment of the PMD of the present invention.

As shown in FIG. 6A, the PainTrace sensors 35 in a first embodiment, may be in the form of two self-adhesive sensors placed in the palm of each hand, the hypothenar or thenar eminence, of a patient that directly connect using wires 33 to the PainTrace device 14 shown in FIG. 6B and as described in U.S. Pat. No. 8,560,045 to Burke. The PainTrace sensors 35 may in some embodiments have a holder 39 with a weak adhesive that holds the sensor 35 in place and that connects the wires 33 to the PainTrace device 14. The PainTrace sensor 35 may be removed from the holder 39 and be disposed of after one or more readings over a defined period of time. For example, in a medical physical a pain measurement may be taken after having the patient sit quietly for a short period of time of maybe 10 minutes. A measurement is then taken from the patient using the PainTrace device 14 and the data collected may be used to calculate a PainTrace Factor 102 that is recorded to be used as a baseline for future pain measurements, even if the patient is not currently experiencing any pain. For example, during a general physical exam, baselines are determined via the PMD with the combination of standardized noxious stimuli implemented through controlled and timed pressure. Monitored response to stimuli formulate a patient's pain matrix response levels which in combination with the patients BioTrace Factors 150 develops an individual PainTrace Factor 102 for the patient. The pain matrix response levels are available for immediate use and are stored for subsequent illness or injury requiring pain measurement and physical diagnosis. The self-adhesive left and right sensors 35 are removed from the holder 39 and thrown away after the single use. The holder 39 may in some embodiments, may be compressed to the skin to form a seal thereby creating suction to adhere the sensor in place removing the requirement for gels. Because removing and replacing each sensor within the holder 39 may cause changes in conductance of the surface 37 of the PainTrace sensor 35 to the patient's skin additional conductive gel may be applied to the region or sensor if wet sensors are used and the PainTrace application 70 may measure impedance and/or run calibration algorithms to adjust voltage measurements from the left and right sensors to be within acceptable tolerance ranges of one another as necessary based on these measurements.

Figure 6D:
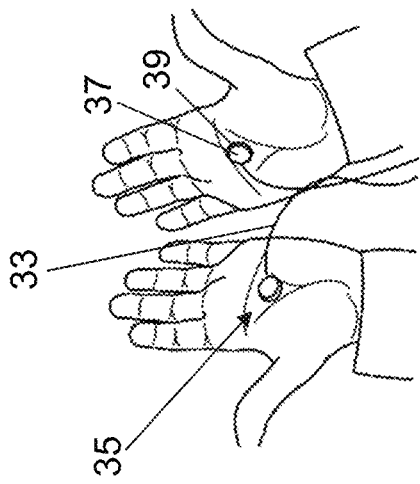
FIG. 6D is a diagrammatic representation of a further embodiment of the PainTrace sensors that provide data to an embodiment of the PainTrace application component in an embodiment of the PMD of the present invention.
Figure 6C:
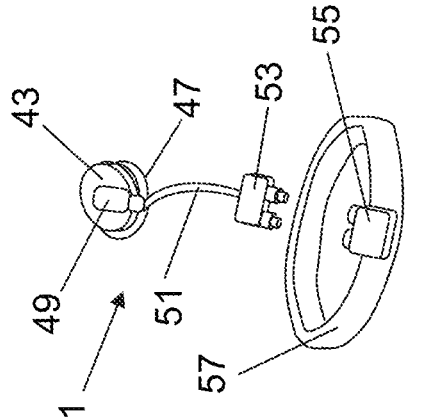
FIG. 6C is a diagrammatic representation of another embodiment of the PainTrace sensors that provide data to an embodiment of the PainTrace application component in an embodiment of the PMD of the present invention.

In a further embodiment of the present invention, as shown diagrammatically in FIG. 6C, a replaceable sensor clip 41 removes the requirement that only the PainTrace sensor 43 be removed for replacement. The sensor holder 45 is of a rigid material with a flexible adhesive base 47 that is of a compressible conductive material that provides for the PainTrace sensor 43 to remain in contact with the skin's surface even when the patient is moving. A fastener 49 that securely holds the PainTrace sensor 43 in place is attached to a rigid arm 51 that applies pressure to the PainTrace sensor 43 to align and hold the PainTrace sensor 43 against the flexible conductive adhesive base 47 thereby maintaining electrical contact with the skin. The rigid arm 51 is thin enough to minimally interfere with a patient's dexterity in the use of their hands but made from a rigid wire that may be bent to conform the patient's palm or other area of the body using the PainTrace sensor clip 41 to align and hold the PainTrace sensor 43 to the patient's skin. The replaceable PainTrace sensor clip 41 has a connector 53 that in a first embodiment may be inserted into a receiver 55 attached to a wrist, arm, leg or ankle band to position the PainTrace sensor clip 41 in different locations on the body to obtain acceptable readings. The replacement of the PainTrace sensor clip 41 is very easily done by pulling the connector 53 out and removing it from the receiver 55 as shown in FIG. 6F and then replacing the sensor clip 41 with another sensor clip 41. The rigid arm 51 and flexible, conductive adhesive base 47 align and hold the sensor 43 to the skin so minimal time is needed to replace the PainTrace sensor 43 and begin acquiring PainTrace sensor data 72.

The PainTrace application 70 may further acquire impedance and other measurements, apply calibration algorithms to determine a voltage offset of the left and right PainTrace sensors 43 and adjust voltage measurements and based on this calculated value and tolerance settings a faulty PainTrace sensor 43 may be identified and be replaced. The size, shape, and surface area of the PainTrace sensors may be determined by the type of subject and on which body part the sensor is attached. The PainTrace sensor 59 may be affixed to a support 61 and adhered to the hair of the animal, as shown in FIG. 6D. The measurement of the pain matrix and central nervous system activity as it relates to pain on the animal is a unique application of the PainTrace device 14, where for an animal that has no ability to communicate or human that cannot communicate, the device 14 provides vital information about the amount that an incapacitated or non-communicative patient may be suffering from pain and the efficacy of treatment. In further embodiments, the PainTrace sensors 41 may be attached to a collar 65 that may be positioned in a location near to the area of the body experiencing pain or be worn or draped around the neck to not impede the patient's mobility but provide for constant monitoring of the patient's PainTrace sensor readings 72. The monitoring collar 65 as shown in FIG. 6E, or other wearable device may further provide for additional sensors 63 to be affixed to the collar and collect data such as a heart rate and heart rate variability, photoplethysmogram (PPG), blood pressure, skin temperature, movement, GSR, and other vital signs.

Figure 6E:
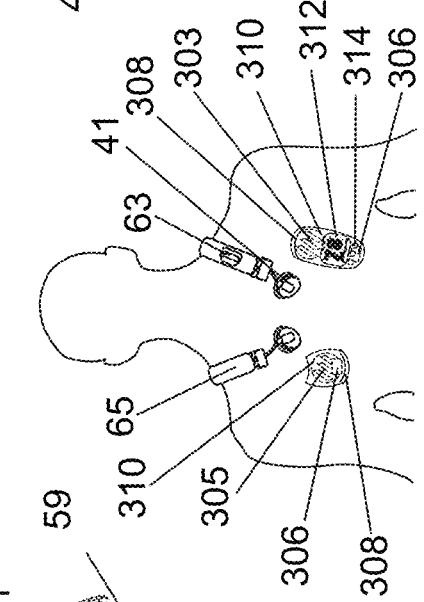
FIG. 6E is a diagrammatic representation of a still further embodiment of PainTrace sensors and PainTrace measurement devices with sensors that provide data to an embodiment of the PainTrace application component in an embodiment of the PMD of the present invention.
Figure 6F:
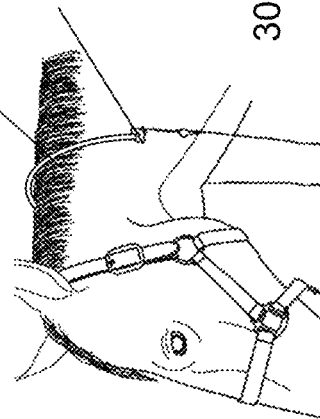
FIG. 6F is an exploded view of a diagrammatic representation of the embodiment of the PainTrace sensor and holder of FIG. 6C that provide data to an embodiment of the PainTrace application component in an embodiment of the PMD of the present invention.

In further embodiments, the PainTrace sensor and PainTrace device may be a single PainTrace measurement device 303 in a small housing without a support 61 or collar 65 and simply be affixed to the patient using adhesive as shown in FIG. 6E. In some embodiments, a separate PainTrace measurement device 303 would be affixed to the left and right side of the patient's body, however in preferred embodiments a PainTrace adhesive sensor device 305 would transmit data signals 72 using a wired connection or wireless transmitter 306 such as a Bluetooth transmitter to communicate with the PainTrace measurement device 303. The PainTrace adhesive sensor device 305 and PainTrace measurement device 303 may have a sensor holder 308 to slide or snap in sensors 310 into a housing 312. The PainTrace measurement device 303 using the PainTrace application 70 may process the data signals from the PainTrace adhesive sensor device 305 and from the sensor 310 on the PainTrace measurement device 303 to calibrate the signal and determine the signal delta that provides the pain level reading 72. The PainTrace measurement device 303 may have a display screen 312 to display the PainTrace data 72 and/or PainTrace Factor 102 and/or have LED lights, alarm signals or other indicators 314 that show a level of pain based on for example the color of a light, the volume of a sound, or the rapidity that a sound repeats to indicate the level of pain as compared to the pain tolerance level 76.

Similar indicators 314 may be used on a further embodiment of the PainTrace measurement device 320 as shown in FIGS. 6G and 6H. In this embodiment of the PainTrace measurement device 320, the left and right side sensors 322 are releaseably attached to holders 324 that are affixed to the device housing 326. The PainTrace measurement device 320 is then affixed along the center line C of the body with the left and right sensors 322 affixed using a weak adhesive to the left and right side of the body, respectfully. The PainTrace measurement device 320 using the PainTrace application 70 of the PMD 10 processes the data signals from the left and right sensors 322 to calibrate the signal and determine the signal delta that provides the pain level reading 72. The PainTrace measurement device 303 may have a display screen 312 to display the PainTrace data 72 and/or PainTrace Factor 102 and/or have LED lights, alarm signals or other indicators 314 to show a level of pain. As with this and other embodiments of the PainTrace measurement device 320, the PainTrace data 72 may then be transmitted using a wired connection or using wireless transmitter 306 such as a Bluetooth transmitter to a wireless receiver such as a smartphone that may also have the PainTrace application 70 and/or other components and features of the PMD 10 accessible as a software app on the smartphone or mobile device. The smartphone may then transmit collected data from the acquisition environment 1 to a local or remote network 12 such as within a clinical or hospital environment and/or to the BioTraceIT PMD server system 18. Collected data may be integrated with previously collected PainTrace sensor data for review using components and features of the biotrace application software of the PMD 10 where tolerance settings may be provided to issue alerts if any sensor readings are outside acceptable levels. Any alerts that result in actions that can be taken to correct placement of sensors or the device can be displayed either via GUI or mobile device apps or software integrated with nursing stations or healthcare system networks. The PainTrace sensors may also be integrated with other medical devices and equipment such as with a blood pressure monitor as shown in FIG. 6I, where a first PainTrace sensor 330, for example designated for the left side of the body, may be held to the skin of one arm by the cuff and bladder 332 and a second cuff 334 or band as shown in FIG. 6J may be provided to hold a second PainTrace sensor 330 that is held to the skin on the other side of the body by similarly wrapping the cuff 334 around the other arm. The two cuffs 332 and 334 may be wired together or use a Bluetooth or other wireless transmitter to have sensor readings from the sensor 330 on the second cuff transmitted to a PainTrace device 336 that may be integrated with the analog or digital measuring device of the blood pressure monitor. A holder 338 may be attached to each cuff 332, 334 to provide for the sensor 330 to be slid or snapped into place to be affixed to each cuff 332, 334 and either wet or dry sensors may be used with tightening of the cuff 332, 334 providing adequate tension to hold the sensors 330 against the skin. The PainTrace signal data 72 from the PainTrace sensors may be transmitted to a digital display console 336 of the blood pressure monitor that has the PainTrace application 70 of the PMD 10 installed to calibrate the two sensor measurements and determine the signal delta to display pain level readings 72 and/or PainTrace Factor 102 values for recording with the blood pressure reading. In further embodiments, the PainTrace data 72 may be collected at different times where a reading is collected from the right side of the patient and is stored and a second measurement is taken from the left side of the patient and then calibrated with the first measurement taken to determine the signal delta and display pain level reading 72 and/or the PainTrace Factor 102.

In other embodiments the PainTrace measurement device 67 may be worn as an activity monitor such as on a wrist band 69 as shown in FIGS. 7A and 7B with a PainTrace sensor device 307 that as described herein is connected to the PainTrace measurement device 67 using a wired connection or wireless transmitter such as a Bluetooth transmitter. The wrist band 69 may be adjustable to adjust the tension of the sensor and/or be elastic to securely hold the sensor in place where in some embodiments strain measurement devices may be added to the wrist band 69 to measure the tension with these measurements used in calibrating the PainTrace signal data. The control interface 71 of the PainTrace measurement device 67 may have a display screen 73 that may be a touch screen, LCD, LED, or other type display. The control interface 71 may also have one or more control buttons 75 around the display or within the display as determined by the type of display. The control buttons 75 may turn power to the device on and off, start and stop acquisition, calibrate the device, provide scrolling to review collected data, run diagnostics tests, send alerts, and perform other functions. The display 73 may show the collected signal data 77, display the PainTrace Factor 102 and display other components and features of the biotrace application software of the PMD 10. For example, the control buttons 75 and/or display screen 73 may provide for inputting data such as exercise, activities, and other information within the LifeTraceIT component of the PMD 10. The PainTrace sensor device 307 may have a wristband 309 and electrical components 311 for the collection and transmission of data. In an embodiment, a support 313 may provide for the attachment of the electrical components 311 and provide for a wet or dry sensor 315 to be affixed to the support 313 using an adhesive 317. In further embodiments, the support 313 and sensor 315 may have an interlocking connector as described herein to provide for the replacement of the sensor 315 when using the PainTrace sensor device 307 over long periods of time. In some embodiments, the sensor 315, support 313, and wrist band 309 may all be disposable.

The housing 79 of the PainTrace measurement device 67 supports the control interface 71 so that it is easily accessible across the wrist of a user. The housing 79 also supports the PainTrace sensor 81 in some embodiments. The housing 79 is lightweight and of a minimal thickness as shown diagrammatically in a side elevation view in FIG. 8A. The housing 79 may further be contoured for comfort and be substantially rectangular in shape to be worn across the wrist to provide for a large contact surface area 83 of the sensor and sensor clusters as shown in FIG. 8B. In some embodiments, the sensor 81 may be a wet sensor that requires a conductive gel or adhesive 317 to be applied to the sensor or the skin during use. For example, the PainTrace measurement device 67 and PainTrace sensor device 307 with wet sensors may be used as part of a medical physical where a HCP may prepare the sensors with conductive gel, or use a sensor that has been pre-applied with gel at the manufacturer, and may place the PainTrace measurement device 67 and the PainTrace sensor device 307 on each of the patient's wrists, palms, or appropriate anatomy on contralateral sides. After sitting quietly for a few moments, pain level and pain matrix and central nervous system activity data 72 and the patient's PainTrace Factor 102 may be collected with other BioTrace Factors collected from other sensors to be used as a baseline in a measurement of pain with other biophysical readings of the patient.

The PainTrace sensors 81 and 315 may further be replaceable where wet sensors may be single use and used for example over only two hours while dry sensors may be used for longer periods of time with for continual data collection. The dry sensors for example may be replaced daily, or every two to three days, or after a longer period of time. As shown diagrammatically in FIG. 9A, the PainTrace sensor 81 may also be of minimal thickness and a connector support 87 may be provided to releaseably connect the PainTrace sensor 81 to the housing 79. In an embodiment, the housing 79 supports PC Boards 89 and other electronics for the controller interface 71 and PainTrace sensor 81, as shown in a bottom view of the PainTrace measurement device 67 in FIG. 9B. The connector support 87 may have left and right support brackets 91 and 93 that may be installed on a base 95 within the center of the housing 79. Each of the left and right support brackets 91 and 93 may include a compression spring 97 and each compression spring 97 may have a strain gauge 99 to measure pressure of the PainTrace sensor 81 against the skin of the user to determine equal pressure between two PainTrace measurement devices 67 that are worn on each wrist of the user in collecting data measuring pain and other biophysical readings such as skin conductance. The connector support 87 may also provide a locating pin 101 to align a sensor connector 103 within the connector support 87.

The sensor connector 103 as shown in a bottom view of the PainTrace sensor 81 in FIG. 9C is positioned within the center of the PainTrace sensor 81. The sensor connector 103 may have a tab extender 105 that extends from an opening 107 in the center of the sensor connector 103 in parallel with the longer dimension of the contact surface 83. The tab extender 105 is affixed to a spindle 109 that extends to a plate 111 with the spindle 109 creating an offset distance between the tab extender 105 and the plate 111. The plate 111 may be affixed to the bottom 113 of the contact surface 83 of the PainTrace sensor 81 using an adhesive or another attachment device. As shown in FIG. 10A, the bottom surface 111 may have conductive strips 115 or other electrical connection points to mate with the compression springs 97 as electrical contacts or with other electrical contacts from the connector support 87.

As shown in FIG. 10B, the PainTrace sensor 81 is connected to the housing 79 using each end 117 of the tab extender 105 and the left and right connector supports 91 and 93. The connector supports 91 and 93 are formed with a vertical extension 119 and an overhang 121, as shown in FIG. 10C, with the overhang 121 of the left connector support 91 directed towards the overhang 121 of the right connector support 93. The connector supports 91 and 93 are spaced at a distance apart that is slightly larger than the width of the tab extender 105 of the sensor connector 103 so that the tab extender 105 may be inserted between the two connector supports 91 and 93. The opening 107 on the tab extender 105 aligns with the locating pin 101 on the base 95 of the connector support 87 and provides for the PainTrace sensor 81 to be rotated to have the ends 123 of the tab extender 105 extend underneath the overhangs 121 of the connector supports 91 and 93 to secure the PainTrace sensor 81 to the housing 79. The compression spring 97 of each of the connector supports 91 and 93 compresses against the PainTrace sensor 81 to push the sensor against the skin to increase contact of the surface contact area 83 of the PainTrace sensor 81 to improve sensor readings. The compression springs 97 may also connect with the conductive strips 115 on the bottom surface 111 of the PainTrace sensor 81 to send signal data 77 from the PainTrace sensor 81 to the electronics of the PainTrace measurement device 67. The PainTrace measurement device 67 may display the signal data 77 within the display 73 of the control interface 71 and/or transmit the data using the communications module 25 within the PainTrace application 70 of the PMD 10 that may be installed on the PainTrace measurement device 67 or be installed remotely on a smartphone or other local digital device, remotely within a network 12 such as within a clinical or hospital environment and/or be transmitted to the BioTraceIT PMD server system 18.

Figure 12B:
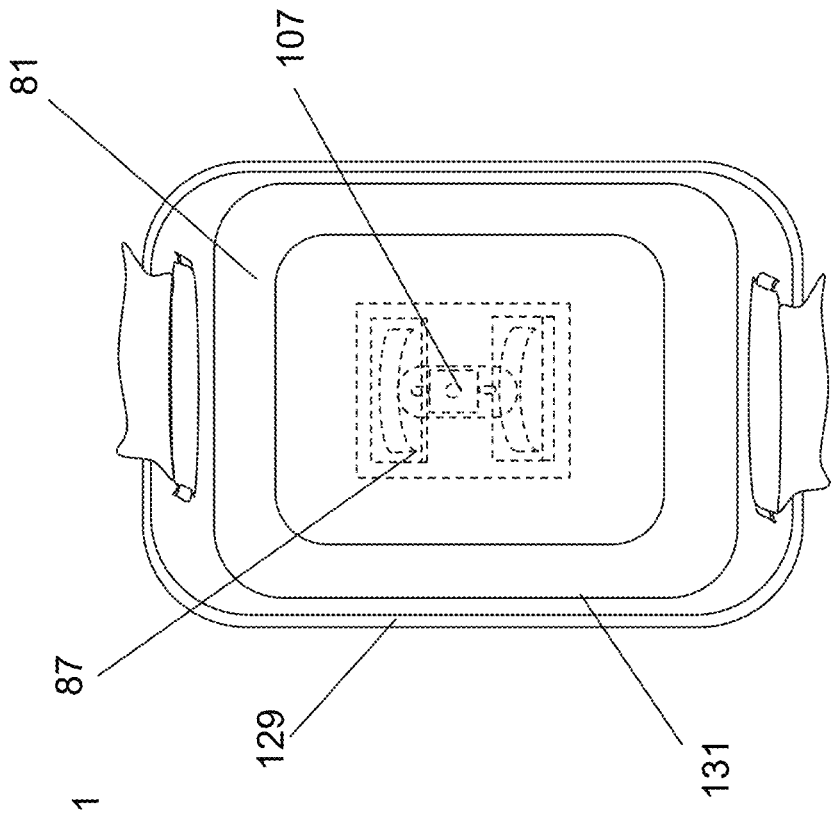
FIG. 12B is a front view of a diagrammatic representation of an embodiment of the PainTrace sensor, sensor connector, and device connector in a locked position.
Figure 12A:
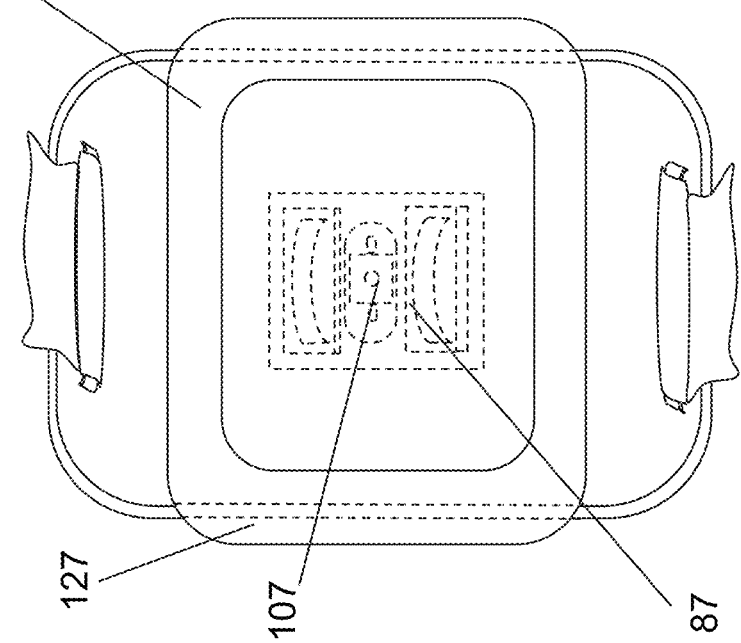
FIG. 12A is a front view of a diagrammatic representation of an embodiment of the PainTrace sensor, sensor connector, and device connector in an unlocked position.

As shown in FIG. 11A, in a first position prior to connection, the sensor connector 103 of the PainTrace sensor 81 is aligned in between and in parallel with the connector supports 91 and 93. The PainTrace sensor 81 is then rotated as shown in FIG. 11B to align the PainTrace sensor 81 perpendicularly to the connector supports 91 and 93 and have the bottom 113 of the sensor contact surface 83 compress against the compression springs 97. Alternatively, the PainTrace sensor 81 may slide into place in embodiments of the connector without the locating pin 101. The compression springs 97 remain in tension pushing outwards against the PainTrace sensor 81 with the tab extender 105 under the overhang 121 of the connector supports 91 and 93 securing the PainTrace sensor 81 to the housing 79. A ridge or other protrusion 123 may be provided on the sensor connector 103 to lock the PainTrace sensor 81 in alignment with an indent 125 on each of the connector supports 91 and 93. As shown in FIG. 12A, the PainTrace sensor 81 prior to connection may extend beyond the edges 127 of the housing 79 to provide for a user to easily manipulate the PainTrace sensor 81 to rotate and connect the sensor 81. The edges 127 of the housing 79 may form a rim 129 to seat and align the PainTrace sensor 81 on the housing 79. The PainTrace sensor 81 may be of a thickness slightly wider than the housing rim 129 to provide for a user to grasp the edges 131 to rotate and remove the sensor 81 or alternatively a user may simply press down in the middle of the PainTrace sensor to compress the springs 97 and separate the ridges 123 from the indents 125 and turn the sensor to align the tab extender 105 between the two connector supports 91 and 93 and lift the PainTrace sensor 81 off of the housing 79 and/or turn the PainTrace measurement device 67 over to have the PainTrace sensor 81 disengage and fall out of the housing 79. Other embodiments may provide for the PainTrace sensor 81 and 315 to snap in using fasteners and/or locking tabs that may have extensions or buttons that may be compressed to release the sensor from the tabs securing the sensors to the housing 79. Other embodiments for connection of the sensors to a housing, wrist band, collar, support or wearable or other fixture for attachment to the skin are contemplated within the scope of the present invention that may also include means to hold and press the sensor against the skin to maintain conductivity.

The PainTrace measurement device 67 requires measurement from each side of a patient with calibration between the PainTrace sensors 81 or PainTrace sensor device 307 to minimize signal noise and limit erroneous readings. The strain gauge 99 on each of the compression springs 97 or strain gauges electrically connected to other embodiments of the PainTrace device may provide for the pressure of the PainTrace sensor 81 and 315 against the skin to be measured. The strain gauge measurements depending on the placement of the strain gauge on the PainTrace measurement device 67, PainTrace sensor device 307 wrist band 69 or 309, collar 65 or other wearable may provide a marker to ensure equal pressure and tension of the sensors 81 and 315 against the skin. As described herein, the pain measurements using the PainTrace device 14 are passive measurements of skin potential, contrary to galvanic skin response which applies a current. PainTrace device 14 measurements are taken without applying voltage to the skin and instead measure the electrical activity of the pain matrix response to stimuli through the detection of voltage or current differences between a first PainTrace sensor placed at a location on the left side of the body and a second PainTrace sensor placed at a similar location on the right side of the body. In some embodiments, the PainTrace device 14 may include a power supply to apply voltage to the PainTrace sensors or associated ipsilateral sensor pairs attached to the device to take measurements of impedance and conductance and/or other passive measurements which may also be taken prior to, during, or after acquiring pain measurement and pain matrix activity data or at periodic intervals while collecting pain measurement and pain matrix activity data to calibrate the readings for each PainTrace sensor 81 or sensor cluster based on differences in skin contact, skin quality, and the effects of movement on the sensor to skin interface and additional physiological measurements. Because, the PainTrace device applies no voltage to the skin the pain measurement and pain matrix activity data may be continually collected without any adverse effects on the patient and calibration measurements may be performed intermittently between the collection of data to determine the required offsets and calibrate the PainTrace device. The calibration measurements may further determine sensor failure and provide an indicator to the user that the PainTrace sensors 81 and 315 must be replaced.

As described herein using contralateral sensors that are placed in similar locations on the left and right side of the body provide measurements of electrical activity due to neural transmissions that may be both to and from the brain in reaction to locations of pain within the body. The contralateral measurements of the voltage differences from the PainTrace device 14 correlate well with the ratings of pain that a patient may offer such as in comparing the measurements to ratings on the Visual Analog Scale (VAS). In some embodiments the PainTrace device 14 may combine contralateral sensors with ipsilateral sensors on one or both sides of the body to provide additional information of electrical activity within the body. The ipsilateral sensors may acquire measurements passively or actively to for example acquire galvanic skin response GSR at locations similar to the contralateral sensors. Data from ipsilateral measurements may be used to calibrate and improve the signal to noise ratio of the contralateral pain measurements reading. Data from the ipsilateral sensors may further be correlated with the contralateral readings to validate the pain measurement readings where recent studies have shown that increased electrical activity on one side of the body may be related to pain, stress and anxiety.

In an embodiment the PMD includes one or more PainTrace sensors and/or one or more other biophysical sensors that may be arranged in a housing 350 to be installed and remove from the PainTrace Device, a wearable, or another measuring device to have the grouping of sensors be placed on the body at similar left and right locations. In one embodiment the sensor cluster may include a single contralateral sensor 352 and a pair of ipsilateral sensors 354. In other embodiments, the contralateral sensors and ipsilateral sensors may each be in separate housings and be separately placed at locations on the body. For example, a contralateral sensor may be placed on each of the left and right clavicle and two ipsilateral sensors as a pair may be placed on the palm of each hand or at other locations that align along the left or right axis of the body.

Figure 13:
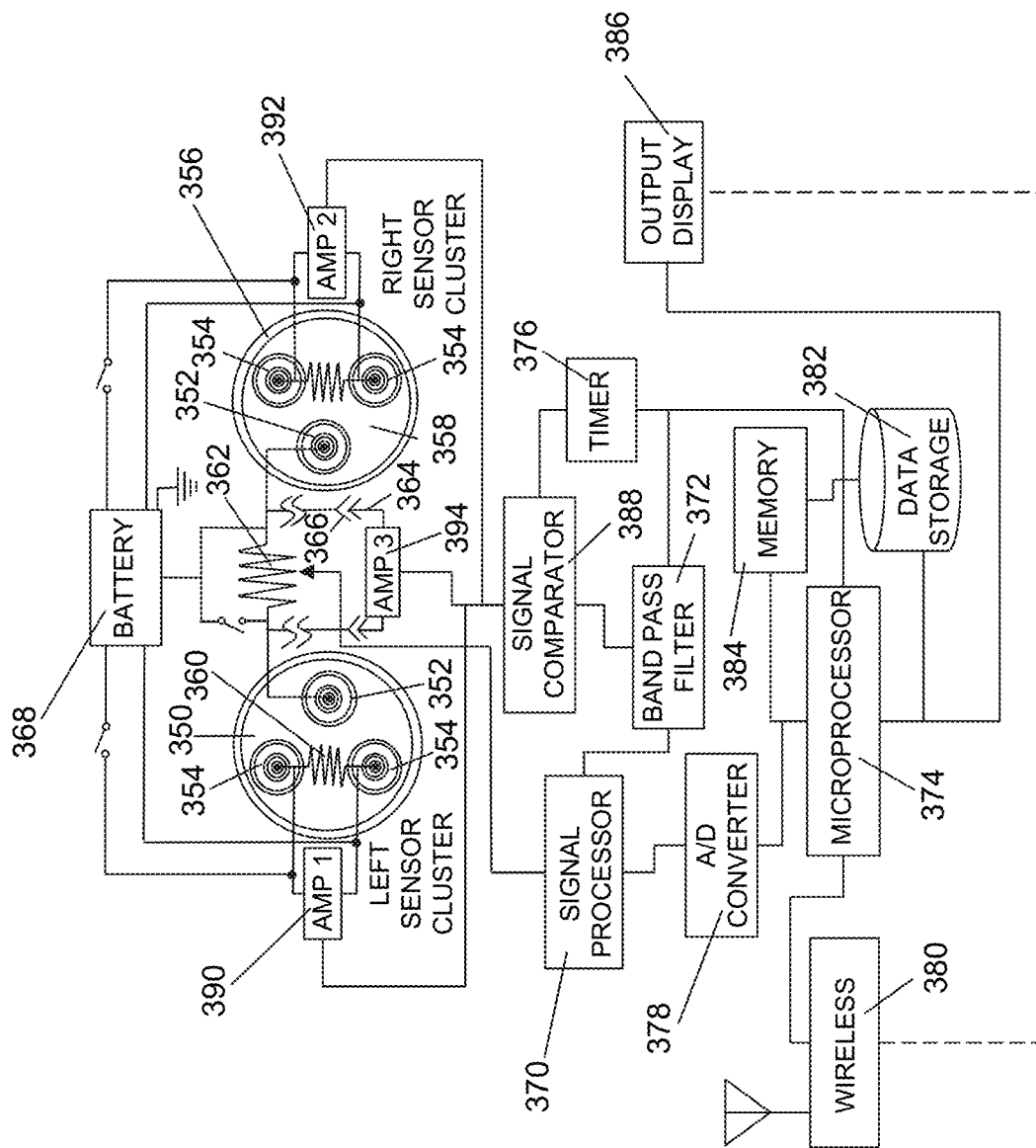
FIG. 13 is a block diagram of an embodiment of components of PMD circuitry in an embodiment of the PMD of the present invention.

In an embodiment of a sensor cluster as shown in FIG. 13, the housing 350 supporting the sensors may be of a flexible material to fold or slightly bend to adapt to movement and positioning of the skin. A border 356 that may be prepared with conductive gel or that has pre-applied gel surrounds the sensor surface 358 of the housing 350 to removably adhere the sensor cluster to the skin. Sensor clusters having both ipsilateral sensors and contralateral sensors may be placed at similar locations on each of the left and right side of the body. The ipsilateral sensors 354 are connected across a load resistor 360 of between 0.5 k to 900 k Ohms and preferably 22 k Ohms. The contralateral sensors 352 are also connected across a load resistor 362 by electrically connecting the left and right sensor clusters. In connecting the contralateral sensors 352, a lead 364 may be of any length with an electrical connector 366, that may be in the form of a clip, snap, dual pin fastener, or other type connector. The lead 364 may extend from each sensor cluster to be connected after the sensor clusters have been placed at a location on the body such as the hypothenar or thenar region of the palm of each hand. To close the circuit between the contralateral sensors 352, the connectors 366 from the left and right sensors may simply be connected together. However, in some instances having a wire across the body may be uncomfortable or awkward for the patient. The connectors 364 may therefore in some embodiments be attached to an article of clothing, each bed railing, or another object that electrically connects the two sensor leads to close the contralateral sensor circuit and still provide for patient mobility and use of the hands. In some embodiments, the lead wire may have a USB type connector to be plugged into a wearable that is placed around the wrist or neck of the patient. The wearable may be in the form of a wireless activity tracker and may include the circuitry shown in FIG. 13 to collect and transmit data from the sensor clusters. Alternatively, the circuitry is contained in the separate handheld PainTrace device 14 that may include wireless transmission or a data output line in the form of a USB cable to transmit and download pain measurement data collected from the PainTrace sensor clusters. In other embodiments, the circuit may be included with each sensor or sensor cluster.

In some embodiments, the PainTrace device 14 of the PMD may not have contralateral sensors connected with a wire across the body but instead have two pairs of ipsilateral sensors each placed contralaterally to the other. Passive and active measurements may be from each pair of ipsilateral sensors separately and/or simultaneously and the signals from these readings are combined to determine pain matrix activity and other biophysical measurements. The ipsilateral sensor pairs that are placed on similar locations of the body may be placed on the wrists where in some embodiments the PainTrace device 14 may be incorporated into an activity monitor and a first activity monitor is placed on the left hand wrist and a second activity monitor is placed on a right hand wrist to acquire pain measurements.

In embodiments of the PainTrace sensor circuitry of the PMD, the circuitry as shown may include signal processing 370 and band pass filter circuitry 372 to improve the signal to noise ratio and quality of the signal. A microprocessor 374 and timer 376 to control the collection, sample rate and transmission of the signal and an A/D converter 378 for converting the measured EDA or other analog signals to digital signals. Software applications, control programs and calibration algorithms such as the iterative linear resistance calibration may be downloaded or transmitted to the circuitry using wireless communication circuitry 380 and or a wired connection and be stored and accessible from data storage 382 and memory 384 within the circuitry. The circuitry may include an output display 386 or data may be displayed on an output device remote from the circuitry through wired or wireless data transmission.

Using both ipsilateral sensors 354 and contralateral sensors 352 provides for a signal comparator 388 to evaluate signal characteristics including voltage, current, frequency, linearity, and amplitude and use these measurements to calibrate and adjust the voltage or current of one of the left ipsilateral sensor signal, the right ipsilateral sensor signal and/or the contralateral sensor signal as prescribed by the comparison of signals. As shown in FIG. 13, output leads from the load resistor 360 are connected to an amplifier where in the embodiment of the circuit shown a first amplifier is designated as AMP 1 with the identifier 390 for the left ipsilateral sensors 354 a second amplifier is designated as AMP 2 with the identifier 392 for the right ipsilateral sensors 354 and a third amplifier AMP 3 with the identifier 394 is connected to the output leads of the load resistor 362 for the contralateral sensors 352. The load resistors of each sensor or sensor cluster may in some embodiments be variable resistors in order to calibrate the circuitry and adjust voltages and current flow. For example, in calibrating the contralateral signal, a variable load resister 362 may be used and a comparison of the contralateral signal to the signal measured from either or both of the left and right ipsilateral sensors may be made. From characteristics of the signals determined by the signal comparator 388, the variable load resistor 362 as shown in this example may be adjusted to boost components of the signal and/or remove outliers that may be related to movement or other signal interference. The band pass filter may further be adjusted as necessary to one or more optimal frequency ranges to remove signal noise. PainTrace sensor circuitry of the PMD may further include a power supply such as battery 368 to apply voltage across the load resistors. For example, calibration steps may include applying a voltage across the load resistor 362 of the contralateral sensors 352 and/or the load resistors 360 of each of the pairs of ipsilateral sensors 354 to verify an electrical connection and/or to determine the skin conductivity. Using a skin conductivity measurement from each sensor, differences in skin contact, skin quality, movement, and the other effects of the sensor to skin interface and physiologic measurement may be identified. Large differences in these measured values may indicate a faulty sensor or limited contact of the sensor surface to the skin. For smaller differences in impedance within specified tolerance levels, the PainTrace application 70 of the PMD 10 may apply calibration algorithms to add or subtract an offset based on the difference in impedance to normalize voltage measurements between the left and right contralateral sensors or pair of ipsilateral sensors.

Figure 14:
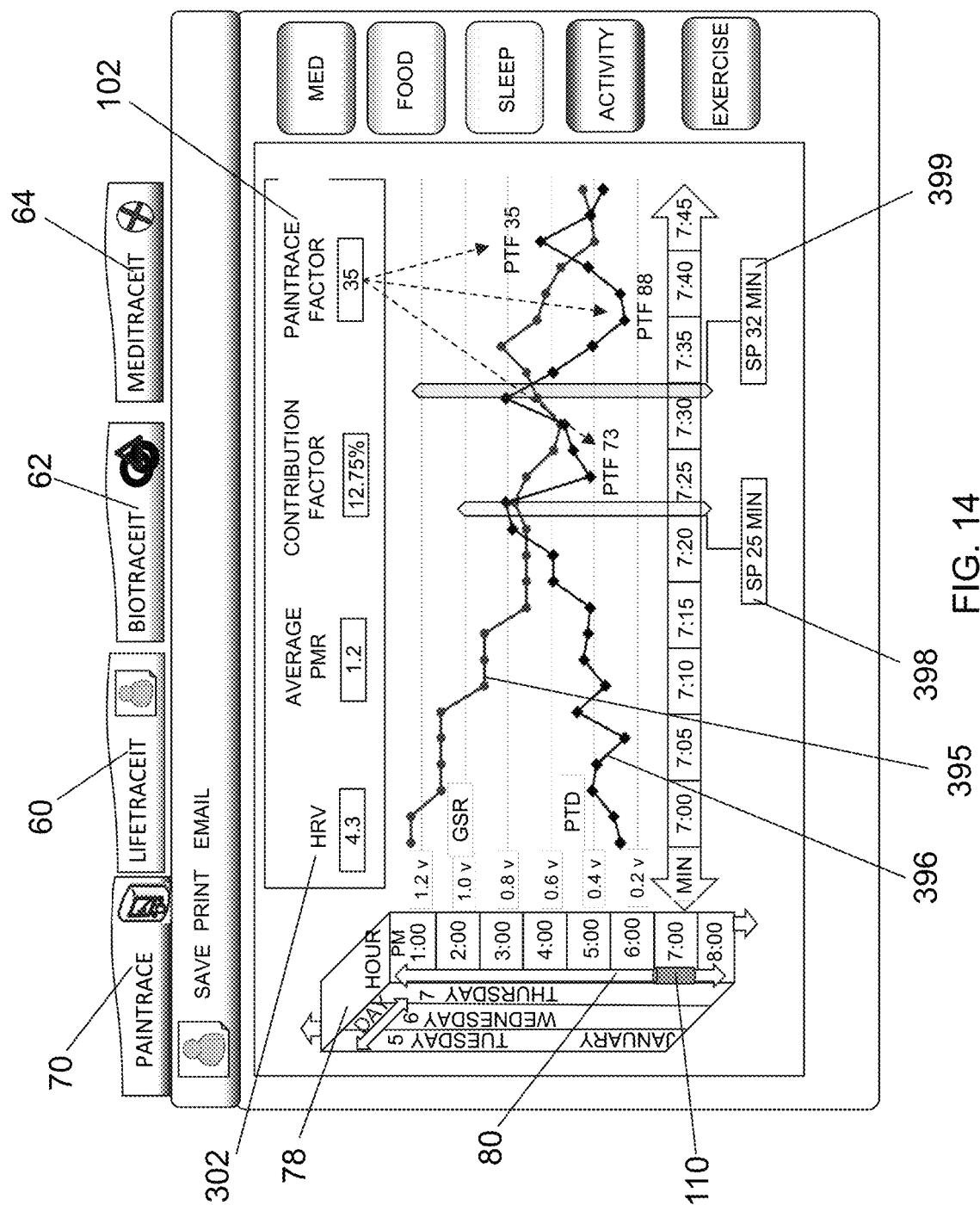
FIG. 14 is a diagrammatic representation of an embodiment of the PainTrace application component in an embodiment of the PMD of the present invention.

Using the PainTrace device of the PMD, data is collected without applying voltage to the skin in order to measure pain matrix activity of the patient. However, by applying a voltage to ipsilateral sensors placed on wither the left or right side of the body, the galvanic skin response GSR may be measured. The PMD uniquely combines and normalizes biophysical measurements such as GSR, HRV, blood pressure, pulse, movement, skin temperature, and other signal data with pain matrix activity data collected using the PainTrace device 14. Through the PMD analysis, the measurement of pain matrix activity may be correlated on a time scale to evaluate peak activity of GSR that may be related to emotional response and points of increased levels of pain. As shown in FIG. 14, simultaneous measurements using ipsilateral sensors located on the fingers of the right hand to measure GSR, and pain matrix activity using the PainTrace device 14 with contralateral sensors placed on the thenar region of the palm of each hand, pain matrix activity is measured over a period of time. The cold pressor test, a standard method for inducing experimental pain, was conducted during a portion of this period. (Walsh et al. Normative Model for Cold Pressor Test. American Journal of Physical Medicine and Rehabilitation. February 1989; 68(1): 6-11). Using the PainTrace application 70 of the PMD 10 and adjusting the time block 78 to hours and minutes data collected over a continuous period of time may be reviewed. The PMD correlates measurements of the GSR readings 395 and PainTrace data 396 and displays the pain stimulus points at 25 minutes 398 and at 32 minutes 399. The PainTrace Factor 102 or other BioTrace Factors 150 may be added to points in the time period for additional information. For example, the addition of the PainTrace Factor 102 may be completed by dragging and dropping the PainTrace Factor icon 102 within the time period. Alternatively, an option to add the PainTrace Factor 102 and other BioTrace Factors 150 through a menu or other application interface may be provided to be displayed such as displaying the PainTrace Factor 102 at maximum points of deflection as shown by the dotted line arrows within the display. Other biophysical measures such as heart rate variability may be individually displayed for the acquisition by simply dragging and dropping the HRV icon 302 into the time period.

The PMD 10 provides for a review of integrated data or individual display of the GSR and pain matrix activity which in this example exhibits an inverse relationship prior to the introduction of the pain stimulus. Over this time period, simultaneous readings were taken with the GSR device being turned on and off at two minute intervals to determine how the introduction of current effected the PainTrace device 14 measurements. GSR cycling was conducted prior to the 25 minute time point in the experiment when the noxious stimulus 398 was introduced after which point in time a consistent GSR measurement was utilized. Fluctuations in PainTrace data 396 dissipated when the GSR device was cycled for longer periods increasing from two to a longer three-minute cycling frequency. Starting at the 25-minute time point the cold pressor test, which consisted of immersing the right foot in an ice bath for 1.5 minutes, is initiated demonstrating a negative deflection of the pain matrix signal through 26.5 minutes followed by a recovery period to a non-pain state at 32 minutes when the cold pressor test was repeated again demonstrating a negative signal deflection denoting a pain state followed by a recovering period until 41 minutes. From the PMD display the correlation of GSR to pain matrix activity shows that during painful stimuli the GSR and pain matrix signals are not synchronous but demonstrate a direct relationship unlike the initial inverse relationship prior to the introduction of pain stimulus. Using the PMD 10, contralateral and ipsilateral sensor data is utilized to calibrate and further discern pain matrix activity enabling a greater understanding of differentiation between various contributors to the individual pain experience.

Using the PMD 10, the analysis, correlation and transformation of data from multiple biophysical measurements allows for brain activity within the pain matrix and patient susceptibility and experience of pain to be better understood. The difference in response evidenced by simultaneous GSR and PainTrace measurements creates additional information regarding variability between brain region activity in the pain matrix, sympathetic response, and emotional processing which are components related to the individual experience of pain. Similarly, the PMD 10 provides for heart rate variability to be simultaneously measured and correlated to determine parasympathetic nervous system activity levels and the relation of vagal tone. (Farmer A et al, Psychophysiological responses to pain identify reproducible human clusters. Pain. 2013 November; Volume 154 (11): 2266-2276). Vagal tone has been evidenced to relate to endogenous endorphin release in response to the presence of pain and therefore measurement of parasympathetic nervous system activity and related vagal tone are important factors to transforming physical biosignals into quantitative and objective measures of the pain matrix and central nervous system activity levels reflective of both states of pain and health and for use as a tool in diagnosis and identifying underlying sources of medical compromise. (Kollarik M et al. Vagal afferent nerves with the properties of nociceptors. Auton Neurosci. 2010 Feb. 16; 153(1-2): 12. Published online 2009 Sep. 13. doi: 10.1016/j.autneu.2009.08.001). In addition to the diagnosis of pain, the PainTrace devices 14 of the PMD 10 provide early diagnosis of intestinal distress, allergies and respiratory infection, sports injury related to tendon and ligament damage, as well as diagnosis of chronic pain related to back injury, dental and migraine cases among others.

Figure 15:
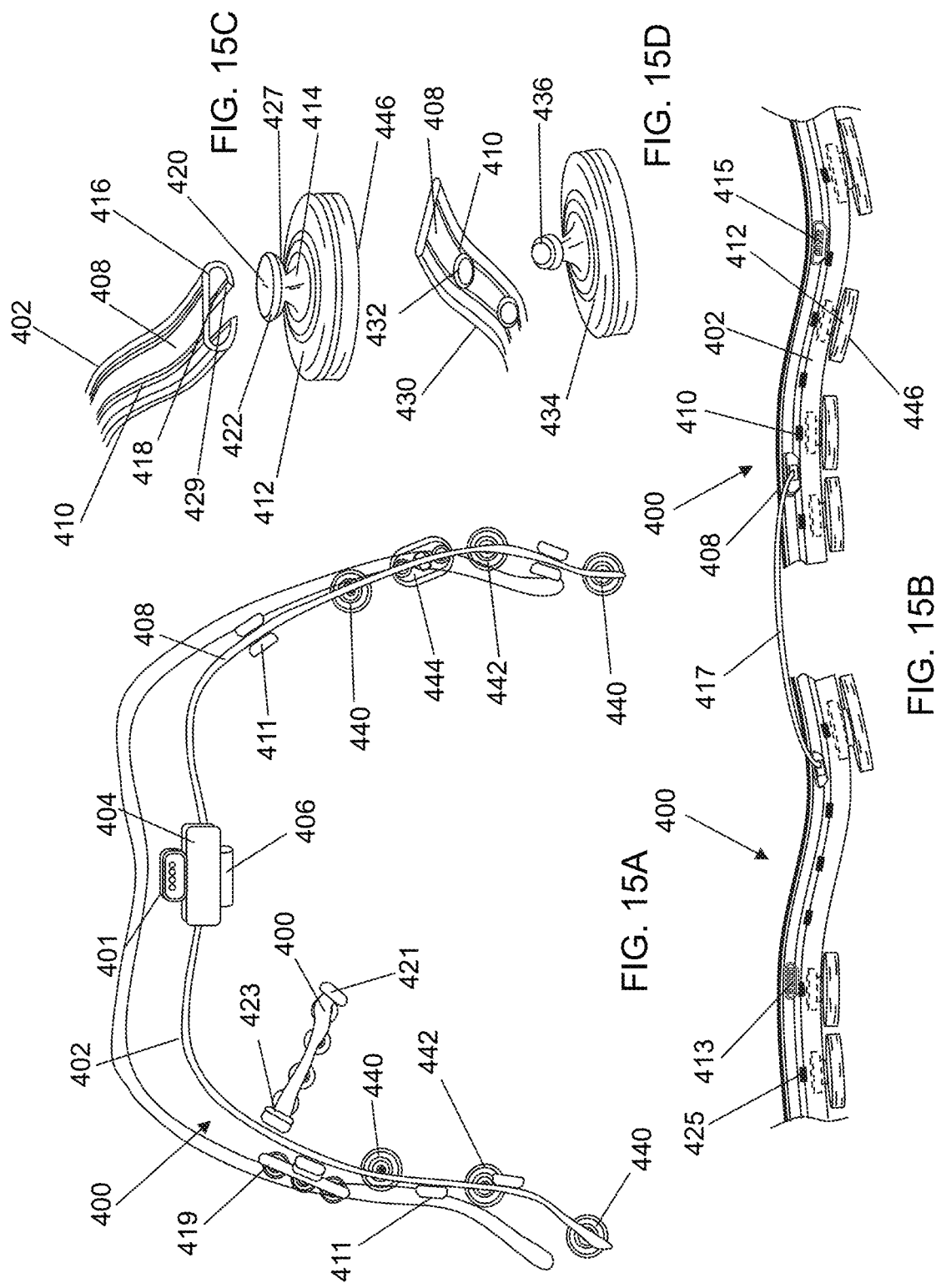
FIG. 15A is a diagrammatic representation of an embodiment of a PMD sensor track and sensors to provide data to an embodiment of the PainTrace application component in an embodiment of the PMD of the present invention.
FIG. 15B is a diagrammatic representation of an embodiment of the connection of two PMD sensor track and sensors to provide data to an embodiment of the PainTrace application component in an embodiment of the PMD of the present invention.
FIG. 15C is an end view of an embodiment of the PMD sensor track and an embodiment of a sensor to provide data to an embodiment of the PainTrace application component in an embodiment of the PMD of the present invention.
FIG. 15D is an end view of a further embodiment of the PMD sensor track and an embodiment of a sensor to provide data to an embodiment of the PainTrace application component in an embodiment of the PMD of the present invention.

In further embodiments sensors or sensor clusters may be sewn or removably attached to clothing or fabric pieces using a flexible sensor holder referred to herein as PMD sensor track 400. The PMD sensor track 400 is a flexible sensor attachment device comprised of an extended strip 402 of plastic, metal or another material that may be formed with a U-shaped channel, an I-beam track, a T-shaped track, or in some embodiments be a flattened piece with openings for the attachment of a series of sensors or sensor clusters, or a matched contour channel. As shown in FIG. 15A, the PMD sensor track 400 may support electronic circuitry which may be within an enclosure 404 or provide an electrical output port 401 such as a USB in a mini or micro size for the attachment of the PMD sensor track 400 to external electronic circuitry. In other embodiments, the PMD is accessed remotely through wireless communication circuitry within the enclosure 404 Bluetooth, NFC, or other types of wireless communication protocols. The PMD provides for the acquisition, control and communication to and from the attached electrodes and sensors of the PMD sensor track 400. The PMD circuitry also provides initialization to detect when sensors are added or removed from the PMD sensor 400 and associate the electrodes and sensors along the strip 402 with a specific patient, HCP, physician, and a clinical or hospital network as described herein. The PMD sensor track 400 may include a power supply 406 or battery to power sensors and apply voltages for calibration of sensors. In some embodiments, the power supply 406 may provide a float current to the electrochemical capacitor of one or more PainTrace sensors to improve energy, power characteristics and sensitivity.

A Velcro or a hook and fastener fabric strip 408 may be provided continually or along portions of the upper or lower surface of the PMD sensor track 400 to flatly adhere the strip to a piece of clothing or fabric. In some embodiments, a strip of adhesive may be provided as well either continually or partially along the upper and/or lower strip surfaces to connect the PMD sensor track 400 to the skin or hair of an animal. Along or beneath the Velcro and/or adhesive strip 408, conductive metallic strips 410 that may be electrically connected to the PMD circuitry through a direct or remote wireless connection are provided. The conductive strips 410 may also be electrically connected to communication connectors 411 installed in locations along the strip 402 of the PMD sensor track 400. The communication connectors 411 may be dual or multi-pin, mini or micro-USB, or other types of electrical connectors suitable to accommodate the data transmission and communication requirements of the sensors, electrodes and PMD circuitry, PainTrace devices 14, other biophysical devices 11 and components and features of the PMD 10.

The communication connectors 411 may be positioned at a single or at multiple locations along or at the beginning or end of the PMD sensor track 400. The electrical connectors 411 may provide for PMD sensor tracks 400 to be interconnected to add or remove sensors to increase diagnostic capability as needed. A shown in FIG. 15B, the PMD sensor track 400 may have a series of male connectors 413 and a series of female connectors 415 so that an electrical wire 417 such as a micro USB cable may be used to connect one PMD sensor track 400 to another. In other embodiments, as shown in FIG. 15A, a sensor cluster 419 may be connected along a portion of the length of the PMD sensor track 400. In other embodiments, an additional PMD sensor track 400 may be electrically connected using an end plug 421. A first end of the PMD sensor track 400 may have a male end plug 421 and the second end may have a female end plug 423 to electrically connect a series of PMD sensor tracks 400 together as needed. In order to communicate and control sensors of different types, the conductive strip 410 includes a series of locator pins 425 that detect and relay a signal when a sensor 412 is attached to or detached from the PMD sensor track 400 at that specific location. Embedded software within the PMD circuitry identifies the type of sensor, the acquisition requirements and other parameters and provides communication protocols to set time and sample rate for data acquisition.

In some embodiments, a sensor 412 is installed to the PMD sensor track 400 by sliding the sensor fastener 414 into and along a U-shaped channel 416 having left and right support rails 418 as shown in FIG. 15B. The sensor fastener 414 may have a flattened top surface 420 and winged extensions 422 with a rounded base 427. The winged extensions 422 are supported on the left and right support rails 418 and the flat upper surface 420 provides for an electrical connection to the conductivity strip 410 to be maintained as the sensor 412 is compressed flat as the attached clothing or fabric is tightened and compressed against the skin. The rounded base 427 provides for movement of the sensor fastener 414 within the U-shaped track as the rounded base 427 along the wedged, curved or slanted edges 429 of the channel rails 418 rolls perpendicularly to the rails 418 and slides along the rails 418 as the sensor 412 is compressed to the skin. By forming the fastener 414 with a rounded base 427, the surface 446 of the sensor 412 remains in contact with the skin as the PMD sensor track 400 and/or clothing is compressed to the skin or as the patient moves while the PMD sensor track 400 is attached.

In another embodiment, the PMD sensor track 400 may be a flattened strip 430 with a series of female parts of a press fastener 432 aligned and secured through openings in the strip 430 as shown in FIG. 15C. The sensor 434 will have a male part press fastener 436 to be inserted into the female part of the press fastener 432 and be secured to the PMD sensor track 400. The female and male press fastener parts may be of a conductive material and electrical strips 410 may be provided to transmit and receive signals from the sensors 434. A Velcro or adhesive strip 408 may be provided along the flattened fastener strip 402 of the PMD sensor track 400. The sensor fastener 436 may be of a rounded shape to roll within the opening and prevent movement of the patient or PMD sensor strip 400 from pulling the sensor 430 away from the skin. In other embodiments, the sensor fastener may be a partial oval shape to slide over the rails of an I-beam or T-shaped track or of any shape that provides for the sensor to be correctly oriented and the fastener 436 to freely move within the connection to the strip 402 to prevent the sensor from tipping and being pulled from the surface of the skin during movement. Other fasteners and track shapes and dimensions are contemplated within the scope of this component of the PMD system 10 of the present invention.

The sensors 412 may be positioned in optimal locations along the PMD sensor track 400 with respect to the area on the body being measured, the size of the person, the clothing worn, the amount of time the sensors 412 will be used, the type of sensor 412 being used and other factors. A range of sensors of different capabilities and electrical requirements may be provided with the power supply or battery 406 supplying power as needed. In some embodiments, the sensors may be permanently affixed to the PMD sensor track 400, using adhesives, staples, thread, clips, snaps or other fasteners. In some embodiments, the PMD sensor track 400 may be disposable. As shown in FIG. 15A, the extended flexible material of the PMD sensor track 400 provides for bending and shaping the strip 402 in order to properly place sensors or sensor clusters in proper location to acquire pain matrix activity data, EDA, PPG, HRV, GSR and other biophysical information. For example, the PMD sensor track 400 may provide for separating two ipsilateral sensors 440 along each side, position contralateral sensors 442 in similar locations, and support a PPG monitor with all of the data collected and analyzed within the PMD system. The PMD sensor track 400 may be secured within a shirt using the Velcro strip 408 to wrap the PMD sensor track 400 around the neck and shoulders and affix the sensors along the clavicle and chest for readings. The flexibility of the PMD sensor track 400 contours the surface 446 of the sensor 412 to the irregularities of the skin or hair of an animal. An adhesive conductive gel layer may be provided on the surface 446 of each sensor 412 to adhere the sensor to the body.

In a further embodiment, the PMD sensor track 400 may be used with compression clothing or fabric such as with an elastic bandage, athletic tape, bandeau or other article of clothing to align the PMD sensor track 400 on a location around the arm, leg, or torso of the body and compress the sensors to the surface of the hair or skin. In this manner there may not be a necessity for gels or adhesives on the skin to hold and maintain continuity of the surface 466 of the sensor to the skin to optimize readings. The fabric of the elastic bandage or article of clothing may be tightened to the body to compress the sensors on the skin using Velcro or other fasteners. As part of the PMD system that integrates data from numerous sensors and references, the PMD sensor track 400 provides for multiple sensors and sensor clusters to be easily connected and aligned to the skin to improve the continuity of each sensor and overall data acquired from the PainTrace and other biophysical sensors.

In further embodiments, the dosage of pain medications may be evaluated based on individual PainTrace Factors 102 and direct measurement of the PainTrace device 14 before and after administration of a pain medication. Pre and post-administration PainTrace Factors 102 will provide efficacy data based on dosage, and by monitoring over time can evaluate tolerance and the need to evaluate alternate interventions to provide an individualized pain management regimen.

In further embodiments, the tolerance threshold for pain or from other sensor readings may be used for the administration of medication through for example an automated pump dispenser. Limits on dosage and time between administration of the medication may be set and then based on the data collected from the pain measurement device, the pump may dispense medication when sensor readings exceed pain tolerance level settings. Particularly, for an incapacitated patient the automated medication delivery system using the PainTrace sensor readings may prove effective to control and maintain levels of medication as needed. As shown above, the administration of medication and pain levels may be tracked and reviewed to determine the efficacy of treatment using the PainTrace Application 70 and other components and features of the PMD 10.

In a further embodiment of the present invention, the PMD 10 may identify patients at high risk for dependency on medication. The PainTrace sensor data may be used in a unique way to prevent the abuse of medication by controlling when a patient has access to their medication based on the pain matrix activity and pain tolerance readings collected. In a first embodiment, a secure pill box, or other medication dispenser may be locked using an electronic security code. The patient may be given an identification code to unlock the pill box, however this security code may be overridden by the PainTrace sensor readings when the sensor readings are well below the pain matrix activity and pain tolerance levels for the patient. Once tolerance levels are exceeded, the lock is activated and the patient may enter their identification code or alternatively simply open the pill box. Another embodiment is that if appropriate pain matrix activity and pain tolerance levels are measured the patient would receive single-use passcode via the mobile device app to open the pill box a single time and then the passcode would be reset. In this way the amount of medication taken by the patient may be controlled and only be accessible when pain levels are at appropriate levels and require treatment. Timers integrated with the secure pill box could further prevent access to the medication prior to a set time limit in order to have prescribed time intervals between the administrations of medication. Healthcare provider goals and pain management agreements could be integrated into the system.

Figure 16:
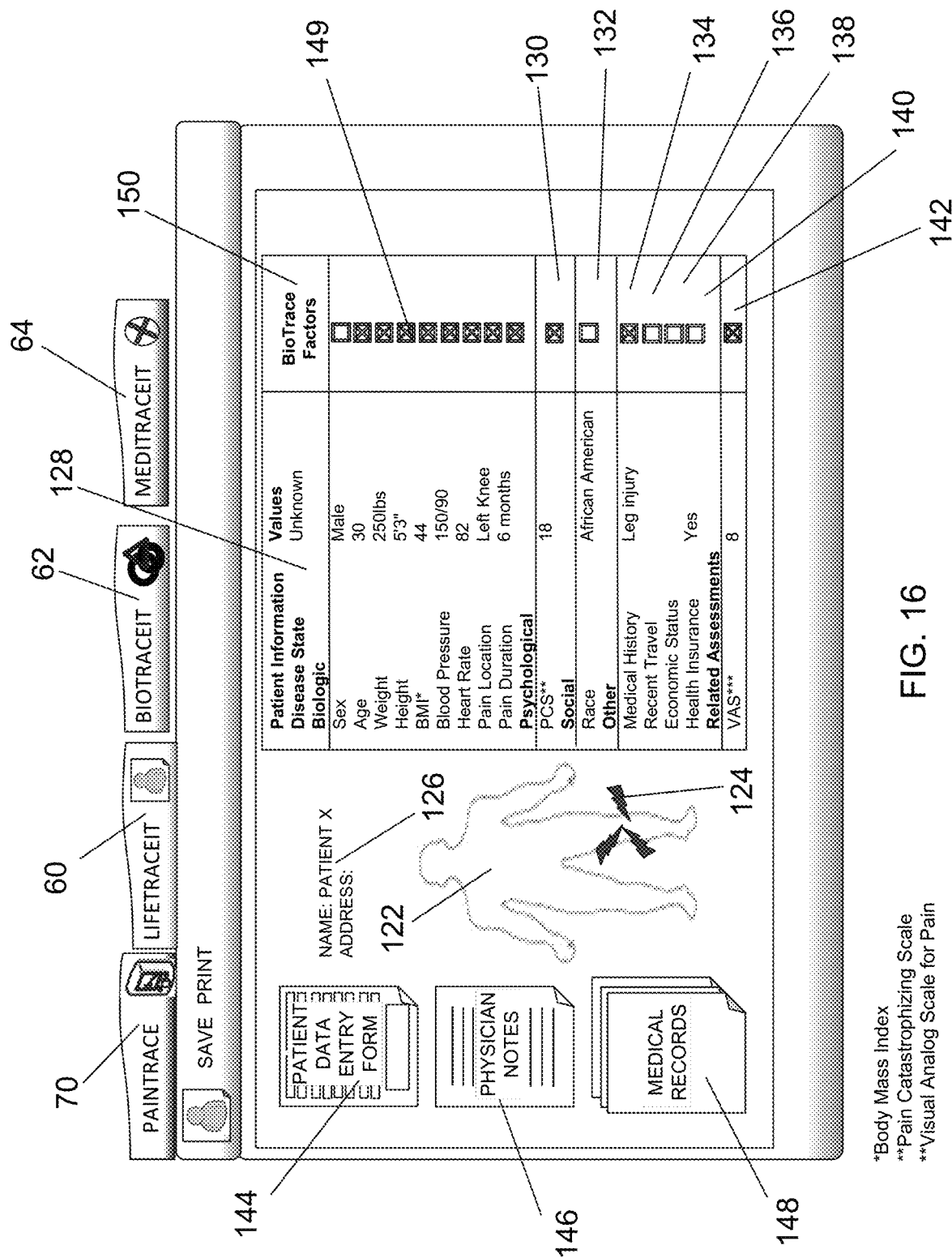
FIG. 16 is a diagrammatic representation of an embodiment of the BioTraceIT application component incorporating data from the LifeTraceIT application component in an embodiment the PMD of the present invention.

The components and features of the PMD 10 provides biological data specific to the patient and combines this information with the PainTrace application 70 data. This information may be presented within the BioTraceIT component 60, as shown in an embodiment in FIG. 16, through other components of the PMD 10 and/or through another patient information application. For medical personnel, the BioTraceIT component application 60 may display a diagrammatic human representation 122 of the patient based on the biological data. The diagrammatic human representation 122 may not provide any identifying features, but for verification and analysis, it may assist the HCP with the general characteristics of the sex, shape, and size of the patient. The diagrammatic human representation 122 may further provide a pain location indicator 124 to allow the HCP to quickly verify the region of distress. For example, a shorter patient with larger features based on the weight, height and body mass index (BMI) with a pain in the left knee is shown in FIG. 16. The name and other identification information of the patient may be provided in some embodiments, in further embodiments to protect confidentiality of the patient identifier code 126 may be provided to distinguish the patient record from other patients. General biologic data may be listed in a table 128 with labels and values describing physical features of the patient. The biologic data may further include psychological evaluations 130, social data 132, medical history 134, recent travel 136 and/or any other information that may be relevant to diagnosis and treatment may be included within the patient data. The data may further include data that may be considered unrelated to diagnosis and treatment such as data related to economic status 138 and insurance coverage 140 to be used within the MediTraceIT component 64 of the PMD 10. If available, or using features of the PMD 10 information may be added, including data from other pain measurements or ratings such as the Visual Analog Scale (VAS) for comparison with the objective PainTrace Factor 102. The PMD 10 provides for the display to be customized so that different factors may be selected beyond a core factor template based on advanced user options and preferences.

The data may be integrated with the PMD 10 through electronic health records or through survey information from patients. If available, patient records are uploaded from an Electronic Health Record (EHR) and are associated with the Patient Identifier Code 126 that links the patient's health records to the LifeTraceIT application 60 or other patent data application. If the EHR is not available, the patient may be prompted for pertinent information such as age, height, weight, comorbidities, and other information. The patient may further be provided with a Consent Form that informs the patient of how this data will be used, privacy policy, and terms and conditions with respect to the sharing of their data that will be utilized to improve the healthcare communities understanding of a particular health problem/disease state and to improve diagnosis and treatment. The Patient Privacy policy may present information on the legal and ethical responsibility to safeguard patient privacy and the privacy of all patients and protect the confidentiality of their health information and medical records. These health records may include information about test results from blood samples, physical examinations, medical history and any other data collected or reviewed during the course of your treatment for the patient. The confidential information may also include personal information such date of birth, as well as medical records from a primary care physician where any health information that could be used to identify a patient is called "Protected Health Information" (PHI). The BioTraceIT PMD server system 18, outside of any institution, keeps the patient anonymous and instead has only the objective of looking at large groups of individuals to better understand health challenges and improve patient outcomes. In requesting patient data for use within the software application, the PMD 10 may require acknowledgement of acceptance by the patient to use the data beyond use in the acquisition of data from the PainTrace sensor 14 and other medical devices. The LifeTraceIT application 60 or other patient data application may further provide access to the survey information 144 submitted by the patient to the physician. Features of the PMD 10 may further provide access to prior medical records 146 of the patient and to a data entry application 148 for the physician to enter notes on diagnosis and treatment. The patient survey may provide for a patient to create a personal health record that they can access through their electronic health record via the hospital network 16, or through a separate software applications as available options for the patient to elect, providing for the patient to track treatment and access reference materials related to their disease state.

The patient survey may have a series of questions, that the PMD 10 may iterate and direct to particular questions based on the received answers. In this manner, the patient will be stepped through screens to answer questions pertinent to their particular health problem, symptoms, emotional state and disease state. In the most basic example, a first question pertaining to whether the patient is male or female the software will present a question on pregnancy in the female survey, but not in the survey presented to a male patient. The survey questions may relate to basic demographics, specific behavioral/environmental/psychological/social factors, specific short-forms and developed questionnaires for both the evaluation of certain parameters and correlation to existing data already gathered via widely utilized assessment tools, such as assessment questionnaires and/or tools related to pain that may include: SF-MPQ; BPI-SF; TOPS; SF-36;

WHYMPI; VAS; PGIC; NRS; and others. The questions and surveys included to gather data are stored to be used periodically to possibly be given to the patient again to re-evaluate correlations between Biotrace Factors as treatments and outcomes are further understood.

The survey may include general questions on age, gender, ethnicity, height, weight, and occupation to provide baselines and establish the patient within a general population of patients. The survey may then ask more specific and immediate questions to determine current physiology, psychological state and symptoms that as example questions may be as follows with specific selection box, rating scales, or data entry boxes for the patient to respond:

In the past seven days. In general, how would you rate your physical health?
☐ Excellent
☐ Very Good
☐ Fair
☐ Poor In general, how would you rate your mental health, including your mood and your ability to think?
☐ Excellent
☐ Very Good
☐ Good
☐ Fair
☐ Poor In general, how would you rate your satisfaction with your social activities and relationships?
☐ Excellent
☐ Very Good
☐ Good
☐ Fair
☐ Poor Do you exercise? How often?
What if any exercise or high level of physical activity did you complete in the last 48 hours?
Do you take any medications? What?
Have you experienced a recent injury? If yes, please explain:
Do you have any continuous or regular pain that you experience on a daily basis? If so. Where?
How long have you experienced this pain?
Assessment using VAS: Please rate your current level of pain if any on the scale below.
Have you experienced, or currently are experiencing any of the following:
A list of disease states such as cancer, stroke, heart attack, surgery Other general health questions may be taken from a standard health survey such as the SF-36 Health Survey. All answers are compiled and associated with the patient or code for the de-identified patient and are presented within the LifeTraceIT component application 60 or other patient data application by the PMD 10.

The data may further be linked to the BioTraceIT analysis application 62 for a HCP to access patient diagnostic readings (e.g. pain levels), analyze those readings, and see factors that may contribute to elevated or suppressed readings (e.g. age, weight, comorbidities, etc. may affect pain levels). The administrative tools module 21 of the PMD 10 may provide access to specific information to be controlled by an administrator, so that a physician may be provided access to all patient information, while another HCP may through a login and password be provided with only test results, medication, or treatment information specifically as necessary and related to their interaction with the patient.

Figure 17:
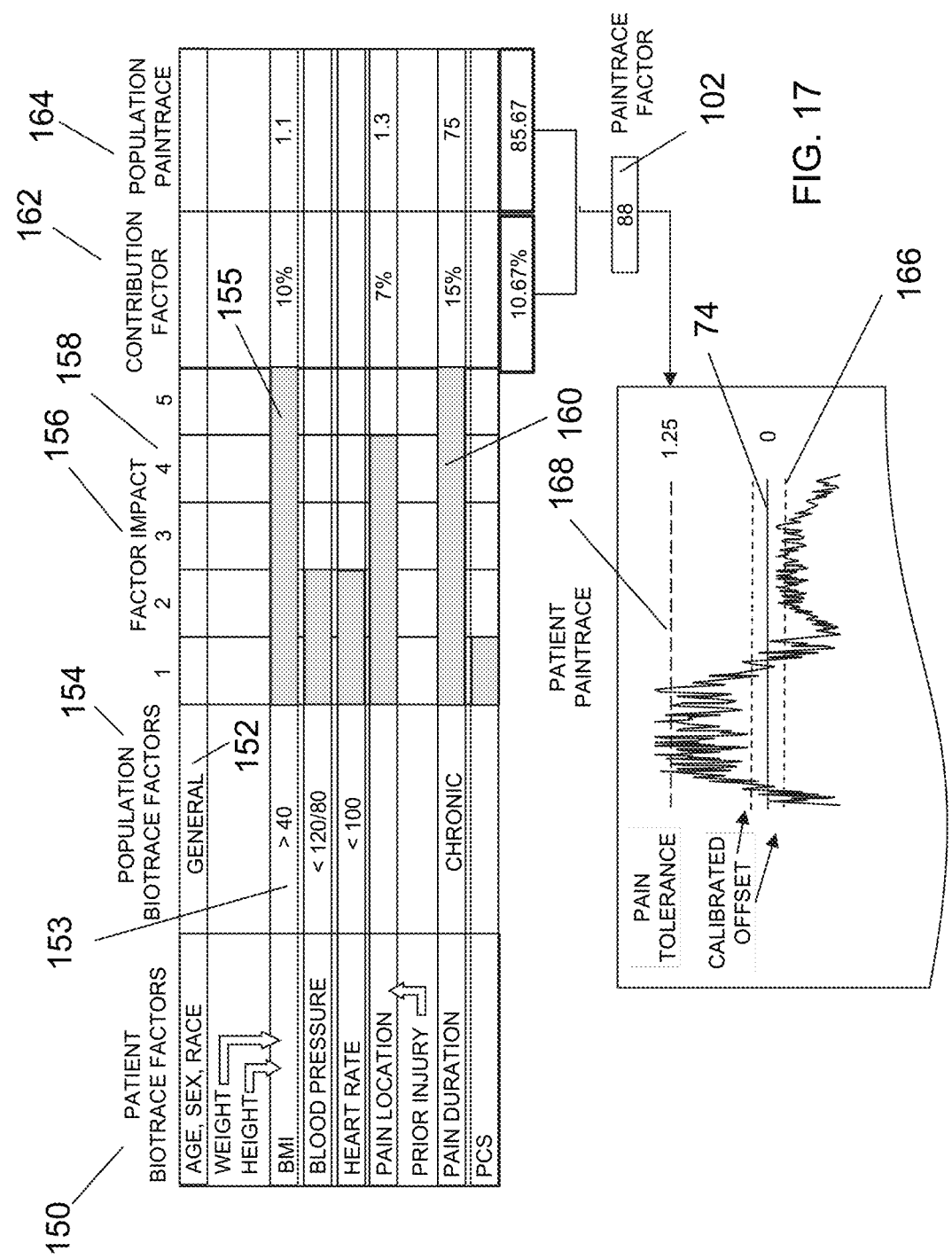
FIG. 17 is an embodiment of the PainTrace data and BioTrace Factors used to determine a PainTrace Factor and pain tolerance threshold in an embodiment the PMD of the present invention.

As shown in FIG. 16, the physician or HCP with proper administrative access may review the biological data 128 and select any factors that they believe are relevant in diagnosis using check boxes 149. These factors referred to herein as the BioTrace Factors 150 are also analyzed using statistical and comparative algorithms within the data analysis module 27 in relation to populations and disease states based on reference materials and accumulated patient data. In general, the PMD 10 will have an evolutionary nature, in that it will constantly be updated with data input from health care providers who are gathering "BioTraceIT" data on patients suffering from various disease states and with reference materials 22 from medical journals and periodicals based on particular disease states found within the population of patients providing data. In an embodiment, the PMD 10 gathers data related to acute and chronic pain that are comprised from biological, psychological, and social measures, and other relevant fields and combines this data with an acute or chronic disease state, and with the diagnostic PainTrace data and other accumulated data points. The PMD 10 integrates the gathered data in a HIPAA compliant manner, or in an appropriate fashion to protect patient privacy rights, in order to parallel and integrate data on patients using a biopsychosocial platform, or one that comprises other appropriate factors for data points, to further increase the understanding of a disease state. For example, the PainTrace data measuring the manifestation of pain in the nervous system may be combined with data regarding biological, behavioral, environmental, psychological, and social factors to determine the impact of these factors on the level of pain experienced by the patient. As shown in FIG. 17, an analysis of the Biotrace Factors 150 may be provided through a comparison first of general factors 152 to a population similarly situated such as patients of the same age, sex, race and other similar Biotrace Factors that may be relevant such as patients experiencing a similar location of pain. The population Biotrace Factors 154 may be presented as a range of values such as acceptable blood pressure and heart rate readings. The data analysis module 27 of the PMD 10 compares the patient's Biotrace Factors 150 to the population Biotrace Factors 154 and further performs a global analysis of how the patients biological data may relate to others to determine a Factor Impact level 156 on a scale 158 of for example 1-5 and indicators 160 are presented to display a level of impact that a patient's Biotrace Factor 150 might have in order to assist the HCP in understanding the importance and potential concern and need for intervention related to the Factor. For example, a Body Mass Index (BMI) that exceeds 40 indicated as 153 and shown within the general Population Biotrace Factors 154 may have the highest Factor Impact level 5 as indicated by 155 to warn the HCP of risks due to obesity. The data analysis module 27 identifies the Biotrace Factors 150 having the highest Factor Impact levels 156 and performs searching of known reference materials related to these factors to determine a Contribution Factor 162 that is a statistical percentage estimate of how much a Biotrace Factor 150 may influence a patient's perception of pain as augmented or diminished to account for the subjective nature of pain. The data analysis module 27 further performs a comparison of PainTrace data signals 72 and PainTrace Factor 102 of the similar population and with the determined Contribution Factor 162 to calculate the PainTrace Factor 102 as a percentage of variation between the pain matrix response to stimuli and what the patient experiences; considering the biopsychosocial evaluation of pain. By deriving the PainTrace Factor 102 from pertinent patient demographics an evaluation and response to standardized noxious stimuli with respect to current assessment tools such as VAS may provide for more valid and objective pain readings. PainTrace Factor values 102 with respect to the VAS may be made with comparisons of female vs. male; young vs. elderly; VAS equal to 1-3 vs. VAS equal to 3-6 vs. VAS equal to 7-10 to determine the relationship of the PainTrace Factor 102 to the VAS. However, unlike the VAS, the PainTrace Factor 102 is adjusted by any pre-existing conditions such as surgery in the past 3 months or diabetes for the past 3 years that will affect the normalization of diagnostic readings in comparison to the patients Biotrace Factors 150. The PainTrace Factor 102 may further be used to establish an initial pain tolerance level 168. While the initial pain tolerance level 168 may be adjusted for the patient as data is collected, the baseline provides for comparisons and analysis particularly for patients that are non-communicative or for animals. The PMD 10 may further perform a comparative calibration on output data from the PainTrace device 14 and set an offset 166 for voltage readings to properly determine pain measurements.

Figure 18:
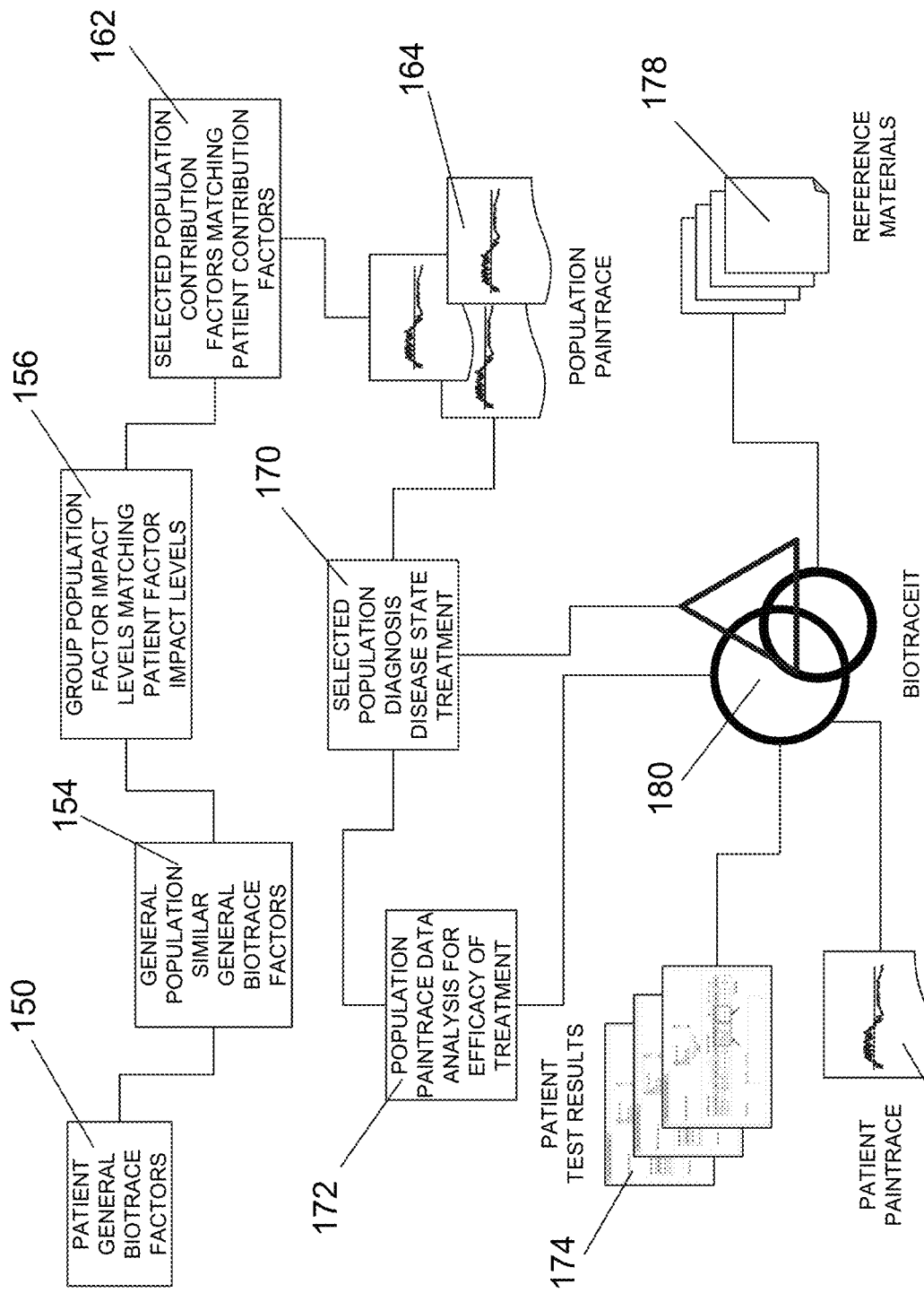
FIG. 18 is a flow chart showing an embodiment of BioTrace Factors that may be used to develop the BioTraceIT analysis in an embodiment the PMD of the present invention.
Figure 19:
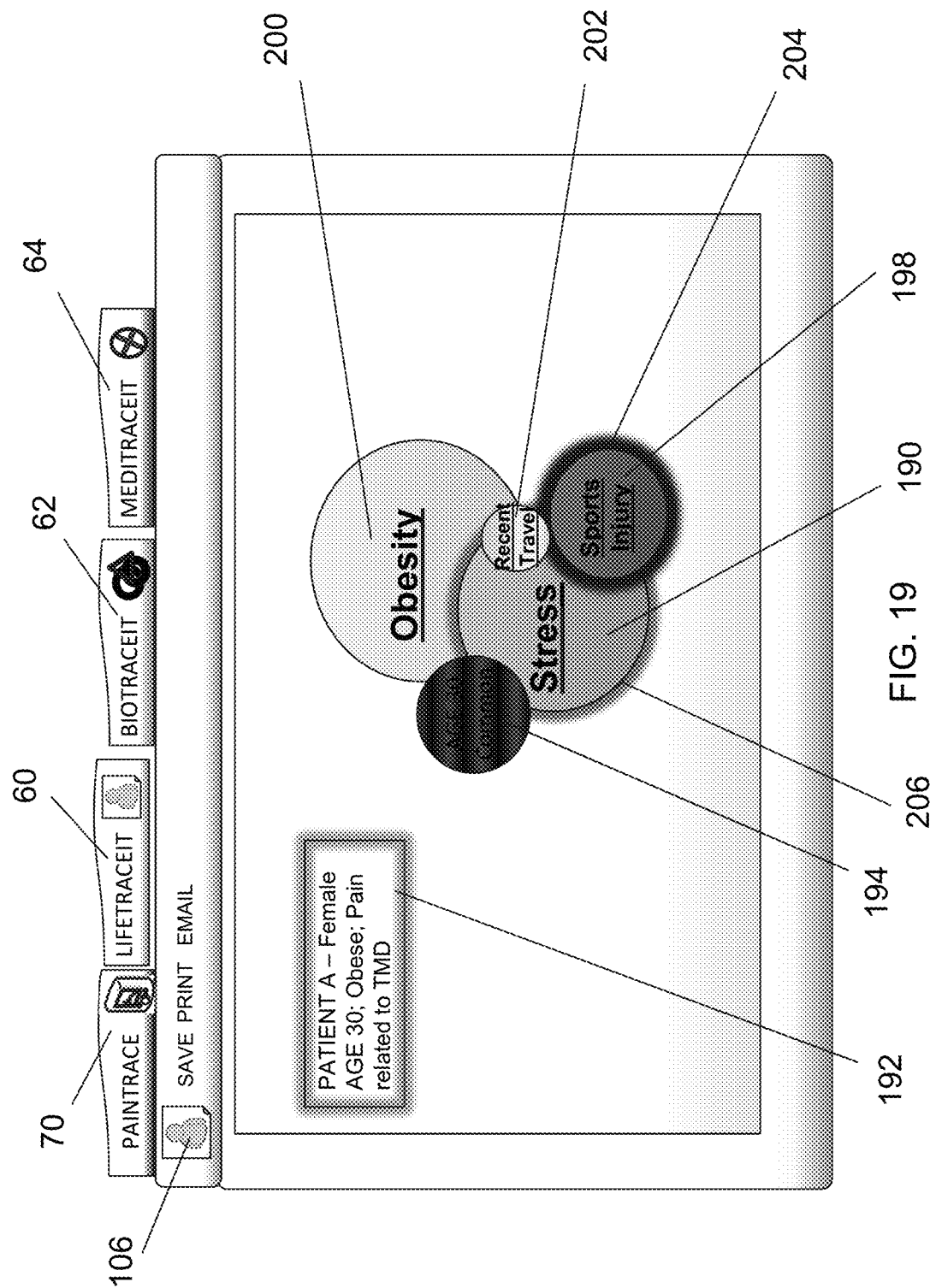
FIG. 19 is a diagrammatic representation of an embodiment of the BioTraceIT application component in an embodiment the PMD of the present invention.

From the comparison of general Biotrace Factors 150, Factor Impact levels 156, Contribution Factors 162, and the Population PainTrace Data 164 large amounts of data are statistically structured providing for the PMD 10 to perform analysis and comparison of the most well suited members of the selected population first. The PMD 10 may first review pain measurements from the Population PainTrace data 164 for members having the same general population Biotrace Factors 154, similar Factor Impact levels 156, and related Contribution Factor percentages 162 as shown in FIG. 18. From the selected population having these statistical similarities, the PMD 10 performs data analysis of the diagnosis and tests performed for a particular disease state 170. The PMD 10 further performs data analysis of the efficacy of treatment 172 of this selected population. The PMD 10 compiles these analyses in summary sheets that provide highlights of similar diagnosis and outcomes. The information collected is then combined with patient test results 174, patient PainTrace data 176 and related reference materials 178 and a BioTraceIT 180 is generated for analysis by the physician in the BioTraceIT component application 62. As shown in FIG. 19, a BioTraceIT 180 increases the understanding of various disease states via a multi-dimensional data analysis platform derived from the statistical computations of the physiological readings and the diagnostic relevance of the BioTrace Factors 150. As described herein, BioTrace Factor groupings may be developed based on general traits such as age, sex race, disease states if known, but once identified differences within these populations may be extracted using the impact levels, and contribution factors. From the selection of patients that exhibit high levels and large contributing factors, an analysis of pain trace data and PainTrace Factor values 102 and treatments within this population, can assist a HCP in the development of test protocols, diagnosis and treatment for the patient. The BioTraceIT provides the HCP with a summary and of this analysis. The efficacy of treatment may then be analyzed. The BioTraceIT component application 62 provides analysis through a biological tier and through a clinical tier. The biological tier analysis as described above and shown in FIG. 18, analyzes the combination of the Patient BioTrace Factors 150, the Physiological Readings from the PainTrace device 14 or other sensors and Contributing Factors 162 related to a knowledge base of acute and chronic disease states. This biological tier is focused mainly on the patient's health, history, lifestyle as it relates to similarly situated populations, physiological readings and the BioTrace Factors 150 that contribute to alter an individual's subjective perception of pain. The biological tier functions to translate the subjective into objective data via the analysis of the contributing factors. The resulting PainTrace Factor value 102 may be further compared to the VAS or other objective measures to improve the overall accuracy of the normalized perception for pain of the patient.

The clinical tier of the BioTraceIT component application 62 provides an analysis of the combination of symptoms, the clinical data, and treatment protocols. The clinical tier is focused mainly on exhibited symptoms, test results including blood and urine based analysis, and associated treatment protocols. The combination of the Biological Tier and Clinical Tier allows for objective physiologic data in complex disease states to aid in the analysis of potentially successful treatment protocols and proof of efficacy based on improvements related to objective measurements. The PainTrace device 14 objective measurements of pain provides data to evaluate efficacy and drive future use of treatment protocols based on patient populations, acute and chronic disease states, and contributing factors that affect subjective experience of individual patients.

The BioTraceIT application 62 provides access to all pertinent information through the patient data icon 106, drop down menus, tabs, and/or other software features. Within a drop down menu, the BioTrace Factors 150 may be listed in order of relevance which is based on analysis of a Biotrace Factor value as it relates to the Factor Impact level 156 to derive the Contribution Factor 162. The greater the value of the Contribution Factor 162 the higher that Biotrace Factor 150 is listed in the drop-down. A Biotrace Factor 150 may be chosen from a drop-down menu and be dragged and dropped into the display to evaluate the Biotrace Factor 150 as to its relevance to the patient's disease and symptom experience. Further resources and information can be accessed to provide data, explanations, research, and relevant treatment options by clicking through subsequent depth of information. A visual review of the patient Biotrace Factors 150 and relevance is developed for quick analysis of what will best improve a patient's health by understanding the individual patient's health background and particulars that most impact the patient's symptoms that will lead to improved outcomes.

Within the BioTraceIT component application 62, the analyzed data representations may be represented by variations in size, shape and color of icons as shown in FIG. 19. The size of an icon may represent larger patient populations and/or more common symptoms. The HCP may click larger icons first to review obvious factors that are initially easy to address such as stress 190 contributing to Temporomandibular Joint Disorder (TMD) where patient and diagnostic information may be provided in a dialog box 192. The Biotrace Factors 150 are evaluated using unique statistical algorithms to present correlations between the patient biophysical state, disease state, medical history, reference materials and using other sources to identify significance of one diagnostic constituent such as stress, how the constituent may relate to the patient's pain and any relationship, contributing factor or outlier, that may require further analysis to determine or confirm the patient's diagnosis and treatment. The BioTraceIT Application 62 may present patient age 194 as a factor, the patient's medical history such as the identification of a sport's injury 198 within the region of pain, and obesity information 200, as an example. Each diagnostic constituent may be presented using unique combinations of elements within the display to represent rare contributing factors or rare symptoms for patient in for example smaller icons, and more frequent prevalent factors in larger icons. By displaying size and color relationships between these BioTrace Factors 150, an HCP may validate diagnosis with larger supporting and contributing constituents. However, BioTrace Factors 150 displayed in smaller and muted colored icons may draw the attention of the HCP to a constituent that although not obvious could be a contributor to the patient's symptoms that may be easily missed. For instance, the patient has joint pain, they are seemingly healthy, but contracted a microbe traveling abroad which may cause leaky gut which could be associated with joint pain and nausea. A recent travel icon 202, although small within the display, may point to an alternative diagnosis.

Figure 20:
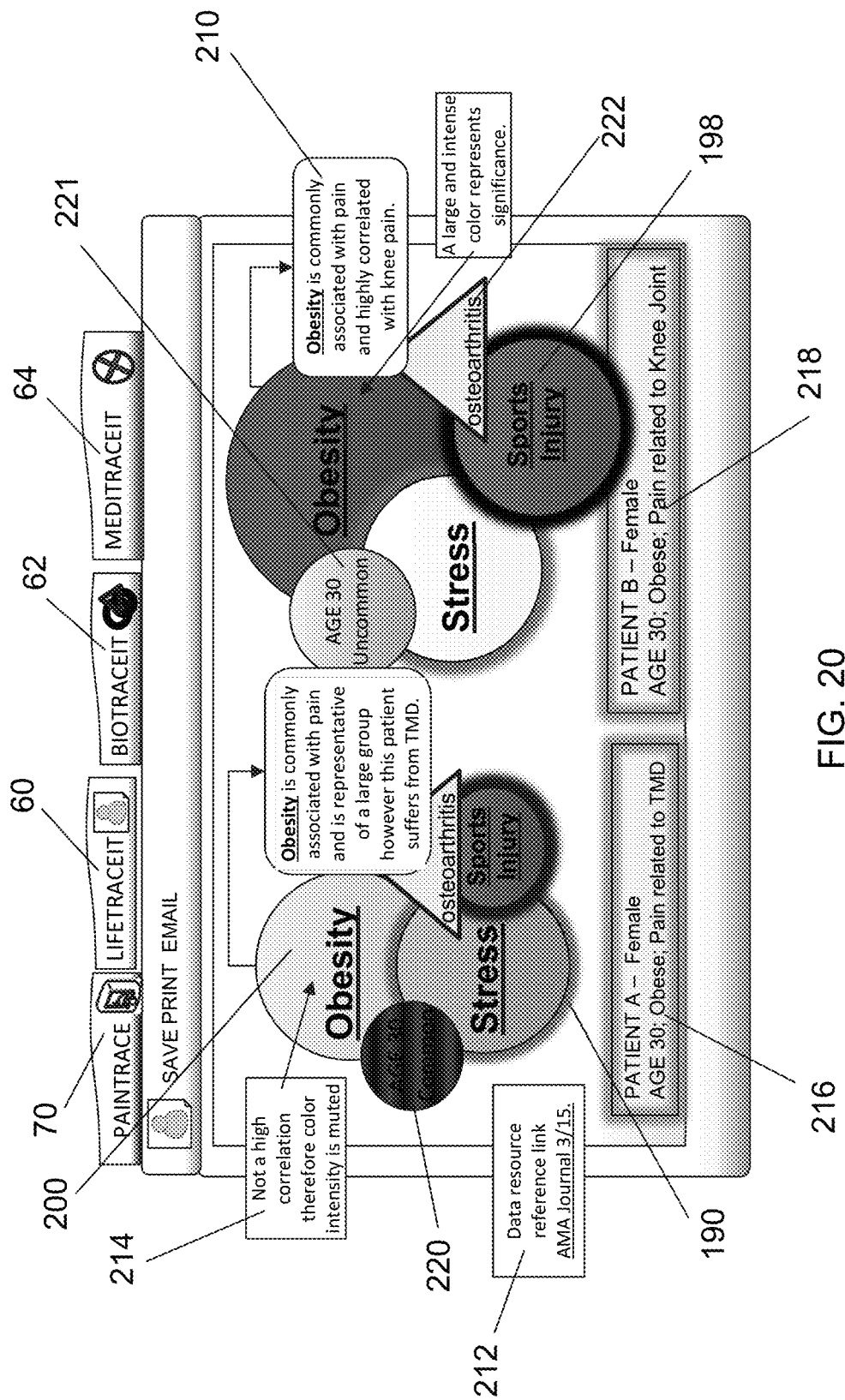
FIG. 20 is a diagrammatic representation of another embodiment of the BioTraceIT application component in an embodiment the PMD of the present invention.

The color of the correlated BioTrace Factors 150 may allow an HCP to quickly determine the significance of BioTrace Factors 150 that are known to highly correlate with the exhibited symptoms and largely contribute to diagnosis. As an example, primary colors may present this significance. In the example above, the bright yellow icon 202 indicating that the patient may possibly have a leaky gut caused by ingestion of a microbe is easily identified in a primary color causing a physician to take interest in a less common BioTrace Factor 150 that has a high correlation of Factor Impact 156. Factor Impact 156 can increase in correlation based on duration of symptom, timing of possible ingestion of microbe, type of microbe, known symptoms that are exhibited, travel to certain areas and other BioTrace Factors 150. The PMD 10 provides for indicators to be tied to time blocks to visually provide the time and duration of BioTrace Factors 150 that may be critical to proper diagnosis. The BioTraceIT Application 62 further provides a correlation of BioTrace Factors 150 that have a low correlation with symptoms and are not commonly known to influence patient perception. These low correlation BioTrace Factors 150 may be presented as muted colors. A color ring or border 204 indicator around an icon may represent a factor that has the potential to affect a physiological sensor reading in this instance pain as in this example where stress in a muted colored ring 206 may be a BioTrace Factor 150 that can increase perception of pain and therefore the patient's expressed pain may be augmented and not a clear indicator of the degree of the physical problem. The BioTraceIT Application 62 visually represents using the color, size, and shape indicators to allow an HCP to investigate correlations further to improve the diagnosis and overall treatment of the patient. The PMD 10 further provides reference links to medical journals, and patient data within one environment to assist in having an HCP arrive at a well-supported diagnosis and treatment plan as quickly as possible. As shown in FIG. 20, a comparison of BioTrace Factors 150 may provide for a physician to determine appropriate tests as derived from the statistical analysis and correlation of BioTrace Factors 150 completed by the BioTraceIT Application 62. A testing protocol may be presented as a different shape such as a triangle to indicate the significance of the correlation and that further tests may possibly provide a more complete diagnosis. The BioTraceIT Application 62 provides for each icon to be selected to present patient data related to the BioTrace Factors 150, i.e. weight tracked over time for obesity, compared with tracked outcome measures, e.g. decrease in pain over time. The statistical relevance of any BioTrace Factor 150 and/or what treatments were used; and related research and treatment protocols approved by the clinic or institution may be provided and may also be presented in dialog boxes 210, pull down menus, and/or through links 212 that open the other components and features of the PMD 10, related patient information with those applications, or to open documents or other data resources. The significance of the color, shape and size of icons may also be provided in an icon description dialog box 214.

In this example, the OBESITY icon 200 shown as a larger icon may be a common factor in patients experiencing joint pain. However, Patient A 216 is suffering from TMD and therefore extra weight would not be responsible for excessive stress on temporomandibular joints. Therefore, while the OBESITY icon 200 may be almost as large as the STRESS icon 190 it is in a MUTED COLOR due to a lower correlation between this BioTrace Factor 150 and the patient's TMD related symptoms. However, the STRESS icon 200 may be slightly less prevalent in the general population and therefore have a smaller size compared to OBESITY icon 200 and be in a secondary color due to lesser relevance among the general population. Stress may cause physical activity, such as teeth grinding that can aggravate and cause TMD. Additionally, stress can increase a patient's pain experience which may increase their symptoms. For this reason, in Patient B 218 while stress is a muted color it has a PRIMARY COLOR RING which denotes that this BioTrace Factor 150 affects the physiological readings in this case of pain.

The SPORTS INJURY icon 198 represents an even smaller population but can have significant correlation in the diagnosis of both Patient A 216 and Patient B 218 examples as both knee pain and TMD can be caused by a prior sports injury. For example, if Patient A was playing hockey and was hit in the jaw with a hockey stick this injury may have a higher correlation depending on the nature of the injury. Targeting each BioTrace Factor 150 from each individual whether it be physiological and social in nature such as stress, or physical in nature such as a prior injury combined with associated physiological readings associated with the PainTrace data and other data acquired from other sensors leads to a greater understanding of the effectiveness and tracking of treatment outcomes. Furthermore, the duration of pain, if untreated and chronic or maladaptive in nature, can increase the perception of pain, known as hyperalgesia, hence the darker hued COLOR RING to denote the Factor Impact of a sports injury on perception of symptoms. The bright color of the FEMALE AGE 30 icon 220 for Patient A 216, indicates that TMD is most common in females age 20-40. This age group is less relevant for knee pain so the icon 221 is a MUTED COLOR. From the correlation presented in the BioTraceIT Application, an OSTEOARTHRITIS TEST TRIANGLE 222 indicates that the BioTrace Factors 150 may support a diagnosis of osteoarthritis as significant where ~14% suffer osteoarthritis by the age of 24 and after age 65 the incidence rises to 35%. Due to the age of the patient this would be a more relevant factor in an elderly patient. Since the patient is age 30 this BioTrace Factors 150 represents a small population however if they suffer from osteoarthritis this would have significant relevance. There is no evidence of osteoarthritis but testing/imaging as indicated by the testing triangle 222 to rule out arthritis may be valid. Understanding contributing BioTrace Factors 150 and relevance, and tracking treatment outcomes using the PainTrace sensor data and data from other sensors, may lead to potentially more effective and expeditious diagnosis and treatment resulting in improved health, shorter times to return to work and daily activities, and a subsequent reduction in healthcare spending due to improved treatments resulting in faster recoveries and a decrease in lost work days which further positively impacts the economy.

Figure 21:
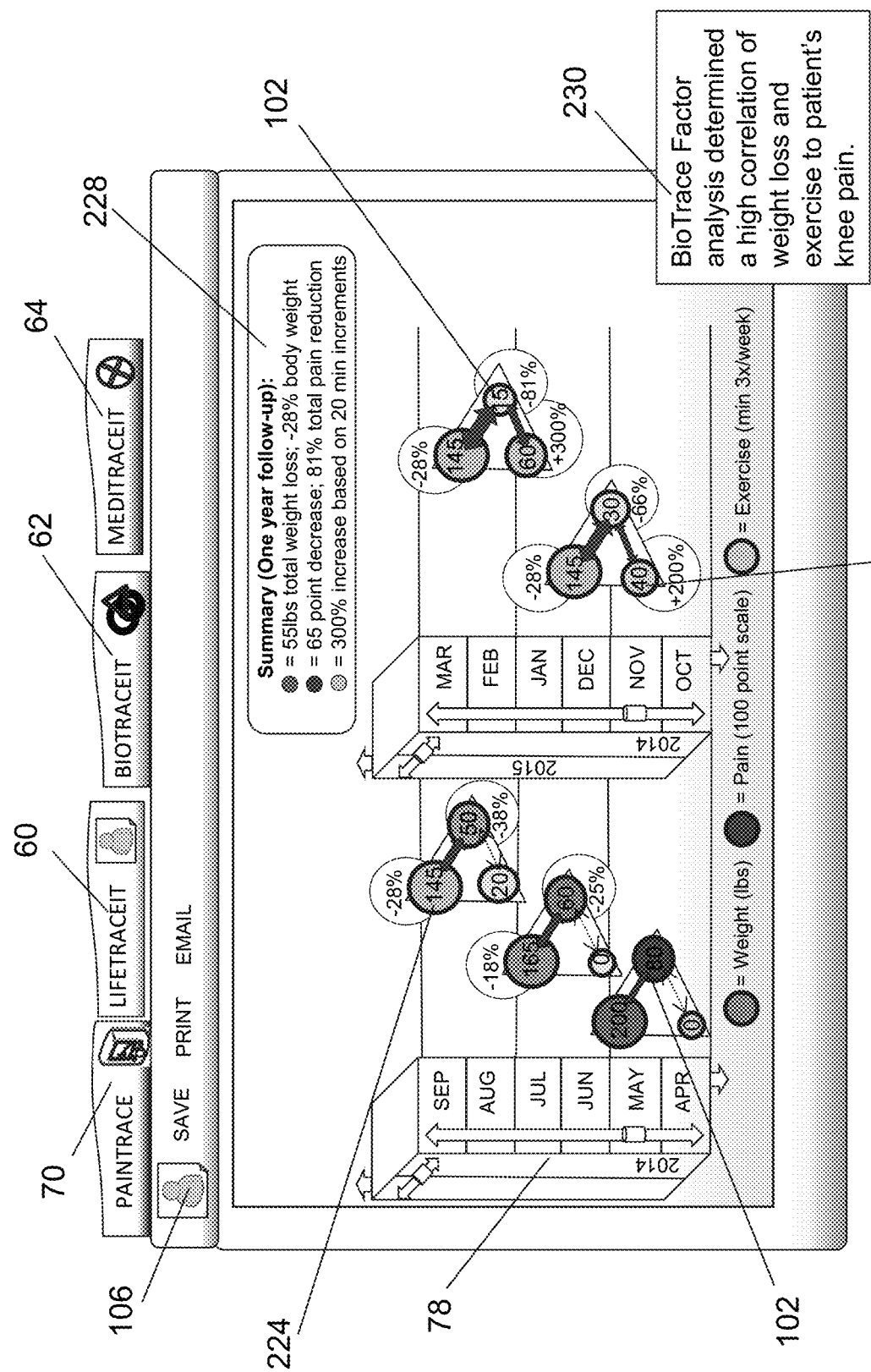
FIG. 21 is a diagrammatic representation of still another embodiment of the BioTraceIT application component in an embodiment the PMD of the present invention.

Through the BioTraceIT Application correlation and analysis, which revolves around pain as a central symptom to evaluate and diagnose illness, disease state, health, and healing, an HCP might recommend weight loss and target one or more BioTrace Factors 150 that may be significant to diagnosis and treatment. Subsequent patient visits, data from the PainTrace Application 70 and LifeTraceIT data would allow the HCP to track selected target factors with the BioTraceIT Application 62 providing visual comparisons showing time span, duration and effect of actions and treatments taken by the patient based on physiological readings and logged activity gathered to evaluate effectiveness of treatments and interventions which can further be transformed into a BioTrace Progress Score 280 which provides a cumulative score based on all criteria for quick reference and simple tracking of outcomes. As shown in FIG. 21, the software would automatically track and graph progress and relate patient information, such as weight loss, and correlate with improvement in symptom. The target factors may be related to the Pain Trace Factor 102 that provides an indication of increases or decreases in pain. The weight 224 of the person may be tracked and visually displayed. The time block 78 may represent any acceptable scale such as weeks or months to display changes in the targeted BioTrace Factor 150. A comparison of the data over time or with respect to different patients or populations may support strategies for more effective results. While exercise is well known to contribute to the reduction of weight, presenting a third BioTrace Factor 150 of exercise 226 over a time period and resulting weight loss as well as pain reduction, is an important correlation that may be effective to make a patient change their behavior. A summary 228 and BioTrace Factor Analysis 230 may also be accessible through the BioTraceIT Application 62. The BioTraceIT Application 62 would provide statistical significance of correlation to improved outcome; provide average improvements over a period of time, such as patient lost five pounds per week over a two-month period, where using LifeTraceIT software eating patterns and food choices could additionally be correlated to improvements as well as evaluation of targeted patient engagement and the impact on behavior change and decision making. Positive impact individual patient activity and decision making would contribute to an increase in a positive BioTrace Progress Score 280. Decreases in use of medication and subsequent cost savings would then be tracked for use by the MediTraceIT component 64 of the PMD 10. The BioTrace Progress Score 280 can be used as a metric for both the BioTraceIT software and the MediTraceIT software applications within the PMD 10. The BioTrace Factor 150 data may further be analyzed for subsequent software updates to PMD 10 for improved objective measurements and factor impact algorithms.

Figure 22:
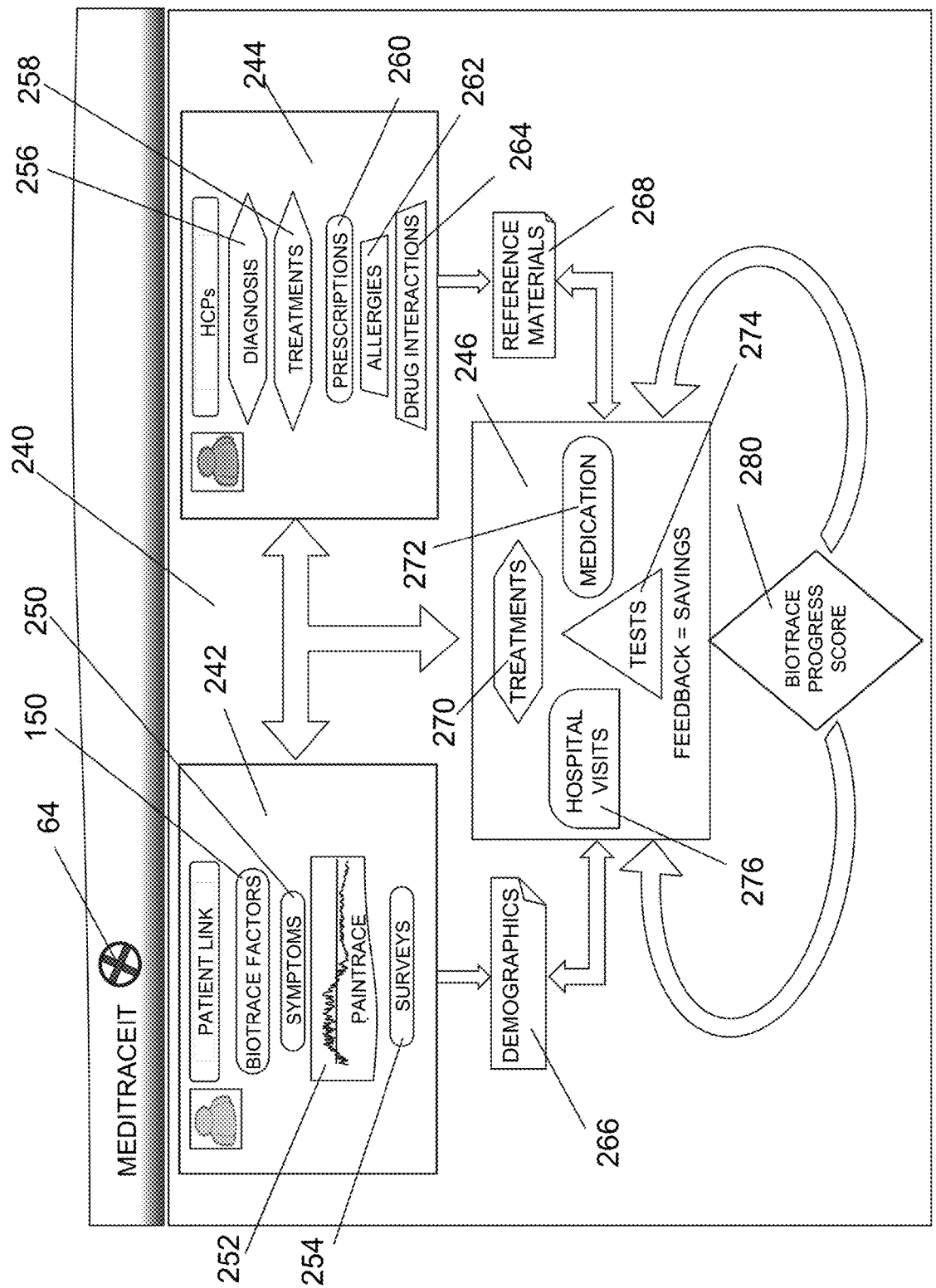
FIG. 22 is a diagrammatic representation of an embodiment of the MediTraceIT application component in an embodiment the PMD of the present invention.

End-users may also view data without using icons and review in a typical spreadsheet and bar graph format. Whether viewing in a visual or a graphical format, a user can click on each BioTrace Factor 150, Factor Impact 156 or Contribution Factor 162 for explanation of relevance, resources, related studies, treatment protocols, and correlated patient data as well as other information to assist and support effective diagnosis and treatment. If an institution chooses they may link this data to the MediTraceIT component 64 of the PMD 10 and through an integration with their electronic medical records be provided with representations of BioTraceIT Progress Scores 280 reflecting outcomes showing improvement over subsequent patient visits to show efficacy of treatment, review how subsequent interventions are related to initial symptoms and treatment, and additionally review the healthcare costs related to treatment. As shown in FIG. 22, the MediTraceIT component 64 may provide a dashboard interface 240 that provides for the user as an HCP, physician, administrator or others to select patient data within a Patient Link module 242, review actions taken related to the patient's health care within a Health Care Provider (HCP) module 244 and analyze treatments with respect to costs within a Cost Analysis Module 246. The Patient Link module 242 provides access to components and features in the PMD 10 related to the patient's BioTrace Factors 150, the patient's symptoms 250, the patient's PainTrace data 252, and access to Surveys 254 of the patient that may provide status of the patient's current health. The HCP module 244 may provide access to information on determined Diagnosis 256, Treatments 258, and Prescriptions 260 that may also provide access to allergies 262 or drug interaction 264 information. The MediTraceIT component 64 may further provide access to a Demographic module 266 for treatments and cost comparisons presented for patients having similar BioTrace Factors 150 and BioTraceIT Progress Scores 280 a Reference module 268 to provide information on acute and chronic disease states. Each of these modules of the MediTraceIT component 64 of the PMD 10 may provide detailed information about the patient and the patient's diagnosis and treatment to allow a user to verify and validate steps taken by the HCPs and physicians in treating the patient.

The Cost Analysis Module 246 provides costs associated with the steps taken in Treatments 270, Medications 272, Tests 274, and Hospital Visits 276. The costs information 280 may be restricted using administrative tools that set access levels and permissions based on the user. However, the MediTraceIT application 64 may be targeted to the physician and healthcare provider using LifeTraceIT 60 and BioTraceIT 62 and the pain measurement data to track treatment outcomes in order to present the cost benefits realized from successful outcomes. By tracking treatment outcomes, positive results are reinforced based on the patient's willingness and adherence to the requirements of the treatment resulting in costs benefits which may be returned to the patient in the form of insurance discounts for example. Costs benefits are further realized by having a physician more quickly identify ineffective treatments and/or to remedy misuse of medication by a patient. Using MediTraceIT 64 with the outcome tracking of BioTraceIT 62 and physiological readings of the PainTrace data, healthcare costs may directly correlate treatment with objective measures of improved outcomes as evidenced by decreased pain levels for the patient. This comprehensive approach using the components of the PMD 10 provides improved diagnostic analysis, validation of treatments and the realization of cost benefits within an easily accessible software application that correlates and presents data in a useful and effective way for patients, HCPs and physicians.

Example 1

The measurement of pain matrix activity using the PainTrace device 14 of the PMD 10 is shown before and after acupuncture treatment in FIG. 23. Prior to treatment a mean pain level of 9.4 mV in a patient having low back pain was recorded. The patient self-reported a VAS value of four (4) prior to treatment. After treatment, the mean pain level decreased, represented by a positive reading of 6.4 mV and the patient self-reported a VAS value of zero (0). Using the PMD, a change in pain matrix activity was observed indicating a successful response to treatment. Furthermore, a quantitative measure of "health" as described as a degree of no pain is available.

Example 2

Figure 24:
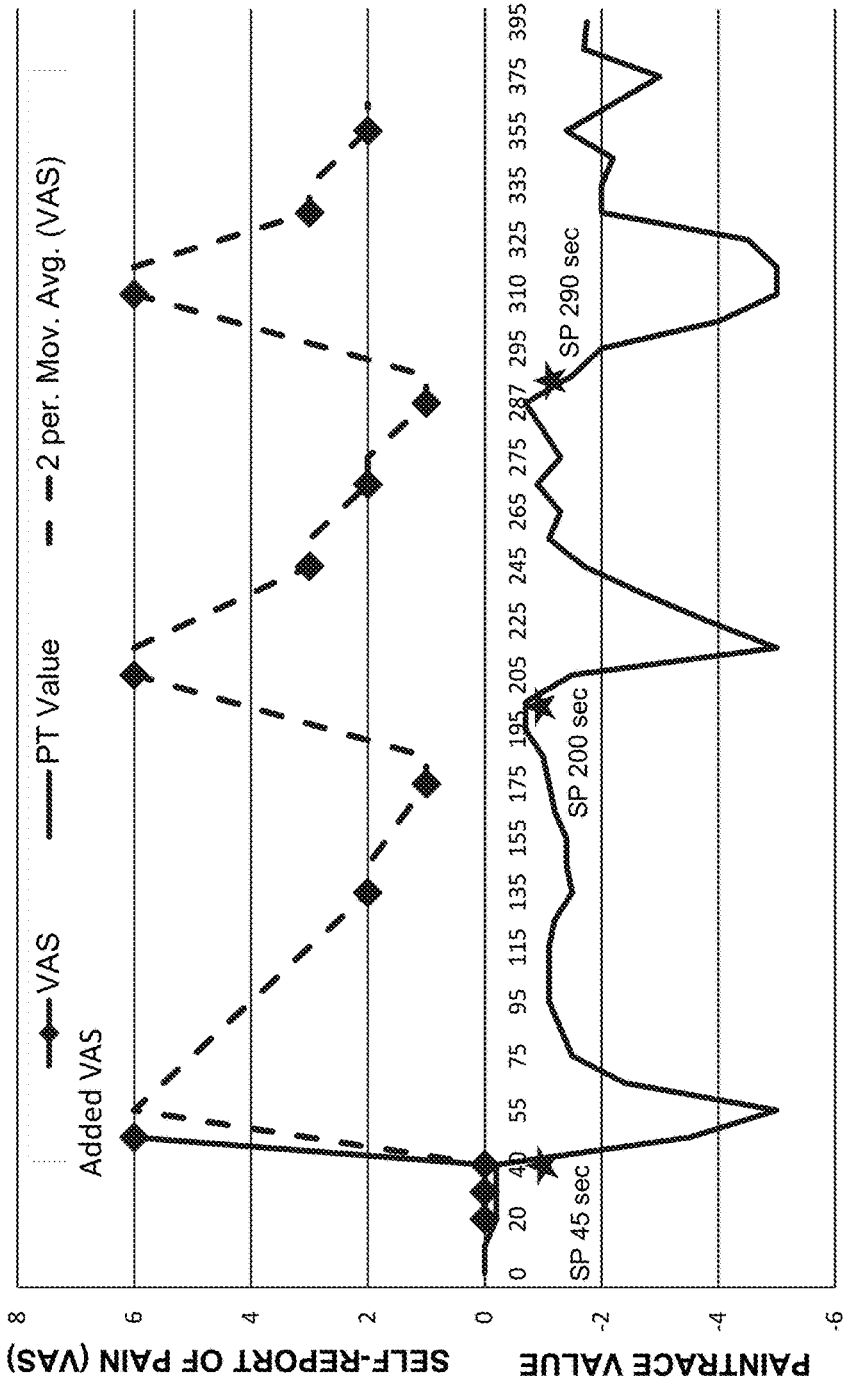
FIG. 24 is example PainTrace data as compared to VAS self-reporting in an embodiment of the PMD of the present invention.

In FIG. 24, a patient having an axillary nerve injury was examined to determine shoulder pain and healing progression. During the seven (7) minute reading, over 395 seconds, the patient self-reported an initial VAS value of zero (0) during the initial 40 second recorded baseline period. At 40 seconds the shoulder was externally rotated, noted as a noxious stimulus, to exasperate the axillary nerve injury and generate pain. Pain matrix activity increased as measured using the PainTrace device of the PMD as indicated by the deflection from the baseline to a reading of approximately −5; reflecting an increase in pain. In subsequent shoulder rotations stimulating a pain response at 200 second and at 290 seconds, the pain matrix activity as measured by the PainTrace device 14 correlated with the self-reported VAS values. A VAS value was not recorded, during the initial noxious stimulus at 40 seconds. An extrapolated value was added for graphical purposes that is equivalent to the subsequent VAS scores and corresponding measurement by the PainTrace device 14 as indicated by the diamonds and matching trend and inflection points of the measured PainTrace data. Correlating this data with BioTrace Factors 150 including patient populations using the PMD demonstrates a quantitative measure of pain matrix activity and real-time monitoring.

Example 3

Figure 25:
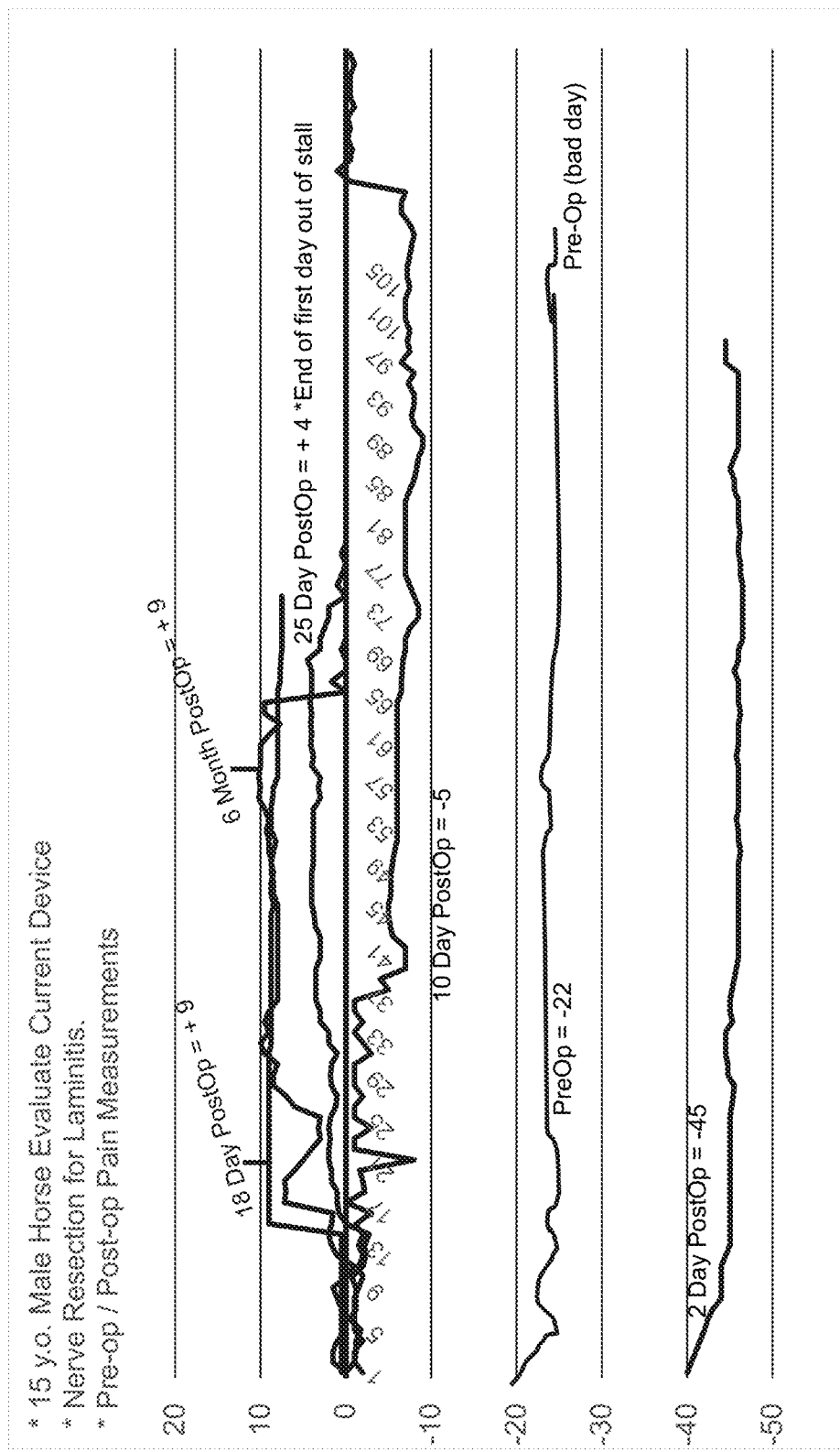
FIG. 25 is example PainTrace data collected over a sixth month period of a horse suffering from laminitis in an embodiment of the PMD of the present invention.

In FIG. 25, a horse diagnosed with laminitis was measured using the PainTrace device 14 of the PMD 10 prior to nerve resection surgery to alleviate pain to the affected foot, and exhibited a −22 in deflection from a zero baseline pre-surgery. Two days after surgery pain measurements were taken and a −45 deflection was shown. After 10 days of recovery the pain matrix activity had decreased to a −5 deflection. By the eighteenth day post-op, the readings increased to +9 and horse exhibited a pain-free post-surgical status. On day twenty-five, the horse was allowed out of its stall for the first time post-surgery and pain matrix activity registered a level of +4 which as a deflection from the +9 readings denotes some pain, or a level of fatigue, in the animal. After six months of recovery, PainTrace device 14 measurements were taken and the horse exhibited the same non-pain readings of +9 and was diagnosed by a veterinarian to have fully recovered from surgery.

Example 4

Figure 26:
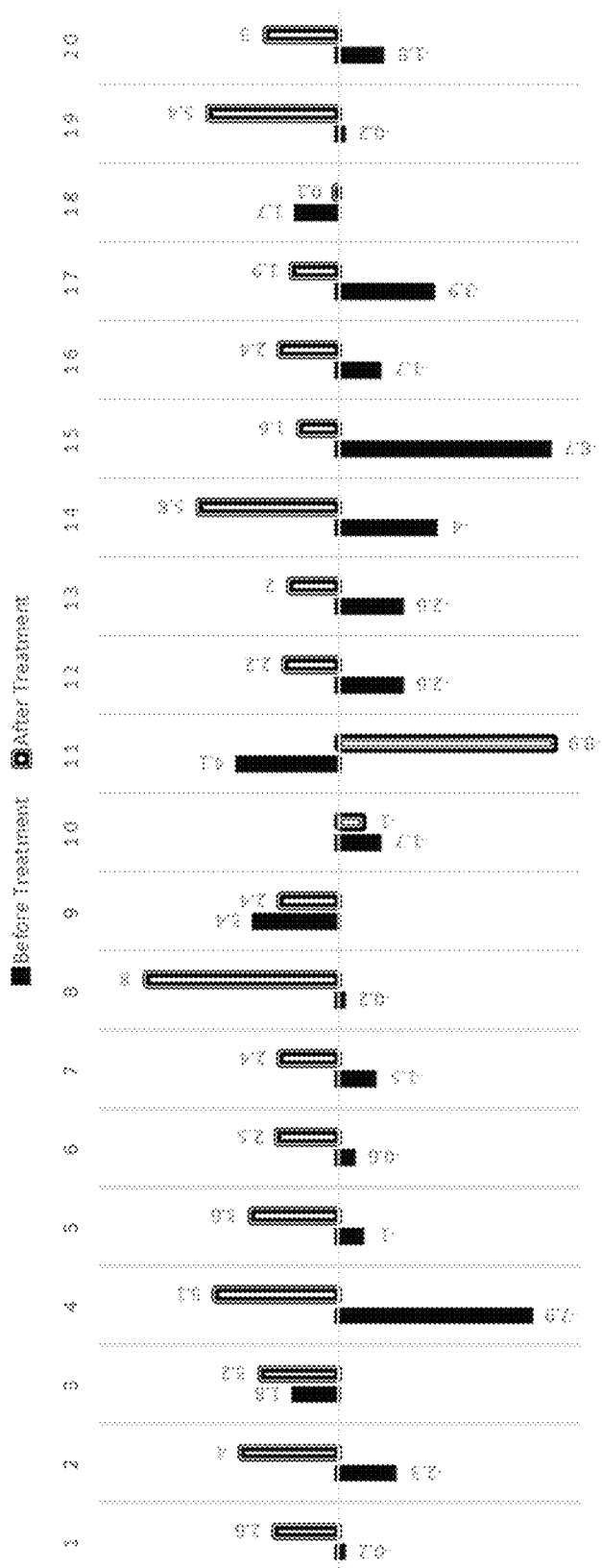
FIG. 26 is example PainTrace data showing the changes in pain measurements before and after treatment for twenty patients in an embodiment of the PMD of the present invention.

As shown in FIG. 26, in a twenty (20) person study of lower back pain patients receiving acupuncture treatment, the PainTrace device 14 of the PMD was used to measure and monitor pain matrix activity before and after treatment over five (5) consecutive outpatient visits. In 18 of the 20 cases, treatment resulted in decreased pain measurement levels with results ranging in deflection values from 1.0 to 13.0. In Subjects 10 and 11 there was a negative deflection of the PainTrace device 14 measurement indicating more pain post-treatment compared to pre-treatment values. Further investigation of the Subject 11 revealed that the subject had fallen during the visit and was experiencing both the pre-existing back pain and recent leg pain simultaneously. Acupuncture treatment was performed specifically for the lower back, and had minimal effect on the other injury. The PainTrace device 14 accurately detected continued pain in the subject and provided information on successful treatment outcomes for the other individuals within the study.

Although the present invention has been described in some detail by way of illustration and example for purposes of clarity and understanding it will, of course, be understood that various changes and modifications may be made in the form, details, and arrangements without departing from the scope of the invention.

What is claimed is:

1. A method of quantitatively measuring pain, using a pain measurement and diagnostic system and data output from contralateral sensors comprising:
   accessing a non-transitory computer readable medium within a network of central processing units having memory and data storage and having embodied thereon one or more computer programs causing one or more of the central processing units to execute certain steps of:
   accessing data acquired over a period of time from data output from contralateral sensors configured to measure pain matrix activity of an individual, the data acquired without the individual experiencing a noxious stimulus;
   determining an average of the measured pain matrix activity acquired over the period of time as the individual's baseline pain matrix response levels, the average of pain matrix activity over time capable of providing an indicator of chronic pain;
   displaying the average of the measured pain matrix activity as a visually perceptible element;
   accessing data acquired over a period of time from data output from the contralateral sensors configured to measure pain matrix activity of the individual, the data acquired during the application of a noxious stimulus to the individual;
   determining an average of the measured pain matrix activity acquired over the period of time during the application of the noxious stimulus as a noxious stimulus baseline of the pain matrix activity of the individual;
   identifying the difference in the average of the individual's baseline pain matrix response levels to the average of the noxious stimulus baseline of the pain matrix activity, the difference in the average of pain matrix activity providing an indication of a change in pain matrix activity;
   displaying the difference in the average of the measured pain matrix activity as a visually perceptible element;
   identifying a deflection from the individual's baseline pain matrix response levels at the point in time of a noxious stimulus;
   determining a delta at the point in time of the deflection as the difference in the pain matrix activity measured prior to the noxious stimulus and the pain matrix activity measured at the point in time of the noxious stimulus, the delta representing the level of the increase in pain from the noxious stimulus;
   displaying the delta as a visually perceptible element indicating a pain score configured to represent the change in pain state related to acute pain, the pain score analogous to the currently used standard scales for self-report;
   identifying deflections from the baseline as pain matrix response levels of the individual;
   accessing BioTrace Factors as data related to the individual's biological, psychological, and social data comprising previously acquired data related to pain matrix activity including pain matrix response levels, as data related to the individual's biology and history, and the individual's response to stimuli, events, treatments, and activity and demographics data comprising one of at least age, gender, ethnicity, height, weight, a rating of physical health, a rating of mental health, a level of physical activity, recent travel, injury, disease state, medications, genetics, biomarkers, and medical and personal history, and as data related to the individual's self-reported measurements of pain, symptoms, emotion, opinion, memory, and trauma;

identifying a population having BioTrace Factors similar to the individual's BioTrace Factors, as data related to the individual's biological, psychological, and social data and comprising previously acquired data related to pain matrix activity including pain matrix response levels of the similar population, data related to biology and history of the similar population, and data related to the response to stimuli, events, treatments, activity, and demographics data comprising one of at least age, gender, ethnicity, height, weight, a rating of physical health, a rating of mental health, a level of physical activity, recent travel, injury, disease state, medications, genetics, biomarkers, and medical and personal history of the similar population, and data related to self-reported measurements of pain, symptoms, emotion, opinion, memory, and trauma of the similar population;

accessing pain matrix response levels of the similar population;

correlating and ranking the individual's biophysical data to the biophysical data of the similar population;

correlating and ranking the individual's demographics data to the demographics data of the similar population;

normalizing pain matrix response levels of the individual to pain matrix response levels of the population based on the correlations and rankings;

determining a PainTrace Factor based on a scale derived from a comparison of data from the individual's pain matrix response levels with and without the application of a noxious stimulus to data from pain matrix response levels with and without the application of a noxious stimulus of the population having similar BioTrace Factors;

monitoring data from contralateral sensors configured to measure the individual's pain matrix activity through treatment; and accessing data acquired from the contralateral sensors during pre-treatment, treatment, and post-treatment;

determining an average of the measured pain matrix activity acquired pre-treatment as the individual's pre-treatment baseline pain matrix response levels;

determining an average of the measured pain matrix activity acquired post-treatment as the individual's post-treatment baseline pain matrix response levels;

identifying a difference in the average of the individual's pre-treatment baseline pain matrix response levels to the individual's post-treatment baseline pain matrix response levels as a change in pain matrix activity indicating an increase or decrease in pain providing an indication of the effectiveness of the treatment;

displaying the difference in the average as a visually perceptible element as an indicator of the effectiveness of treatment;

identifying deflections from the individual's pre-treatment baseline pain matrix response levels and post-treatment baseline pain matrix response levels;

determining the deltas at the point in time of each deflection as the difference in the initial pain matrix activity measured and the subsequent pain matrix activity measured, the delta representing increases or decreases in pain, the deflections from the baseline at a point in time indicative of a change in pain state related to acute pain of the individual;

displaying the deltas as a visually perceptible elements indicating pain score configured to represent the change in pain state related to acute pain at different points in time, the pain score analogous to the currently used standard scales for self-report;

correlating the identified deltas to time-stamped events during the pre-treatment pain matrix response levels and the post-treatment pain matrix response levels with an increase or decrease in response levels indicative of the change in pain state; and correlating the measured deltas with self-report pain scales of the individual and or group of individuals of the similar population exhibiting similar traits, treatments, and emotions and other biological, psychological, and social data identified as BioTrace Factors;

correlating changes to one or more interventions, life changes, activity changes, and other remedy, stress, or stimulus that may impact biological, psychological, and social data comprising previously acquired data related to pain matrix activity including pain matrix response levels, as data related to the individual's biology, history, and response to stimuli, events, treatments, activity, and demographics data comprising one of at least age, gender, ethnicity, height, weight, a rating of physical health, a rating of mental health, a level of physical activity, recent travel, injury, disease state, medications, genetics, biomarkers, and medical and personal history, and as data related to the individual's self-reported measurements of pain, symptoms, emotion, opinion, memory, and trauma.

2. The method of quantitatively measuring pain of claim 1, comprising accessing data of measured pain matrix activity acquired without applying voltage and averaging the pain matrix response activity over a selected period of time.

3. The method of quantitatively measuring pain of claim 1, comprising accessing data of measured pain matrix activity acquired using contralateral sensors.

4. The method of quantitatively measuring pain of claim 1, comprising accessing data of measured pain matrix activity acquired using ipsilateral sensors by applying voltage.

5. The method of quantitatively measuring pain of claim 1, wherein the BioTrace Factors comprising data related to the individual's biophysical data including monitoring of the individual's heart rate and correlating and ranking the individual's heart rate data to heart rate data from the population having similar demographics.

6. The method of quantitatively measuring pain of claim 1, wherein the BioTrace Factors comprising data related to the individual's biophysical data including monitoring of the individual's heart rate variability and correlating and ranking the individual's heart rate variability data to heart rate variability data from the population having similar demographics.

7. The method of quantitatively measuring pain of claim 1, wherein the BioTrace Factors comprising data related to the individual's biophysical data including measuring activity of the individual using a motion detector and correlating and ranking the individual's activity data using a motion detector to activity data from the population having similar demographics.

8. The method of quantitatively measuring pain of claim 1, wherein the BioTrace Factors comprising data related to the individual's biophysical data including measuring of the individual's blood pressure and correlating and ranking the individual's blood pressure data to blood pressure data from the population having similar demographics.

9. The method of quantitatively measuring pain of claim 1, wherein the BioTrace Factors comprising data related to the individual's biophysical data including measuring of the individual's galvanic skin response and correlating and ranking the individual's galvanic skin response data to galvanic skin response data from the population having similar demographics.

10. The method of quantitatively measuring pain of claim 1, wherein the BioTrace Factors comprising data related to the individual's biophysical data including measuring of the individual's skin temperature and correlating and ranking the individual's skin temperature data using a motion detector to skin temperature data from the population having similar demographics.

11. The method of quantitatively measuring pain of claim 1, comprising:
  accessing data from the population having similar BioTrace Factors; and
  identifying treatments and treatment outcomes of the individual and treatments and treatment outcomes of the similarly situated population and correlating these treatments and treatment outcomes to the biosignal deflections related to pain matrix activity to determine the effectiveness of the individual's treatment based on a decrease in pain matrix response levels.

* * * * *